United States Patent
Peer Mohamed et al.

(10) Patent No.: US 11,590,142 B2
(45) Date of Patent: Feb. 28, 2023

(54) OXAZOLIDINONE ANTIBIOTIC COMPOUNDS AND PROCESS OF PREPARATION

(71) Applicant: Bugworks Research, Inc., Wilmington, DE (US)

(72) Inventors: Shahul Hameed Peer Mohamed, Whitefield Bengaluru (IN); Nagakumar Bharatham, Whitefield Bengaluru (IN); Nainesh Katagihallimath, Whitefield Bengaluru (IN); Sreevalli Sharma, Whitefield Bengaluru (IN); Radha Nandishaiah, Whitefield Bengaluru (IN); Vasanthi Ramachandran, Whitefield Bengaluru (IN)

(73) Assignee: BUGWORKS RESEARCH, INC., Wilmington, DE (US)

( * ) Notice: Subject to any disclaimer, the term of this patent is extended or adjusted under 35 U.S.C. 154(b) by 57 days.

(21) Appl. No.: 17/041,203

(22) PCT Filed: Mar. 28, 2019

(86) PCT No.: PCT/IN2019/050252
§ 371 (c)(1),
(2) Date: Sep. 24, 2020

(87) PCT Pub. No.: WO2019/186590
PCT Pub. Date: Oct. 3, 2019

(65) Prior Publication Data
US 2021/0008078 A1  Jan. 14, 2021

(30) Foreign Application Priority Data
Mar. 28, 2018 (IN) .............................. 201841011765

(51) Int. Cl.
*A61K 31/542* (2006.01)
*A61P 31/04* (2006.01)
*A61K 31/5383* (2006.01)
*C07D 519/00* (2006.01)

(52) U.S. Cl.
CPC ........ *A61K 31/542* (2013.01); *A61K 31/5383* (2013.01); *A61P 31/04* (2018.01); *C07D 519/00* (2013.01)

(58) Field of Classification Search
CPC ............... C07D 519/00; A61K 31/542; A61K 31/5383; A61P 31/04

USPC ....................................................... 514/224.2
See application file for complete search history.

(56) References Cited

FOREIGN PATENT DOCUMENTS

| WO | 2008126024 A2 | 10/2008 | |
|---|---|---|---|
| WO | WO-2009104159 A1 * | 8/2009 | ........... C07D 413/14 |
| WO | 2013021363 A1 | 2/2013 | |
| WO | 2017199265 A1 | 11/2017 | |

OTHER PUBLICATIONS

Examination Report dated Mar. 5, 2020 in IN Application No. 201841011765.
International Search Report dated Jun. 21, 2019 in International Application No. PCT/IN2019/050252.
Office Action dated May 10, 2022 in EP Application No. 19721148.5.
Remington, J. P., "The Science and Practice of Pharmacy," 21st Edition, 2419 pages (2005).
Smith et al., March's Advanced Organic Chemistry: Reactions, Mechanisms, and Structure, Sixth Edition, 2374 pages (2007).
Wuts et al., Greene's Protective Groups in Organic Synthesis, Fourth Edition, 1111 pages (2007).

* cited by examiner

*Primary Examiner* — Kahsay Habte
(74) *Attorney, Agent, or Firm* — Panitch Schwarze Belisario & Nadel LLP

(57) ABSTRACT

Compounds of Formula I, its stereoisomers, pharmaceutically acceptable salts, complexes, hydrates, solvates, tautomers, polymorphs, racemic mixtures, optically active forms and pharmaceutically active derivative thereof and pharmaceutical compositions containing them as the active ingredient which can be used as medicaments are provided. The aforementioned substances can also be used in the manufacture of medicaments for treatment, prevention, or suppression of diseases, and conditions mediated by microbes. Methods for the synthesis and characterization of the aforementioned substances are also provided.

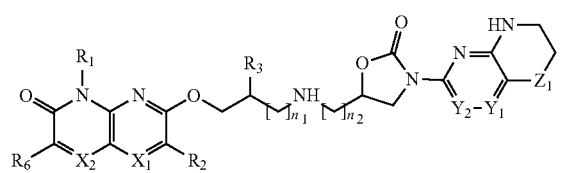

Formula I

15 Claims, No Drawings

OXAZOLIDINONE ANTIBIOTIC COMPOUNDS AND PROCESS OF PREPARATION

CROSS-REFERENCE TO RELATED APPLICATIONS

This application is a Section 371 of International Application No. PCT/IN2019/050252, filed Mar. 28, 2019, which was published in the English language on Oct. 3, 2019 under International Publication No. WO 2019/186590 A1, which claims priority under 35 U.S.C. § 119(b) to Indian Application No. 201841011765, filed on Mar. 28, 2018, the disclosures of which are incorporated herein by reference in their entireties.

FIELD OF INVENTION

The present disclosure relates to the field of medicinal chemistry and more particularly to the development of antimicrobial compounds effective against bacteria, virus, fungi, and protozoa including a spectrum of Gram-negative and Gram-positive pathogens. The present disclosure relates to compounds of Formula I, its stereoisomers, pharmaceutically acceptable salts, complexes, hydrates, solvates, tautomers, polymorphs, racemic mixtures, optically active forms and pharmaceutically active derivative thereof and pharmaceutical compositions containing them as the active ingredient. The present disclosure further relates to the synthesis and characterization of aforementioned compounds to exhibit high antimicrobial activity.

The compounds of the present disclosure are useful as medicaments and their use in the manufacture of medicaments for treatment, prevention or suppression of diseases, and conditions mediated by microbes. The present disclosure also provides evidence for treating infection caused by microbes.

BACKGROUND

The rise of drug-resistant bacteria is a growing threat to modern medicine with the advent of infections resistant to even last-resort antibiotics. The situation has become worse in recent years by overuse of antibiotics and cutbacks in drug research. In general, bacterial pathogens may be classified as either Gram-positive or Gram-negative pathogens.

Antibiotic compounds with effective activity against both Gram-positive and Gram-negative pathogens are regarded as having a broad spectrum of activity. Current antibacterial drugs used to treat and prevent bacterial infections have been found to have limited effect. Further, there is a continuing need to identify new compounds with potent antibacterial activity with reduced potential for developing resistance, which possess improved efficacy against bacterial infections that resist treatment with currently available antibiotics, or which possess selectivity against target microorganisms.

From the foregoing, it is clear that compounds used in the state of the art to treat and prevent bacterial infection have been found to have limited effect. Further, there is a continuing need to identify new compounds with improved antibacterial activity, which have less potential for developing resistance, which possess improved effectiveness against bacterial infections that resist treatment with currently available antibiotics, or which possess unexpected selectivity against target microorganisms.

SUMMARY

The present disclosure is based on the surprising discovery that compounds of Formula I (see below) exhibit advantageous antimicrobial properties. Thus, the present disclosure provides a compound of Formula I

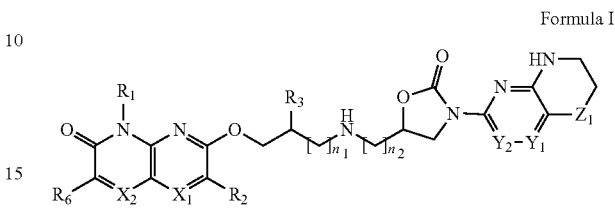

Formula I or its stereoisomers, pharmaceutically acceptable salts, complexes, hydrates, solvates, tautomers, polymorphs, racemic mixtures, optically active forms, and pharmaceutically active derivative thereof, wherein wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with up to three heteroatoms independently selected from O, N, or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxy, $SO_3H$, O—$PO_3H_2$, $COOR_8$, $CONHR_8$, $SO_2NHR_8$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with up to three heteroatoms independently selected from O, N, or S;

$R_8$ is selected from hydrogen, or $C_{1-6}$ alkyl;

$R_2$ is selected from hydrogen, halogen, hydroxyl, cyano, $C_{1-6}$ alkoxy, $C_{1-6}$ haloalkyl, $C_{1-6}$ haloalkoxy, or $C_{1-6}$ alkyl;

$R_3$ is selected from hydrogen, fluoro, $C_{1-4}$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$n_1$ is 0 or 1; $n_2$ is 1 or 2;

$R_6$ is selected from hydrogen, $C_{1-6}$ alkoxy, or $C_{1-6}$ alkyl;

$Y_1$, and $Y_2$ are independently selected from N, or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl;

$Z_1$ is selected from O, S, NH, or $CH_2$.

The present disclosure further relates to a compound of Formula I or its stereoisomers, pharmaceutically acceptable salts, complexes, hydrates, solvates, tautomers, polymorphs, racemic mixtures, optically active forms and pharmaceutically active derivative thereof, for use in killing or inhibiting the growth of a microorganism selected from the group consisting of bacteria, virus, fungi, and protozoa.

The present disclosure further relates to use of a compound of Formula I or its stereoisomers, pharmaceutically acceptable salts, complexes, hydrates, solvates, tautomers, polymorphs, racemic mixtures, optically active forms and pharmaceutically active derivative thereof, in killing or inhibiting the growth of a microorganism selected from the group consisting of bacteria, virus, fungi and protozoa.

The present disclosure further relates to a compound of Formula I or its stereoisomers, pharmaceutically acceptable salts, complexes, hydrates, solvates, tautomers, polymorphs, racemic mixtures, optically active forms and pharmaceutically active derivative thereof, for use in treating a disease or condition in a patient wherein said disease or condition is caused by a microorganism selected from the group consisting of Gram positive, and Gram negative pathogens.

The present disclosure further relates to use of a compound of Formula I or its stereoisomers, pharmaceutically acceptable salts, complexes, hydrates, solvates, tautomers, polymorphs, racemic mixtures, optically active forms and pharmaceutically active derivative thereof, in treating disease or condition in a patient, wherein said disease or condition is caused by a microorganism selected from the group consisting of Gram positive, and Gram negative pathogens. The patient is typically a mammal, preferably a human.

The present disclosure further relates to a method of treating a bacterial infection or condition in a subject, said method comprising administering to a subject a compound of Formula I, or its stereoisomers, pharmaceutically acceptable salts, complexes, hydrates, solvates, tautomers, polymorphs, racemic mixtures, optically active forms and pharmaceutically active derivative thereof, wherein said bacterial infection or condition is caused by a microorganism selected from the group consisting of Gram positive, and Gram negative pathogens.

The present disclosure relates to a composition comprising a compound of Formula I or its stereoisomers, pharmaceutically acceptable salts, complexes, hydrates, solvates, tautomers, polymorphs, racemic mixtures, optically active forms, and pharmaceutically active derivative thereof together with a carrier.

The present disclosure relates to a pharmaceutical composition comprising a compound of Formula I or its stereoisomers, pharmaceutically acceptable salts, complexes, hydrates, solvates, tautomers, polymorphs, racemic mixtures, optically active forms, and pharmaceutically active derivative thereof, together with a pharmaceutically acceptable carrier, optionally in combination with one or more other pharmaceutical compositions.

The present disclosure relates to a process of preparation of compound of Formula I or its stereoisomers, pharmaceutically acceptable salts, complexes, hydrates, solvates, tautomers, polymorphs, racemic mixtures, optically active forms, and pharmaceutically active derivative thereof.

The present disclosure relates to a process of preparation of a composition comprising a compound of Formula I or its stereoisomers, pharmaceutically acceptable salts, complexes, hydrates, solvates, tautomers, polymorphs, racemic mixtures, optically active forms, and pharmaceutically active derivative thereof together with a carrier.

The present disclosure relates to a process of preparation of pharmaceutical composition comprising a compound of Formula I or its stereoisomers, pharmaceutically acceptable salts, complexes, hydrates, solvates, tautomers, polymorphs, racemic mixtures, optically active forms, and pharmaceutically active derivative thereof, together with a pharmaceutically acceptable carrier, optionally in combination with one or more other pharmaceutical compositions.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

In this specification, the prefix $C_{x-y}$ as used in terms such as $C_{x-y}$alkyl and the like (where x and y are integers) indicates the numerical range of carbon atoms that are present in the group; for example, $C_{1-6}$alkyl includes $C_1$alkyl (methyl), $C_2$alkyl (ethyl), $C_3$alkyl (propyl and isopropyl) and $C_4$alkyl (butyl, 1-methylpropyl, 2-methylpropyl, and t-butyl). Unless specifically stated, the bonding atom of a group may be any suitable atom of that group; for example, propyl includes prop-1-yl and prop-2-yl.

The term "alkyl" refers to a monoradical branched or unbranched saturated hydrocarbon chain having from 1 to 6 carbon atoms. This term is exemplified by groups such as n-butyl, iso-butyl, t-butyl, n-hexyl, and the like. The groups may be optionally substituted.

The term "haloalkyl" as used herein refers to an alkyl group in which one or more hydrogen atoms are replaced by the same number of identical or different halogen atoms. The term "haloalkyl" is exemplified by groups such as chloromethyl, trifluoromethyl, 1-fluoroethyl, 2,2,2-trifluoroethyl, and the like.

The term "alkylene" refers to a diradical branched or unbranched saturated hydrocarbon chain having from 1 to 6 carbon atoms. This term is exemplified by groups such as methylene, ethylene, propylene, butylene, hexylene, and the like. The groups may be optionally substituted. Representative substituted alkylene groups include hydroxyl substituted alkylenes.

The term "alkenyl" refers to a monoradical of a branched or unbranched unsaturated hydrocarbon group preferably having from 2, 3, 4, 5, or 6 carbon atoms and having 1, 2, or 3, double bond (vinyl), preferably 1 double bond. The groups may be optionally substituted.

The term "cycloalkyl" refers to carbocyclic groups of from 3 to 6 carbon atoms having a single cyclic ring or multiple condensed rings which may be partially unsaturated. Such cycloalkyl groups include, by way of example, single ring structures such as cyclopropyl, cyclobutyl, cyclopentyl, cyclopentenyl, cyclohexyl, cyclohexenyl, and the like, or multiple ring structures or carbocyclic groups to which is fused an aryl group, for example indane, and the like. The groups may be optionally substituted.

The terms "alkoxyl" or "alkoxy" refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl.

"Halo" or "Halogen", alone or in combination with any other term means halogens such as chloro (Cl), fluoro (F), bromo (Br) and iodo (I).

The term "carbocyclyl" or "carbocycle" refers to a saturated, unsaturated ring having 4 to 7 carbon atoms as a monocycle. Representative carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocyclyl" refers to a "carbocyclyl" as defined herein, wherein one or more carbon atoms have been replaced with a heteroatom selected from O, N, or S.

The term "haloalkyl" refers to an alkyl group as defined above attached via halo linkage to the rest of the molecule. For example, $C_{1-6}$ haloalkyl refers to an alkyl group having from 1-6 carbon atoms, or 1-4 carbon atoms attached via halo linkage to the rest of the molecule. Preferred haloalkyl groups include, without limitation, —$CH_2Cl$, —$CHCl_2$, and the like.

The term "haloalkoxy" refers to an alkoxy group as defined above further attached via halo linkage. For example, $C_{1-6}$ haloalkoxy refers to an alkoxy group having from 1-6 carbon atoms, or 1-3 carbon atoms further attached via halo linkage. Preferred haloalkoxy groups include, without limitation, —$OCH_2Cl$, —$OCHCl_2$, and the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

The term "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, the route of administration, and like factors within the knowledge and expertise of the attending physician.

The compounds described herein may contain one or more chiral centers and/or double bonds and therefore, may exist as stereoisomers, such as double-bond isomers (i.e., geometric isomers), regioisomers, enantiomers or diastereomers.

Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form, and mixtures thereof. Accordingly, the chemical structures depicted herein encompass all possible tautomeric forms of the illustrated or identified compounds.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

The compounds discussed herein in many instances may have been named and/or checked with ACD/Name by ACD/Labs® and/or Chemdraw by CambridgeSoft®.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

Salts and solvates having non-pharmaceutically acceptable counter-ions or associated solvents are within the scope of the present disclosure, for example, for use as intermediates in the preparation of other compounds of Formula I, and their pharmaceutically acceptable salts. Thus, one embodiment of the disclosure embraces compounds of Formula I, and salts thereof. Compounds according to and Formula I contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenyl acetate, propionate, butyrate, iso-butyrate, valerate, maleate, hydroxymaleate, acrylate, fumarate, malate, tartrate, citrate, salicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), aminobenzenesulfonate, p-toluenesulfonate (tosylate), and naphthalene-2-sulfonate.

The term "solvate", as used herein, refers to a crystal form of a substance which contains solvent.

The term "complexes" as used herein, can be interchangeably used as "coordination complex," or "metal coordination complex," and the like. It refers to a complex of an organic compound with a metal that can be empirically differentiated from a simple metal salt of the organic compound based on physiochemical and/or spectroscopic properties, with a coordination complex typically having enhanced covalency as compared to a salt. Without limitation "complexes" as used herein also involves a combination of coordinate covalent bonds and/or ionic bonds. As used herein, the term "complexes" also includes molecules that lack an ionic component (e.g., such as a neutral coordination complex prior to deprotonation, where pKa of the coordination complex falls within a physiologically acceptable range).

The term "hydrate" refers to a solvate wherein the solvent is water.

A term once described, the same meaning applies for it, throughout the disclosure.

As discussed in the background section, the identification and development of new compounds with improved antibacterial activity, having less potential for developing resistance, improved effectiveness against bacterial infections would open new opportunities in the realm of currently available antibiotics.

The present disclosure relates to a compound of Formula I

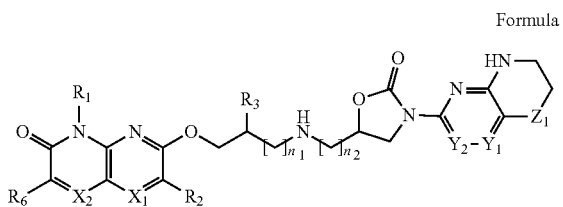

Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with up to three heteroatoms independently selected from O, N, or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxy, $SO_3H$, $O-PO_3H_2$, $COOR_8$, $CONHR_8$, $SO_2NHR_8$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with up to three heteroatoms independently selected from O, N, or S;

$R_8$ is selected from hydrogen, or $C_{1-6}$ alkyl;

$R_2$ is selected from hydrogen, halogen, cyano, hydroxyl, $C_{1-6}$ alkoxy, $C_{1-6}$ haloalkyl, $C_{1-6}$ haloalkoxy, or $C_{1-6}$ alkyl;

$R_3$ is selected from hydrogen, fluoro, $C_{1-4}$ alkoxy, hydroxyl, or amino;

$X_1$ is N or $CR_4$; $R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$; $R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$n_1$ is 0 or 1;

$n_2$ is 1 or 2;

$R_6$ is selected from hydrogen, $C_{1-6}$ alkoxy, or $C_{1-6}$ alkyl;

$Y_1$, and $Y_2$ are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N, or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxy, $SO_3H$, $O-PO_3H_2$, $COOR_8$, $CONHR_8$, $SO_2NHR$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N, or S;

$R_8$ is selected from hydrogen, or $C_{1-6}$ alkyl;

$R_2$ is selected from hydrogen, halogen, cyano, hydroxyl, $C_{1-6}$ alkoxy, $C_{1-6}$ haloalkyl, or $C_{1-6}$ alkyl;

$R_3$ is selected from hydrogen, fluoro, $C_{1-4}$ alkoxy, hydroxyl, or amino;

$X_1$ is N or $CR_4$; $R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$; $R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$n_1$ is 0 or 1;

$n_2$ is 1 or 2;

$R_6$ is selected from hydrogen, $C_{1-6}$ alkoxy, or $C_{1-6}$ alkyl;

$Y_1$, and $Y_2$ are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N, or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxy, $SO_3H$, $O—PO_3H_2$, $COOR_8$, $CONHR_8$, $SO_2NHR$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N, or S;

$R_8$ is selected from hydrogen, or $C_{1-6}$ alkyl;

$R_2$ is selected from hydrogen, halogen, cyano, hydroxyl, $C_{1-6}$ alkoxy, $C_{1-6}$ haloalkoxy, or $C_{1-6}$ alkyl;

$R_3$ is selected from hydrogen, fluoro, $C_{1-4}$ alkoxy, hydroxyl, or amino;

$X_1$ is N or $CR_4$; $R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$; $R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$n_1$ is 0 or 1;

$n_2$ is 1 or 2;

$R_6$ is selected from hydrogen, $C_{1-6}$ alkoxy, or $C_{1-6}$ alkyl;

$Y_1$, and $Y_2$ are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl;

Z1 is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N, or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxy, $SO_3H$, $O—PO_3H_2$, $COOR_8$, $CONHR_8$, $SO_2NHR$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N, or S;

$R_8$ is selected from hydrogen, or $C_{1-6}$ alkyl;

$R_2$ is selected from hydrogen, fluoro, chloro, cyano, hydroxyl, $C_{1-6}$ alkoxy, $C_{1-6}$ haloalkyl, $C_{1-6}$ haloalkoxy, or $C_{1-6}$ alkyl;

$R_3$ is selected from hydrogen, fluoro, $C_{1-4}$ alkoxy, hydroxyl, or amino;

$X_1$ is N or $CR_4$; $R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$; $R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$n_1$ is 0 or 1;

$n_2$ is 1 or 2;

$R_6$ is selected from hydrogen, $C_{1-6}$ alkoxy, or $C_{1-6}$ alkyl;

$Y_1$, and $Y_2$ are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl;

$Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N, or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxy, $SO_3H$, $O—PO_3H_2$, $COOR_8$, $CONHR_8$, $SO_2NHR$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ aminocycloalkyl, $C_{3-6}$ cycloalkylhydroxy, $C_{1-6}$ alkylamino, or 3-7 membered saturated or unsaturated heterocyclyl ring optionally substituted with upto three heteroatoms independently selected from O, N, or S;

$R_8$ is selected from hydrogen, or $C_{1-6}$ alkyl;

$R_2$ is selected from hydrogen, fluoro, chloro, cyano, hydroxyl, $C_{1-6}$ alkoxy, $C_{1-4}$ haloalkyl, $C_{1-6}$ haloalkoxy, or $C_{1-6}$ alkyl;

$R_3$ is selected from hydrogen, fluoro, $C_{1-4}$ alkoxy, hydroxyl, or amino;

$X_1$ is N or $CR_4$; $R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$; $R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$n_1$ is 0 or 1;

$n_2$ is 1 or 2;

$R_6$ is selected from hydrogen, $C_{1-6}$ alkoxy, or $C_{1-6}$ alkyl;

$Y_1$, and $Y_2$ are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl;

$Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N, or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_8$, $CONHR_8$, $SO_2NHR$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ cycloalkylhydroxy, $C_{3-6}$ aminocycloalkyl, $C_{1-6}$ alkylamino, or 3-7 membered saturated or unsaturated heterocyclyl ring optionally substituted with upto three heteroatoms independently selected from O, N, or S;

$R_8$ is selected from hydrogen, or $C_{1-6}$ alkyl;

$R_2$ is selected from hydrogen, fluoro, chloro, $C_{1-4}$ alkoxy, cyano, hydroxyl, or $C_1$-alkyl;

$R_3$ is selected from hydrogen, fluoro, $C_{1-4}$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, or $C_{1-6}$ alkyl;

$n_1$ is 0 or 1; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, or 4-7 membered saturated or unsaturated carbocyclyl or heterocyclyl ring, wherein the heterocyclyl ring is optionally substituted with upto three heteroatoms independently selected from O, N, or S, wherein $C_{1-6}$ alkyl, $C_{2-6}$ alkenyl, $C_{3-6}$ cycloalkyl, $C_{1-6}$ alkylamino, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_8$, $CONHR_8$, $SO_2NHR_8$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ cycloalkylhydroxy, $C_{3-6}$ aminocycloalkyl, $C_{1-6}$ alkylamino, or 3-7 membered saturated or unsaturated heterocyclyl ring optionally substituted with upto three heteroatoms independently selected from O, N, or S;

$R_8$ is selected from hydrogen, or $C_{1-6}$ alkyl;

$R_2$ is selected from hydrogen, fluoro, chloro, $C_{1-4}$ alkoxy, cyano, hydroxyl, or $C_1$-alkyl;

$R_3$ is selected from hydrogen, fluoro, $C_{1-4}$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, and/or $C_{1-6}$ alkyl;

$n_1$ is 0 or 1; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or$_{1-6}$ alkyl; and $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-4}$ alkyl, $C_{2-4}$ alkenyl, $C_{3-5}$ cycloalkyl, $C_{1-4}$ alkylamino, or 4-7 membered saturated or unsaturated carbocyclyl or heterocyclyl ring, wherein the heterocyclyl ring is optionally substituted with upto three heteroatoms independently selected from O, N, or S, wherein $C_{1-4}$ alkyl, $C_{2-4}$ alkenyl, $C_{3-5}$ cycloalkyl, $C_{1-4}$ alkylamino, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_8$, $CONHR_8$, $SO_2NHR_8$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ cycloalkylhydroxy, $C_{3-6}$ aminocycloalkyl, $C_{1-6}$ alkylamino, or 3-7 membered saturated or unsaturated heterocyclyl ring optionally substituted with upto three heteroatoms independently selected from O, N, or S;

$R_8$ is selected from hydrogen, or $C_{1-6}$ alkyl;

$R_2$ is selected from hydrogen, fluoro, chloro, $C_{1-4}$ alkoxy, cyano, hydroxyl, or $C_1$-alkyl;

$R_3$ is selected from hydrogen, fluoro, $C_{1-4}$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, or $C_{1-6}$ alkyl;

$n_1$ is 0 or 1; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-4}$ alkyl, $C_{2-4}$ alkenyl, $C_{3-5}$ cycloalkyl, $C_{1-4}$ alkylamino, or 4-7 membered saturated or unsaturated carbocyclyl or heterocyclyl ring, wherein the heterocyclyl ring is optionally substituted with upto three heteroatoms independently selected from O, N, or S, wherein $C_{1-4}$ alkyl, $C_{2-4}$ alkenyl, $C_{3-5}$ cycloalkyl, $C_{1-4}$ alkylamino, or 4-7 membered saturated or unsaturated carbocyclyl or heterocyclyl ring are optionally substituted with 1 to 3 groups independently selected from halogen, amino, hydroxyl, $0-PO_3H_2$, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_3$-6 cycloalkylhydroxy, $C_{3-6}$ aminocycloalkyl, $C_{1-6}$ alkylamino, or 3-7 membered saturated or unsaturated heterocyclyl ring optionally substituted with upto three heteroatoms independently selected from O, N, or S;

$R_2$ is selected from hydrogen, fluoro, chloro, $C_{1-2}$ alkoxy, cyano, hydroxyl, or $C_1$ alkyl;

$R_3$ is selected from hydrogen, fluoro, $C_{1-4}$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, or $C_{1-6}$ alkyl;

$n_1$ is 0 or 1; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, or 4-7 membered saturated or unsaturated carbocyclyl or heterocyclyl ring, wherein the heterocyclyl ring is optionally substituted with upto three heteroatoms independently selected from O, N, or S, wherein $C_{1-6}$ alkyl, $C_{2-6}$ alkenyl, $C_{3-6}$ cycloalkyl, $C_{1-6}$ alkylamino, and 4-7 membered saturated or unsaturated carbocyclyl or heterocyclyl ring are optionally substituted with 1 to 3 groups independently selected from halogen, amino, hydroxyl, $0-PO_3H_2$, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_3$-6 cycloalkylhydroxy, $C_{3-6}$ aminocycloalkyl, $C_{1-6}$ alkylamino, or 3-7 membered saturated or unsaturated heterocyclyl ring optionally substituted with upto three heteroatoms independently selected from O, N, or S;

$R_2$ is selected from hydrogen, fluoro, chloro, $C_1$ alkoxy, cyano, hydroxyl, or $C_1$-alkyl;

$R_3$ is selected from hydrogen, fluoro, $C_1$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, or $C_1$ alkyl;

$n_1$ is 0 or 1; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-4}$ alkyl, $C_{2-6}$ alkenyl, $C_{3-4}$ cycloalkyl, $C_{1-4}$ alkylamino, or 4-7 membered saturated carbocyclyl or heterocyclyl ring, wherein the heterocyclyl ring is optionally substituted with upto three heteroatoms independently selected from O, N, or S, wherein $C_{1-4}$ alkyl, $C_{1-4}$ haloalkyl, $C_{3-5}$ cycloalkyl, $C_{1-4}$ alkylamino, and 4-7 membered saturated carbocyclyl or heterocyclyl ring are optionally substituted with 1 to 3 groups independently selected from halogen, amino, hydroxyl, $O-PO_3H_2$, $C_{1-4}$ alkyl, $C_{1-4}$ alkoxy, $C_{1-4}$ haloalkoxy, $C_{3-5}$ cycloalkyl, $C_{3-5}$ cycloalkylamino, $C_{3-5}$ cycloalkylhydroxy, $C_3$-aminocycloalkyl, $C_{1-4}$ alkylamino, or 3-7 membered saturated or unsaturated heterocyclyl ring optionally substituted with upto three heteroatoms independently selected from O, N, or S;

$R_2$ is selected from hydrogen, fluoro, chloro, $C_1$ alkoxy, cyano, hydroxyl or $C_1$-alkyl;

$R_3$ is selected from hydrogen, fluoro, $C_1$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, or $C_1$ alkyl $n_1$ is 0 or 1; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-3}$ alkyl, $C_{2-6}$ alkenyl, $C_{3-4}$ cycloalkyl, $C_{1-4}$ alkylamino, or 4-6 membered saturated carbocyclyl or heterocyclyl ring, wherein the heterocyclyl ring is optionally substituted with upto two heteroatoms independently selected from O, or N, wherein $C_{1-3}$ alkyl, $C_{2-6}$ alkenyl, $C_{3-4}$ cycloalkyl, $C_{1-4}$ alkylamino, and 4-6 membered saturated carbocyclyl or heterocyclyl ring are optionally substituted with 1 to 3 groups independently selected from halogen, amino, hydroxyl, $C_{1-4}$ alkyl, $C_{1-4}$ alkoxy, $C_{1-4}$ haloalkoxy, $C_{3-5}$ cycloalkyl, $C_{3-5}$ cycloalkylamino, $C_{3-5}$ cycloalkylhydroxy, $C_{3-5}$ aminocycloalkyl, $C_{1-4}$ alkylamino, or 3-6 membered saturated or unsaturated heterocyclyl ring optionally substituted with upto three heteroatoms independently selected from O, or N;

$R_2$ is selected from hydrogen, fluoro, chloro, $C_1$ alkoxy, cyano, hydroxyl, or $C_1$-alkyl;

$R_3$ is selected from hydrogen, fluoro, $C_1$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, or $C_1$ alkyl $n_1$ is 0 or 1; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-3}$ alkyl, $C_{2-6}$ alkenyl, $C_{3-4}$ cycloalkyl, $C_{1-4}$ alkylamino, or 4-6 membered saturated carbocyclyl or heterocyclyl ring, wherein the heterocyclyl ring is optionally substituted with upto two heteroatoms independently selected from O, or N, wherein $C_{1-3}$ alkyl, $C_{2-6}$ alkenyl, $C_{3-4}$ cycloalkyl, $C_{1-4}$ alkylamino, and 4-6 membered saturated carbocyclyl or heterocyclyl ring are optionally substituted with 1 to 3 groups independently selected from halogen, amino, hydroxyl, $C_{1-4}$ alkyl, $C_{1-4}$ alkoxy, $C_{1-4}$ haloalkoxy, $C_{3-5}$ cycloalkyl, $C_{3-5}$ cycloalkylamino, $C_{3-5}$ cycloalkylhydroxy, $C_{3-5}$ aminocycloalkyl, $C_{1-4}$ alkylamino, or 3-6 membered saturated or unsaturated heterocyclyl ring optionally substituted with upto three heteroatoms independently selected from O, or N;

$R_2$ is selected from hydrogen, fluoro, chloro, $C_1$ alkoxy, cyano, hydroxyl, or $C_1$ alkyl;

$R_3$ is selected from hydrogen, fluoro, $C_1$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, or $C_1$ alkyl $n_1$ is 0; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-3}$ alkyl, $C_{2-6}$ alkenyl, $C_{3-4}$ cycloalkyl, $C_{1-4}$ alkylamino, or 4-6 membered saturated carbocyclyl or heterocyclyl ring, wherein the heterocyclyl ring is optionally substituted with upto two heteroatoms independently selected from O, or N, wherein $C_{1-3}$ alkyl, $C_{2-6}$ alkenyl, $C_{3-4}$ cycloalkyl, $C_{1-4}$ alkylamino, and 4-6 membered saturated carbocyclyl or heterocyclyl ring are optionally substituted with 1 to 3 groups independently selected from halogen, amino, hydroxyl, $C_{1-4}$ alkyl, $C_{1-4}$ alkoxy, $C_3$-cycloalkyl, $C_{3-5}$ cycloalkylamino, $C_{3-5}$ cycloalkylhydroxy, $C_{3-5}$ aminocycloalkyl, $C_{1-4}$ alkylamino, or 3-6 membered saturated or unsaturated heterocyclyl ring optionally substituted with upto three heteroatoms independently selected from O, or N;

$R_2$ is selected from hydrogen, fluoro, $C_1$ alkoxy, cyano, hydroxyl, or $C_1$ alkyl;

$R_3$ is selected from hydrogen, fluoro, $C_1$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, or $C_1$ alkyl $n_1$ is 0; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH_2OCH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

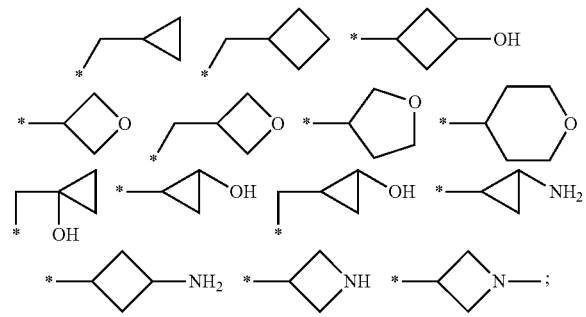

$R_2$ is selected from hydrogen, fluoro, chloro, $C_1$ alkoxy, cyano, hydroxyl, or $C_1$-alkyl;

$R_3$ is selected from hydrogen, fluoro, $C_1$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, or $C_1$ alkyl $n_1$ is 0 or 1; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH_2OCH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

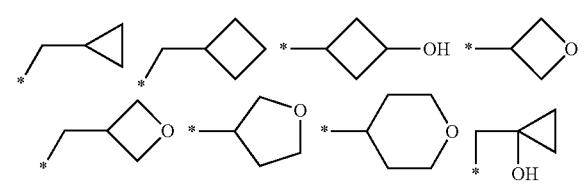

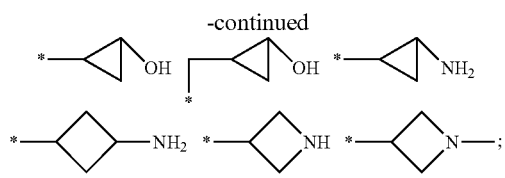

$R_2$ is selected from hydrogen, fluoro, chloro, methoxy, methyl, cyano or hydroxyl;

$R_3$ is selected from hydrogen, fluoro, methoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, COOH, $CH_2COOH$, $CH_2OH$, $CH_2NH_2$, $CH(CH_3)NH_2$, $CH_2NHCH_3$, $CH_2NHCH_2CH_2OH$, $C_{1-6}$ alkoxy, $C_{1-6}$ haloalkoxy, or $C_{1-6}$ alkyl;

$R_6$ is selected from hydrogen, or $C_1$ alkyl;

$n_1$ is 0 or 1; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is independently selected from the group consisting of $CH_3$, $CH_2CH_3$, $CH_2OCH_3$, $CH(CH_3)_2$, cyclopropyl, $CH_2CH(OH)CH_3$, $CH_2CH_2OH$, $CH_2CH_2OCH_3$, $CH_2CH_2NH_2$, $CH_2CH_2NHCH_3$, $CH_2CH(NH_2)CH_3$, $CH_2CH_2N(CH_3)_2$,

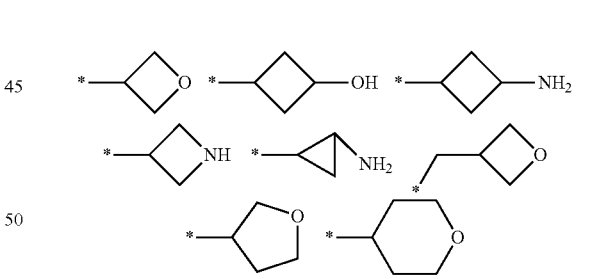

$R_2$ is selected from hydrogen, fluoro, chloro, methoxy, methyl, cyano or hydroxyl;

$R_3$ is selected from hydrogen, fluoro, methoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, COOH, $CH_2COOH$, $CH_2OH$, $CH_2NH_2$, $CH(CH_3)NH_2$, $CH_2NHCH_3$, $CH_2NHCH_2CH_2OH$, $C_{1-6}$ alkoxy, $C_{1-6}$ haloalkoxy, or $C_{1-6}$ alkyl;

$R_6$ is selected from hydrogen, or $C_1$ alkyl;
$n_1$ is 0 or 1; $n_2$ is 1 or 2;
$Y_1$, and $Y_2$ are independently selected from N or $CR_7$;
$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and
$Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein
$R_1$ is independently selected from the group consisting of $CH_3$, $CH_2CH_3$, $CH_2OCH_3$, $CH(CH_3)_2$, cyclopropyl, $CH_2CH(OH)CH_3$, $CH_2CH_2OH$, $CH_2CH_2OCH_3$, $CH_2CH_2NH_2$, $CH_2CH_2NHCH_3$, $CH_2CH(NH_2)CH_3$, $CH_2CH_2N(CH_3)_2$,

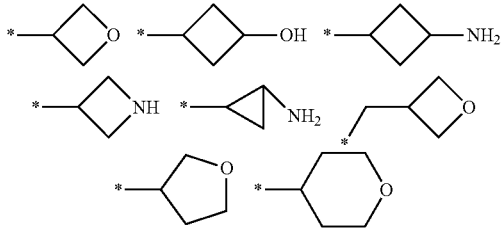

$R_2$ is selected from hydrogen, fluoro, chloro, cyano, or hydroxyl;
$R_3$ is selected from hydrogen, fluoro, or amino;
$X_1$ is N or $CR_4$;
$R_4$ is selected from hydrogen, $C_{1-6}$ haloalkyl, $C_{1-6}$ haloalkoxy, or $C_{1-6}$ alkyl;
$X_2$ is N or $CR_5$;
$R_5$ is selected from hydrogen, cyano, COOH, $CH_2NH_2$, $CH(CH_3)NH_2$, $CH_2NHCH_3$, $CH_2NHCH_2CH_2OH$, $C_{1-6}$ alkoxy, $C_{1-6}$ haloalkoxy, or $C_{1-6}$ alkyl;
$R_6$ is selected from hydrogen, or $C_1$ alkyl;
$n_1$ is 0 or 1; $n_2$ is 1 or 2;
$Y_1$, and $Y_2$ are independently selected from N or $CR_7$;
$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and
$Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein
$R_1$ is independently selected from the group consisting of $CH_3$, $CH_2CH_3$, $CH_2OCH_3$, $CH(CH_3)_2$, cyclopropyl, $CH_2CH(OH)CH_3$,

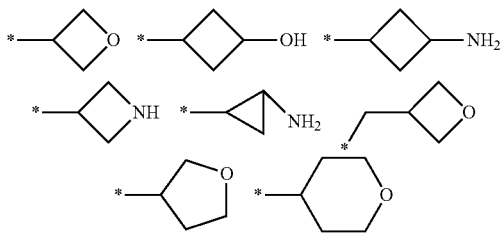

$R_2$ is selected from hydrogen, fluoro, chloro, cyano, or hydroxyl;
$R_3$ is selected from hydrogen, fluoro, or amino;
$X_1$ is N or $CR_4$;
$R_4$ is selected from hydrogen, $C_{1-6}$ haloalkyl, $C_{1-6}$ haloalkoxy, or $C_{1-6}$ alkyl;
$X_2$ is N or $CR_5$;
$R_5$ is selected from hydrogen, cyano, COOH, $CH_2NH_2$, $CH(CH_3)NH_2$, $CH_2NHCH_3$, $CH_2NHCH_2CH_2OH$, $C_{1-6}$ alkoxy, $C_{1-6}$ haloalkoxy, or $C_{1-6}$ alkyl;
$R_6$ is selected from hydrogen;
$n_1$ is 0; $n_2$ is 1 or 2;
$Y_1$, and $Y_2$ are independently selected from N or $CR_7$;
$R_7$ is selected from hydrogen, halogen, or $C_{1-6}$ alkyl; and
$Z_1$ is selected from O, S, NH, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein
$R_1$ is independently selected from the group consisting of $CH_3$, $CH_2CH_3$, $CH_2OCH_3$, $CH(CH_3)_2$, cyclopropyl, $CH_2CH(OH)CH_3$,

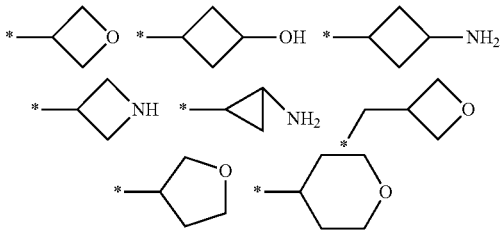

$R_2$ is selected from hydrogen, fluoro, chloro, cyano, or hydroxyl;
$R_3$ is selected from hydrogen, fluoro, or amino;
$X_1$ is N or $CR_4$;
$R_4$ is selected from hydrogen, $C_{1-6}$ haloalkyl, $C_{1-6}$ haloalkoxy, or $C_{1-6}$ alkyl;
$X_2$ is N or $CR_5$;
$R_5$ is selected from hydrogen, cyano, COOH, $CH_2NH_2$, $CH(CH_3)NH_2$, $CH_2NHCH_3$, $CH_2NHCH_2CH_2OH$, $C_{1-6}$ alkoxy, $C_{1-6}$ haloalkoxy, or $C_{1-6}$ alkyl;
$R_6$ is selected from hydrogen;
$n_1$ is 0; $n_2$ is 1 or 2;
$Y_1$, and $Y_2$ are independently selected from N or $CR_7$;
$R_7$ is selected from hydrogen, halogen, or $C_{1-6}$ alkyl; and
$Z_1$ is selected from O, S, or $CH_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein
$R_1$ is independently selected from the group consisting of $CH_3$, $CH_2CH_3$, $CH(CH_3)_2$, cyclopropyl, $CH_2OCH_3$, $CH_2CH(OH)CH_3$,

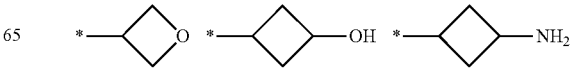

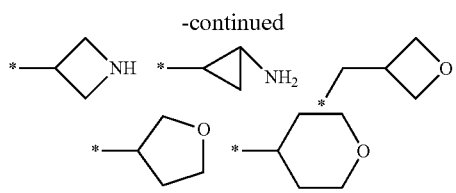

R₂ is selected from hydrogen, fluoro, chloro, cyano, or hydroxyl;
R₃ is selected from hydrogen, fluoro, or amino;
$X_1$ is N or $CR_4$;
$R_4$ is selected from hydrogen, or $C_{1-6}$ alkyl;
$X_2$ is N or $CR_5$;
$R_5$ is selected from hydrogen, or $C_{1-6}$ alkyl;
$R_6$ is selected from hydrogen;
$n_1$ is 0; $n_2$ is 1 or 2;
$Y_1$, and $Y_2$ are independently selected from N or $CR_7$;
$R_7$ is selected from hydrogen; and
$Z_1$ is selected from O, or S.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivative thereof, wherein $X_1$ is N, CH or C(CH₃).

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivative thereof, wherein, $X_2$ is N or CH.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivative thereof, wherein, $R_1$ is selected from CH₃, CH₂CH₃, CH₂CH₂OH, or CH₂OCH₃.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivative thereof, wherein, $R_2$ and $R_3$ is independently selected from hydrogen, fluoro, chloro, or hydroxy.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivative thereof, wherein $R_6$ is H.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivative thereof, wherein $Y_1$ is CH or N.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivative thereof, wherein $Y_2$ is CH.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivative thereof, wherein $Z_1$ is selected from O, or S.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivative thereof, wherein, $n_1$ is 0.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivative thereof, wherein, $n_2$ is 1 or 2.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, which is selected from a group consisting of:

(Compound 1)

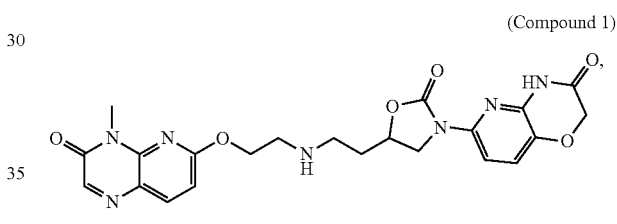

6-(5-(2-(((2-((4-methyl-3-oxo-3,5-dihydropyrido[2,3-b]pyrazin-6-yl)oxy)ethyl)amino)ethyl)-2-oxooxazolidin-3-yl)-2H-pyrido[3,2-b][1,4]oxazin-3(4H)-one (Compound 2)

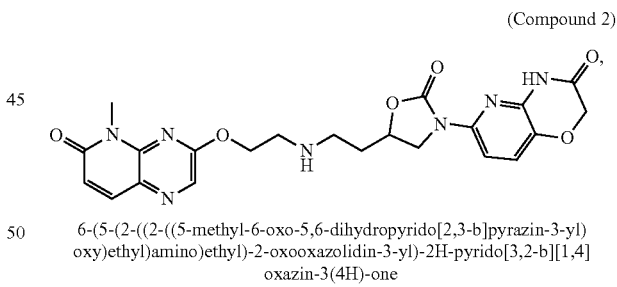

6-(5-(2-(((2-((5-methyl-6-oxo-5,6-dihydropyrido[2,3-b]pyrazin-3-yl)oxy)ethyl)amino)ethyl)-2-oxooxazolidin-3-yl)-2H-pyrido[3,2-b][1,4]oxazin-3(4H)-one (Compound 3)

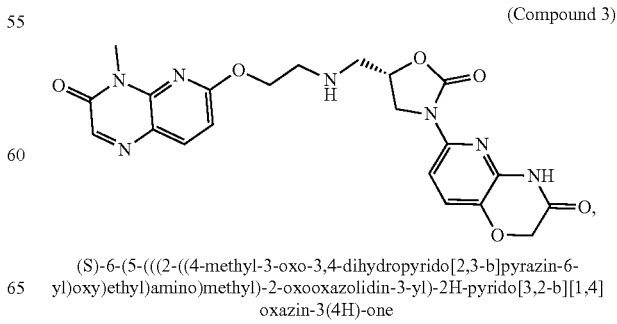

(S)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrido[3,2-b][1,4]oxazin-3(4H)-one (Compound 4)

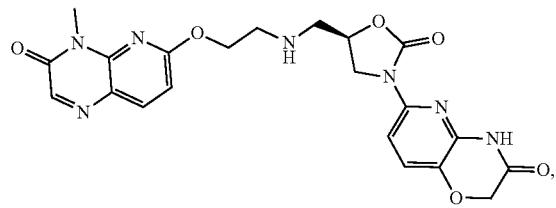

(R)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrido[3,2-b][1,4]oxazin-3(4H)-one (Compound 5)

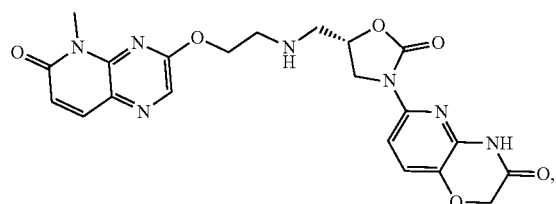

(S)-6-(5-(((2-((5-methyl-6-oxo-5,6-dihydropyrido[2,3-b]pyrazin-3-yl)oxy)ethyl)amino)methyl)-2-oxooxazolidin-3-yl)-2H-pyrido[3,2-b][1,4]oxazin-3(4H)-one (Compound 6)

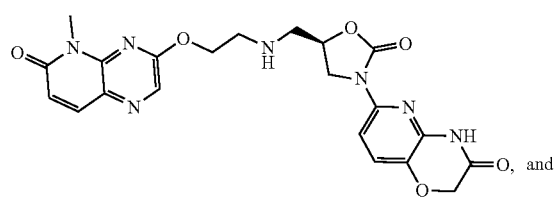

(R)-6-(5-(((2-((5-methyl-6-oxo-5,6-dihydropyrido[2,3-b]pyrazin-3-yl)oxy)ethyl)amino)methyl)-2-oxooxazolidin-3-yl)-2H-pyrido[3,2-b][1,4]oxazin-3(4H)-one (Compound 7)

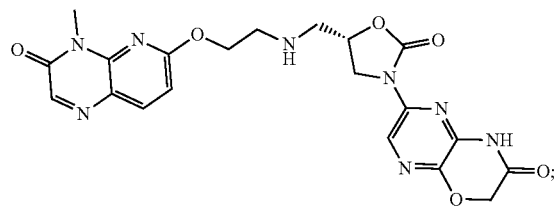

(S)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrido[3,2-b][1,4]oxazin-3(4H)-one (Compound 8)

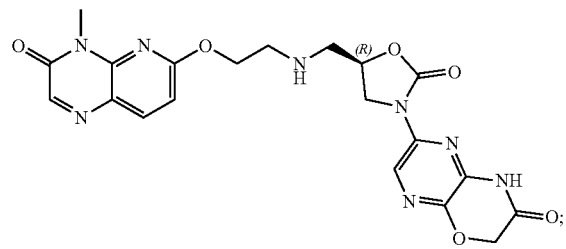

(R)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrazino[2,3-b][1,4]oxazin-3(4H)-one (Compound 9)

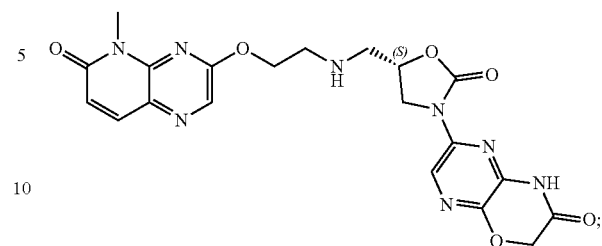

(S)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrazino[2,3-b][1,4]oxazin-3(4H)-one (Compound 10)

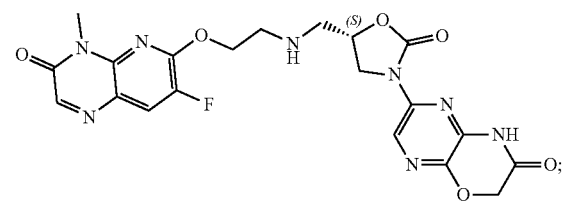

(S)-6-(5-(((2-((7-fluoro-4-methyl-3-oxo-3,4-dihydropyrido[2,3-b]pyrazin-6-yl)oxy)ethyl)amino)methyl)-2-oxooxazolidin-3-yl)-2H-pyrazino[2,3-b][1,4]oxazin-3(4H)-one (Compound 11)

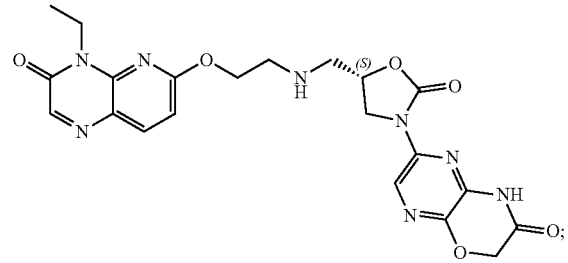

(S)-6-(5-(((2-((4-ethyl-3-oxo-3,4-dihydropyrido[2,3-b]pyrazin-6-yl)oxy)ethyl)amino)methyl)-2-oxooxazolidin-3-yl)-2H-pyrazino[2,3-b][1,4]oxazin-3(4H)-one (Compound 12)

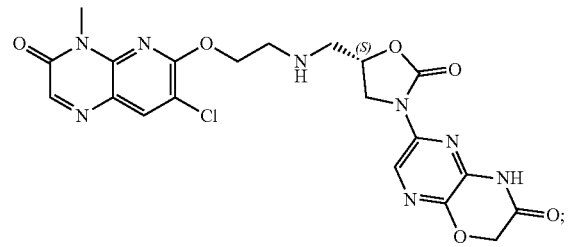

(S)-6-(5-(((2-((7-Chloro-4-methyl-3-oxo-3,4-dihydropyrido[2,3-b]pyrazin-6-yl)oxy)ethyl)amino)methyl)-2-oxooxazolidin-3-yl)-2H-pyrazino[2,3-b][1,4]oxazin-3(4H)-one -continued (Compound 13)

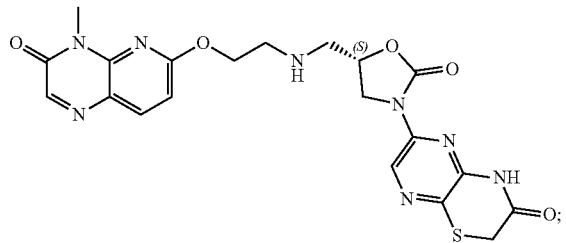

(S)-5-(((2-((4-Methyl-3-oxo-3,4-dihydropyrido[2,3-b]pyrazin-6-yl)oxy)
ethyl)amino)methyl)-3-(3-oxo-3,4-dihydro-2H-pyrazino[2,3-b][1,4]
thiazin-6-yl)oxazolidin-2-one (Compound 14)

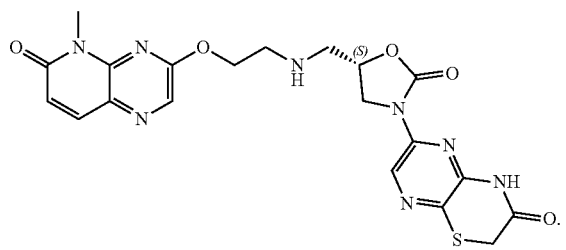

(S)-5-(((2-((5-Methyl-6-oxo-5,6-dihydropyrido[2,3-b]pyrazin-3-yl)oxy)
ethyl)amino)methyl)-3-(3-oxo-3,4-dihydro-2H-pyrazino[2,3-b][1,4]
thiazin-6-yl)oxazolidin-2-one According to an embodiment, the present disclosure relates to a process of preparation of compound of Formula I or its stereoisomers, pharmaceutically acceptable salts, complexes, hydrates, solvates, tautomers, polymorphs, racemic mixtures, optically active forms, and pharmaceutically active derivative thereof, said process comprising reacting Formula (A), and Formula (B)

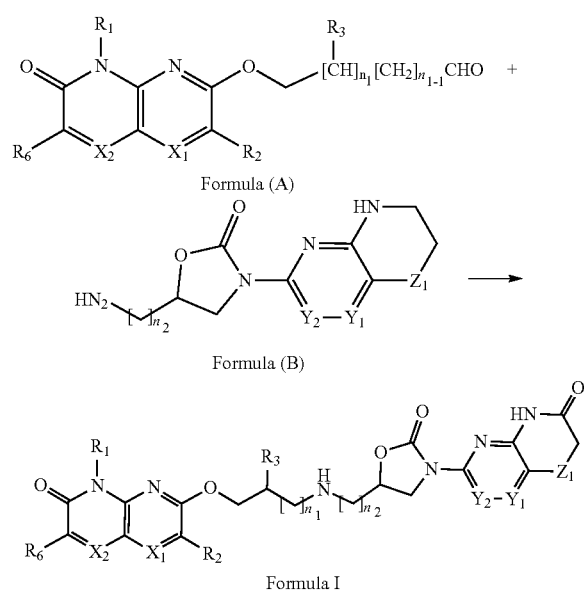

in presence of at least one reducing agent and an adsorbent to obtain the compounds of Formula I.

According to an embodiment, the present disclosure relates to a process of preparation of compound of Formula I or its stereoisomers, pharmaceutically acceptable salts, complexes, hydrates, solvates, tautomers, polymorphs, racemic mixtures, optically active forms, and pharmaceutically active derivative thereof, said process comprising reacting Formula (A), and Formula (B), in presence of at least one reducing agent and an adsorbent to obtain the compounds of Formula I, wherein $R_1$ of Formula (A) is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with upto three heteroatoms independently selected from O, N, or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, $O-PO_3H_2$, $COOR_9$, $CONHR_8$, $SO_2NHR$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ cycloalkylhydroxy, $C_{3-6}$ aminocycloalkyl, $C_{1-6}$ alkylamino, or 3-7 membered saturated or unsaturated heterocyclyl ring optionally substituted with upto three heteroatoms independently selected from O, N, or S; $R_8$ is selected from hydrogen, or $C_{1-6}$ alkyl; $R_2$ is selected from hydrogen, fluoro, cyano, $C_{1-6}$ alkoxy, or hydroxyl; $X_1$ is N or $CR_4$; $R_3$ is selected from hydrogen, $C_{1-6}$ alkyl, fluoro, $C_{1-6}$ alkoxy, hydroxyl, or amino; $R_4$ is selected from hydrogen, $C_{1-6}$ alkoxy, $C_{1-6}$ haloalkyl, $C_{1-6}$ haloalkoxy, or $C_{1-6}$ alkyl; $X_2$ is N or $CR_5$; $R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl; and $n_1$ is 0 to 2; $R_6$ selected from hydrogen, or $C_{1-6}$ alkyl; $Y_1$, and $Y_2$ of Formula (B) are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; $Z_1$ is selected from O, S, NH, or $CH_2$; $n_2$ is 1 or 2.

According to an embodiment, the present disclosure relates to a process of preparation of compound of Formula I or its stereoisomers, pharmaceutically acceptable salts, complexes, hydrates, solvates, tautomers, polymorphs, racemic mixtures, optically active forms, and pharmaceutically active derivative thereof, wherein the at least one reducing agent is selected from the group consisting of sodium borohydride, sodium cyano borohydride, sodium triacetoxy borohydride, and combinations thereof.

According to an embodiment, the present disclosure relates to a process of preparation of compound of Formula I or its stereoisomers, pharmaceutically acceptable salts, complexes, hydrates, solvates, tautomers, polymorphs, racemic mixtures, optically active forms, and pharmaceutically active derivative thereof, wherein the adsorbent is selected from the group consisting of molecular sieves, silicagel, zeolites, anhydrous sodium sulphate, anhydrous magnesium sulphate, activated charcoal, and combinations thereof.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivative thereof, for use as a medicament.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivative thereof, for use in killing or inhibiting the growth of a microorganism selected from the group consisting of bacteria, virus, fungi, and protozoa.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivative thereof, for use in treatment of a bacterial infection caused by a Gram-positive bacterium or a Gram-negative bacterium.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivative thereof, for use in treating a disease or condition in a patient wherein said disease or condition is caused by a microorganism selected from the group consisting of Gram-positive, and Gram-negative pathogens.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivative thereof, together with a pharmaceutically acceptable carrier.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivative thereof, for use in the preparation of medicaments for inhibiting microbial growth.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivative thereof, together with a pharmaceutically acceptable carrier, and in combination with at least one antibiotic.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivative thereof, in killing or inhibiting the growth of a microorganism selected from the group consisting of bacteria, virus, fungi, and protozoa.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivative thereof, According to an embodiment, the present disclosure relates to use of a compound of Formula I or its stereoisomers, pharmaceutically acceptable salts, complexes, hydrates, solvates, tautomers, polymorphs, racemic mixtures, optically active forms, and pharmaceutically active derivative thereof, in treating disease or condition in a patient, wherein said disease or condition is caused by a microorganism selected from the group consisting of Gram negative, and Gram positive pathogens. The patient is a typically a mammal, preferably a human.

According to an embodiment, the present disclosure relates to a method of treating a disease or condition in a patent, said method comprising administering to a patient a compound of Formula I, or its stereoisomers, pharmaceutically acceptable salts, complexes, hydrates, solvates, tautomers, polymorphs, racemic mixtures, optically active forms, and pharmaceutically active derivative thereof, wherein said disease or condition is caused by microorganism selected from the group consisting of Gram negative, and Gram positive pathogens.

According to an embodiment, the present disclosure relates to medicaments that include a compound of Formula I, or an addition salt of the compound of Formula I with a pharmaceutically acceptable acid or base. These medicaments find their use in therapeutics, especially in the treatment of bacterial infection caused by both drug sensitive and drug resistance bacterium including quinolone resistance belonging to Gram positive and Gram negative species; especially of those caused by *Escherichia coli, Staphylococcus aureus, Salmonella typhi, Salmonella paratyphi, Salmonella typhimurium, Salmonella enteritidis, Shigella dysenteriae, Shigella flexneri, Shigella boydii, Shigella sonnei, Staphylococcus epidermidis, Streptococcus pneumoniae, Streptococcus pygenes, Stenotrophomonas maltophilia, Haemophilus influenza, Legionella pneumophila. Mycoplasma pneumonia, Acinetobacter haemolyticus Acinetobacter junii, Acinetobacter lwoffi, Burkholderia cepacia, Chlamydophila pneumoniae, Clostridium difficili, Enterobacter aerogenes, Enterobacter cloacae. Moraxella catarrhalis, Enterococcus faecium Neisseria gonorrhoeae, Neisseria meningitides, Klebsiella pneumoniae, Acinetobacter baumannii, Pseudomonas aeruginosa*, and *Enterococcus faecalis Enterococcus faecium*.

According to an embodiment, the present disclosure relates to the use of a compound of Formula I, or its stereoisomers, pharmaceutically acceptable salts, complexes, hydrates, solvates, tautomers, polymorphs, racemic mixtures, optically active forms, and pharmaceutically active derivative thereof, in the manufacture of a medicament for the treatment of an infection caused by bacterial species in a warm-blooded animal, such as man.

According to an embodiment, the present disclosure relates to the use of a compound of Formula I, or its stereoisomers, pharmaceutically acceptable salts, complexes, hydrates, solvates, tautomers, polymorphs, racemic mixtures, optically active forms and pharmaceutically active derivative thereof, in the manufacture of a medicament for the production of an antibacterial effect in a warm-blooded animal such as man.

According to an embodiment, the present disclosure relates to a method for treating a bacterial infections caused by bacterial species in a warm-blooded animal such as man, said method including administering to said animal an effective amount of a compound of Formula I, or a pharmaceutically acceptable salt thereof.

According to an embodiment, the present disclosure relates to a method for producing an antibacterial effect in a warm-blooded animal such as man, said method including administering to said animal an effective amount of a compound of Formula I, or a pharmaceutically acceptable salt thereof.

According to an embodiment, the present disclosure relates to a compound of Formula I, or a pharmaceutically acceptable salt thereof, for use in the treatment and/or prophylaxis of bacterial infections in a warm-blooded animal, such as man.

According to an embodiment, the present disclosure relates to a compound of Formula I, or a pharmaceutically acceptable salt thereof, for the therapeutic and prophylactic treatment of mammals including humans, in particular in treating bacterial infections caused by bacterial species, is normally formulated in accordance with standard pharmaceutical practice as a pharmaceutical composition.

According to an embodiment, the present disclosure relates to a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivative thereof, and at least one pharmaceutically acceptable carrier, diluent, or excipient.

According to an embodiment, the present disclosure relates to the use of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivative thereof, in the manufacture of a medicament for the treatment of a bacterial infection caused by bacterial species in a warm-blooded animal such as man.

According to an embodiment, the present disclosure relates to the use of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivative thereof, in the manufacture of a medicament for the production of an antibacterial effect in a warm-blooded animal such as man.

According to an embodiment, the present disclosure relates to a pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivative thereof together with a pharmaceutically acceptable carrier, and in combination with at least one antibiotic.

According to an embodiment, the present disclosure relates to a method for treating infection caused by bacterial species in a warm-blooded animal such as man, said method including administering to said animal an effective amount of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivative thereof.

According to an embodiment, the present disclosure relates to a method for producing an antibacterial effect in a warm-blooded animal such as man, said method including administering to said animal an effective amount of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivative thereof.

According to an embodiment, the present disclosure relates to a pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivative thereof, together with a pharmaceutically acceptable carrier, optionally in combination with one or more other pharmaceutical compositions.

According to an embodiment, the present disclosure relates to a pharmaceutical composition comprising a compound of Formula I, or its stereoisomers, pharmaceutically acceptable salts, complexes, hydrates, solvates, tautomers, polymorphs, racemic mixtures, optically active forms and pharmaceutically active derivative thereof, and a pharmaceutically acceptable diluent or carrier.

According to an embodiment, the present disclosure relates to a method for treatment of bacterial infection in a subject comprising: administering to the subject an effective amount of the compound of Formula I, or its stereoisomers, pharmaceutically acceptable salts, complexes, hydrates, solvates, tautomers, polymorphs, racemic mixtures, optically active forms and pharmaceutically active derivative thereof.

According to an embodiment, the present disclosure relates to a method for treatment of bacterial infection in a subject comprising: administering to the subject an effective amount of the compound of Formula I, or its stereoisomers, pharmaceutically acceptable salts, complexes, hydrates, solvates, tautomers, polymorphs, racemic mixtures, optically active forms and pharmaceutically active derivative thereof, wherein the bacterial infection is caused by a Gram-positive or a Gram-negative pathogen.

According to an embodiment, the present disclosure relates to a method for treatment of bacterial infection in a subject comprising: administering to the subject an effective amount of the compound of Formula I, or its stereoisomers, pharmaceutically acceptable salts, complexes, hydrates, solvates, tautomers, polymorphs, racemic mixtures, optically active forms and pharmaceutically active derivative thereof, wherein the bacterial infection is caused by *E. coli, Pusedomonas aurigenosa, Klebsiella pneumoniae, Acinetobacter baumannii, Enterobacter cloacae, Staphylococcus aureus, Enterococcus faecalis Enterococcus faecium, Legionella pneumophila. Mycoplasma* pneumonia, *Acinetobacter haemolyticus Acinetobacter junii, Acinetobacter lwoffi, Burkholderia cepacia, Chlamydophila pneumoniae, Clostridium difficili, Enterobacter aerogenes, Enterobacter cloacae. Moraxella catarrhalis, Neisseria gonorrhoeae, Neisseria meningitides, Proteus mirabilis, Proteus houseri, Citrobacter freundii, Citrobacter kosari, Citrobacter barakii, Seratia marcescens, Klebsiella oxytoca, Morganella morganii, Helicobacter pyroli*, and *Mycobacterium tuberculosis.*

The language "pharmaceutically acceptable" includes compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula I may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N10 methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion ona suitable ion-exchange resin.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The present disclosure relates to a process of preparation of a composition comprising a compound of Formula I or its stereoisomers, pharmaceutically acceptable salts, complexes, hydrates, solvates, tautomers, polymorphs, racemic mixtures, optically active forms and pharmaceutically active derivative thereof together with a carrier.

The present disclosure relates to a process of preparation of pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivative thereof, together with a pharmaceutically acceptable carrier, optionally in combination with one or more other pharmaceutical compositions.

The compositions of the present disclosure may be obtained by conventional procedures using conventional pharmaceutical excipients well known in the art. Thus, compositions intended for oral use may contain, for example, one or more colouring, sweetening, flavouring and/or preservative agents Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents or procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as *arachis* oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the disclosure may also be in the form of oil-in-water emulsions. The oily phase may be a vegetable oil, such as olive oil or *arachis* oil, or a mineral oil, such as for example liquid paraffin or a mixture of any of these.

Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for administration may also be formulated as a liposome preparation. The liposome preparation can comprise liposomes which penerate the cells of interest or stratum corneum, and fuse with the cell membrane, resulting in delivery of the contents of the liposome into the cell. Other suitable formulations can employ niosomes.

Niosomes are lipid vesicles similar to liposomes, with membrane consisting largely of nonoinic lipids, some forms of which are effective for transporting compounds across the stratum corneum.

Compositions for administration may also be formulated as a depot preparation, which may be administered by implantation or by intramuscular injection. The compositions may be formulated with suitable polymeric or hydrophobic material (as an emulsion in acceptable oil), ion exchange resins, or sparingly soluble derivatives.

The compound of the present disclosure can also be administered in sustained release forms or from sustained release drug delivery systems.

For further information on formulation, drug delivery as well as processing techniques the reader is referred to Remington's Pharmaceutical Sciences (2$^{st}$ Edition, 2005, University of the sciences in Philadelphia, Lippincott William & Wilkins)

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990 and Remington's Pharmaceutical Sciences (21$^{st}$ Edition, 2005, University of the sciences in Philadelphia, Lippincott William & Wilkins).

As stated above the size of the dose required for the therapeutic or prophylactic treatment of a particular disease state will necessarily be varied depending on the host treated, the route of administration and the severity of the illness being treated.

Preferably a daily dose in the range of 1-25 mg/kg is employed. Accordingly, the optimum dosage may be determined by the practitioner who is treating any particular patient.

In any of the pharmaceutical compositions, processes, methods, uses, medicaments, and manufacturing features mentioned herein, any of the alternate aspects of the compounds of the disclosure described herein also apply.

The compounds disclosed herein may be applied as a sole therapy or may involve, in addition to a compound of the disclosure, one or more other substances and/or treatments. Such conjoint treatment may be achieved by way of the simultaneous, sequential or separate administration of the individual components of the treatment. Where the administration is sequential or separate, the delay in administering the second component should not be such as to lose the beneficial effect of the combination. Suitable classes and substances may be selected from one or more of the following: i) other antibacterial agents for example macrolides e.g. erythromycin, azithromycin or clarithromycin; quinolones e.g. ciprofloxacin orlevofloxacin; Blactams e.g. penicillins e.g. amoxicillin or piperacillin; cephalosporins e.g. ceftriaxone or ceftazidime; carbapenems, e.g. meropenem or imipenem etc; aminoglycosides e.g. gentamicin or tobramycin; or oxazolidinones; and/or ii) anti-infective agents for example, an antifungal triazole e.g. or amphotericin; and/or iii) biological protein therapeutics for example antibodies, cytokines, bactericidal/permeability increasing protein (BPI) products; and/or iv) one or more antibacterial agents useful in the treatment of *Mycobacterium tuberculosis* such as one or more of rifampicin, isoniazid, pyrizinamide, ethambutol, quinolones e.g. moxifloxacin or gatifloxacin, streptomycin and/or v) efflux pump inhibitors.

According to an embodiment, the present disclosure relates to a compound of the Formula I, or a pharmaceutically acceptable salt thereof and a chemotherapeutic agent selected from: i) one or more additional antibacterial agents; and/or ii) one or more anti-infective agents; and/or iii) biological protein therapeutics for example antibodies, cytokines, bactericidal/permeability increasing protein (BPI) products; iv) one or more antibacterial agents useful in the treatment of pulmonary tuberculosis, extra-pulmonary tuberculosis, *avium* infections, buruli ulcers and/or v) one or more efflux pump inhibitors.

If not commercially available, the necessary starting materials for the procedures such as those described herein may be made by procedures which are selected from standard organic chemical techniques, techniques which are analogous to the synthesis of known, structurally similar compounds, or techniques which are analogous to the described procedure or the procedures described in the Examples.

It is noted that many of the starting materials for synthetic methods as described herein are commercially available and/or widely reported in the scientific literature, or could be made from commercially available compounds using adaptations of processes reported in the scientific literature. The reader is further referred to Advanced Organic Chemistry, 5th Edition, by Jerry March and Michael Smith, published by John Wiley & Sons 2001, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T.W. Greene, Protective Groups in Organic Synthesis, published by John Wiley and Sons, 1991) and as described hereinabove.

Abbreviations

The following abbreviations are employed in the examples and elsewhere herein:
TLC—thin layer chromatography;
HPLC—high pressure liquid chromatography;
MPLC—medium pressure liquid chromatography;
NMR—nuclear magnetic resonance spectroscopy;
DMSO—dimethylsulfoxide;

CDCl₃—deuterated chloroform;
MeOD—deuterated methanol, i.e. D₃COD;
MS—mass spectroscopy; ESP (or ES)—electrospray; EI—electron impact; APCI—atmospheric pressure chemical ionization;
THF—tetrahydrofuran;
DCM—dichloromethane;
MeOH—methanol;
DMF—dimethylformamide;
EtOAc—ethyl acetate;
LC/MS—liquid chromatography/mass spectrometry;
h—hour(s); min is minute(s);
d—day(s);
MTBD—N-methyl-1,5,7-triazabicyclo[4.4.0]dec-5-ene;
TFA—trifluoroacetic acid; v/v—ratio of volume/volume;
Boc denotes t-butoxycarbonyl;
Cbz denotes benzyloxycarbonyl;
Bz denotes benzoyl;
atm denotes atmospheric pressure;
rt denotes room temperature;
mg denotes milligram; g denotes gram;
μL denotes microliter;
mL denotes milliliter;
L denotes liter;
μM denotes micromolar;
mM denotes millimolar; M denotes molar;
N denotes normal; and
nm denotes nanometer.

EXAMPLES

The following examples provide the details about the synthesis, activities and applications of the compounds of the present disclosure. It should be understood the following is representative only, and that the disclosure is not limited by the details set forth in these examples.
Materials and Methods:

Evaporations were carried out by rotary evaporation in vacuo and work up procedures were carried out after removal of residual solids by filtration; temperatures are quoted as ° C.; operations were carried out at room temperature, that is typically in the range 18 to 26° C. and without the exclusion of air unless otherwise stated, or unless the skilled person would otherwise work under an inert atmosphere; column chromatography (by the flash procedure) was used to purify compounds and was performed on Merck Kieselgel silica (Art. 9385) unless otherwise stated; in general, the course of reactions was followed by TLC, HPLC, or LC/MS and reaction times are given for illustration only; yields are given for illustration only and are not necessarily the maximum attainable; the structure of the end products of the disclosure was generally confirmed by NMR and mass spectral techniques. Proton magnetic resonance spectra were generally determined in DMSO d6 unless otherwise stated, using a Bruker DRX 300 spectrometer or a Bruker DRX-400 spectrometer, operating at a field strength of 300 MHz or 400 MHz, respectively. In cases where the NMR spectrum is complex, only diagnostic signals are reported. Chemical shifts are reported in parts per million downfield from tetramethylsilane as an external standard (S scale) and peak multiplicities are shown thus: s, singlet; d, doublet; dd, doublet of doublets; dt, doublet of triplets; dm, doublet of multiplets; t, triplet; m, multiplet; br, broad.

Fast atom bombardment (FAB) mass spectral data were generally obtained using a Platform spectrometer (supplied by Micromass) run in electrospray and, where appropriate, either positive ion data or negative ion data were collected or using Agilent 1100 series LC/MS equipped with Sedex 75ELSD, and where appropriate, either positive ion data or negative ion data were collected. The lowest mass major ion is reported for molecules where isotope splitting results in multiple mass spectral peaks (for example when chlorine is present). Reverse Phase HPLC was carried out using YMC Pack ODS AQ (100×20 mmID, S 5 Å particle size, 12 nm pore size) on Agilent instruments; each intermediate was purified to the standard required for the subsequent stage and was characterized in sufficient detail to confirm that the assigned structure was correct; purity was assessed by HPLC, TLC, or NMR and identity was determined by infrared spectroscopy (IR), mass spectroscopy or NMR spectroscopy as appropriate.

Example 1

General process for the preparation of the compounds of Formula A

Compounds of Formula (E) were N-alkylated to obtain the compounds of Formula (D). Further the compounds of Formula D were converted into compounds of Formula (C) m via palladium catalysed hydroxylation. Then, compounds of Formula (C), via alkylation of hydroxyl group of the naphthyridone with haloalkyl acetal reagent (e.g BrCH₂(CHR₃)n₁(CH2)$_{n1-1}$CH(OCH₂CH₃)₂) gave compounds of Formula (A) as depicted in the general scheme below:

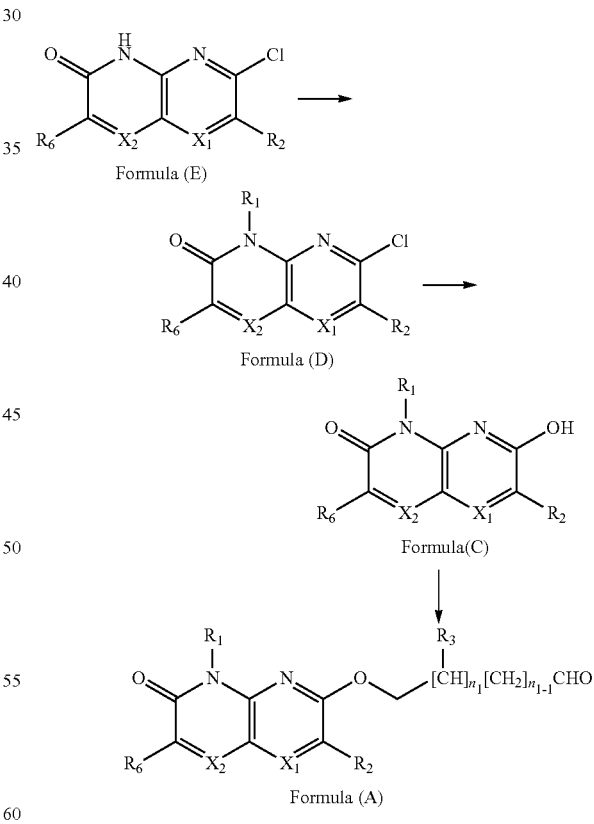

General Process for the Preparation of the Compounds of Formula B

The compounds of Formula (B) were obtained from compounds of Formula (H) and compounds of Formula I as summarised in the below Scheme. Palladium catalysed Buchwald coupling of compounds of formula (H) with Formula (I) under optimal reaction conditions provided the compounds of formula (J). Further compounds of Formula (J) was converted to compounds of Formula (K) via azidation reaction and reduction of azide functionality provided the compounds Formula (B).

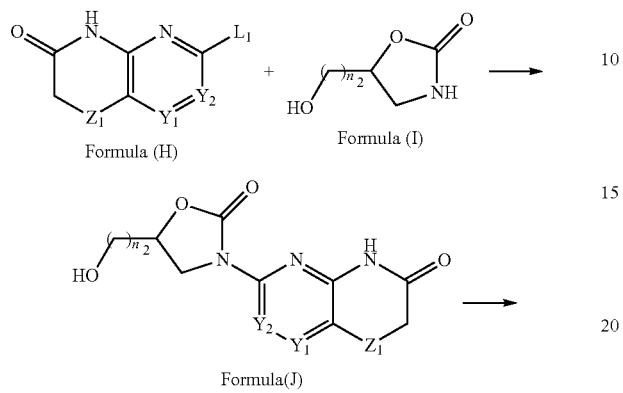

-continued

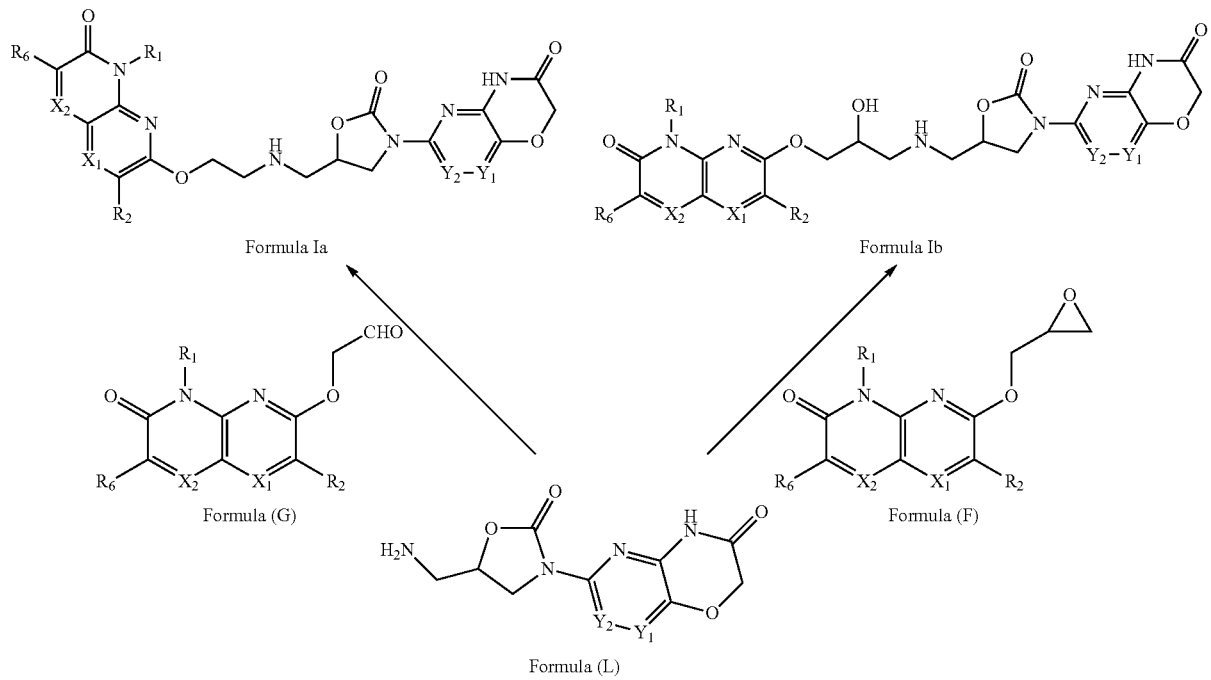

Example 2

The compounds of Formula Ia and Formula Ib where in $Z_1$ is O; $n_1=0$; $R_3$ is H or OH, can be prepared by reacting compounds of Formula (L) with compounds of Formula (G) or (F) as shown in the below Scheme. The reductive amination of compounds Formula (L) with compounds of Formula (G) provided the compounds of Formula Ia, whereas the epoxide ring opening of compounds Formula (F) with compound of Formula (L) provided the compounds of Formula Ib.

-continued

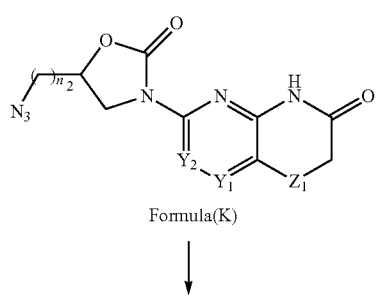

Formula(K)

Example 3

Synthesis of Intermediates

Synthesis of 6-(5-(2-aminoethyl)-2-oxooxazolidin-3-yl)-2H-pyrido[3,2-b][1,4]oxazin-3(4H)-one (Intermediate I)

Intermediate I, 6-(5-(2-aminoethyl)-2-oxooxazolidin-3-yl)-2H-pyrido[3,2-b][1,4]oxazin-3(4H)-one (CAS number 2156619-15-5) was synthesized as reported in WO2017199265.

Synthesis of (S)-6-(5-(aminomethyl)-2-oxooxazolidin-3-yl)-2H-pyrido[3,2-b][1,4]oxazin-3(4H)-one, II

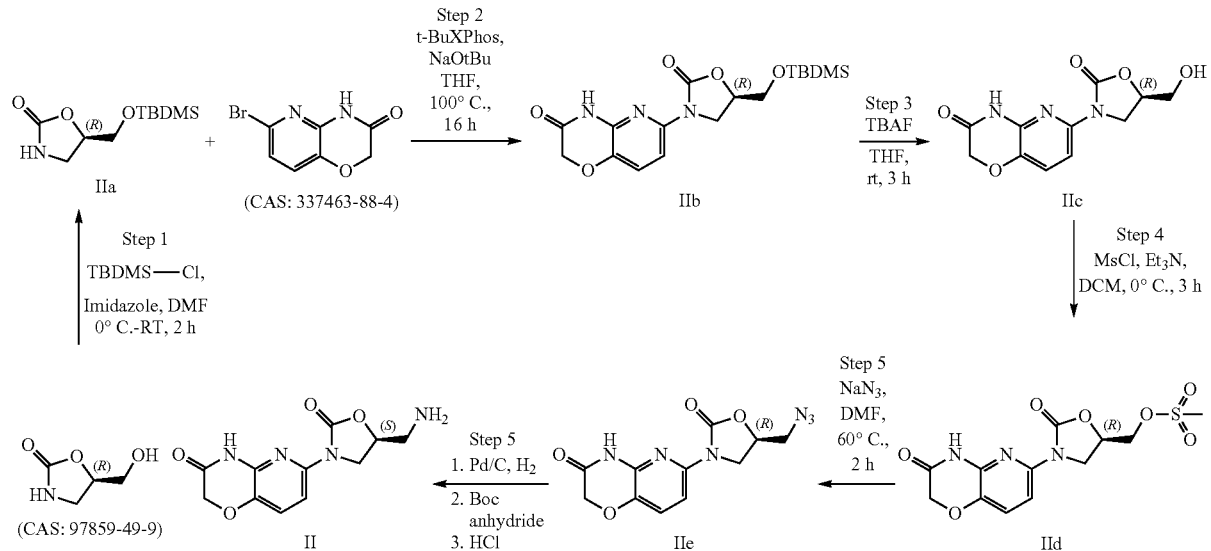

Step 1: (R)-5-(((tert-butyldimethylsilyl)oxy)methyl)oxazolidin-2-one (IIa)

To a stirred solution of TBDMS-Cl (38.46 g, 0.256 mol), imidazole (23.2 g, 0.341 mol), DMAP (2.08 g, 0.017 mol) in DMF (200 mL), cooled to 0° C., (R)-5-(hydroxymethyl) oxazolidin-2-one (CAS: 97859-49-9, 20 g, 0.1709 mmol) in DMF (25 mL) was added and stirred at 25° C. for 2 h. After completion of the reaction, reaction mixture was quenched with water and extracted with ethyl acetate. The separated organic layer was washed with water, brine solution (200 mL), dried over $Na_2SO_4$, filtered, and concentrated under reduced pressure. It was purified by column chromatography on silica gel (230-400 mesh, 20-25% ethyl acetate in pet ether) to obtain IIa (32 g, 81%).

LC_MS Calculated for $C_{10}H_{21}NO_3Si$, 231.37, Observed 232.1. $^1$H NMR (400 MHz, $CDCl_3$): δ 5.11 (s, 1H), 4.72-4.66 (m, 1H), 3.86-3.82 (m, 1H), 3.79-3.76 (m, 1H), 3.66-3.62 (m, 1H), 3.58-3.55 (m, 1H), 0.91 (s, 9H), 0.11 (s, 6H).

Step 2: (R)-6-(5-(((tert-butyldimethylsilyl)oxy)methyl)-2-oxooxazolidin-3-yl)-2H-pyrido[3,2-b][1,4]oxazin-3(4H)-one (IIb)

To a stirred solution of IIa (32 g, 0.139 mol) and 6-bromo-2H-pyrido[3,2-b][1,4]oxazin-3(4H)-one (WO2017199265, 31.7 g, 0.139 mol) in dry 1,4-dioxane (50 mL), were added t-butyl-X-Phos mesyl chloride complex (5.5 g, 0.0069 mol) and sodium tert-butoxide (19.94 g, 0.207 mol) and was degassed for 20 mins. Then, it was heated in sealed tube at 100° C. for 16 h. After completion of the reaction, reaction mixture was concentrated under reduced pressure. It was purified by column chromatography on silica gel (230-400 mesh, 25-30% ethyl acetate in pet ether) to afford IIb (45.6 g, 86%).

LC_MS Calculated for $C_{17}H_{25}N_3O_5Si$, 379.49, Observed 380.0.

$^1$H NMR (400 MHz, DMSO-d6). δ 7.60 (d, J=8.68 Hz, 1H), 7.43 (d, J=8.68 Hz, 1H), 4.77-4.73 (m, 1H), 4.67 (s, 2H), 4.15-4.10 (m, 1H), 3.93-3.89 (m, 3H), 0.79 (s, 9H), 0.04 (s, 6H).

Step 3: (R)-6-(5-(Hydroxymethyl)-2-oxooxazolidin-3-yl)-2H-pyrido[3,2-b][1,4]oxazin-3(4H)-one (IIc)

To a stirred solution of IIb (45 g, 0.118 mol) in TH (250 mL), cooled to 0° C., tert-butyl ammonium fluoride (1 M in THF) (296 mL, 0.296 mol) was added drop wise and stirred at 25° C. for 3 hours. After completion of the reaction, reaction mixture was quenched with water obtained solid filtered and dried in vacuum to obtain white solid of IIc (29 g, 92%).

LC_MS Calculated for $C_{11}H_{11}N_3O_5$, 265.23, Observed=265.9.

$^1$H NMR (400 MHz, DMSO-$d_6$): δ 11.22 (s, 1H), 7.60 (d, J=8.80 Hz, 1H), 7.42 (d, J=8.40 Hz, 1H), 5.21 (bs, 1H), 4.70-4.66 (m, 1H), 4.60 (s, 2H), 4.12-4.07 (m, 1H), 3.92-3.88 (m, 1H), 3.69-3.65 (m, 1H), 3.54-3.34 (m, 1H).

Step 4: (R)-(2-oxo-3-(3-oxo-3,4-dihydro-2H-pyrido[3,2-b][1,4]oxazin-6-yl)oxazolidin-5-yl)methyl methanesulfonate (Id)

To a stirred solution of Ic (29 g, 0.109 mol) in dry DMF (300 mL), cooled to 0° C., triethylamine (45.7 mL, 0.328 mol) and mesyl chloride (17 mL, 0.218 mol) were added and stirred at 25° C. for 2 h. After completion of the reaction, reaction mixture was quenched with water obtained solid filtered dried in vacuum to obtain white solid of Id (30 g, 80%).

LC_MS Calculated for $C_{12}H_{13}N_3O_7S$, 343.31; Observed 344.0.

$^1$H NMR (400 MHz, DMSO-$d_6$): δ 11.27 (s, 1H), 7.61 (d, J=8.40 Hz, 1H), 7.46 (d, J=8.80 Hz, 1H), 5.00 (bs, 1H), 4.63 (s, 2H), 4.63-4.51 (m, 2H), 4.25-4.20 (m, 1H), 3.90-3.85 (m, 1H), 3.35 (s, 3H).

Step 5: (R)-6-(5-(azidomethyl)-2-oxooxazolidin-3-yl)-2H-pyrido[3,2-b][1,4]oxazin-3(4H)-one (IIe)

To a stirred solution of Id (30 g, 0.087 mol) in DMF (300 mL), cooled to 0° C., sodium azide (17 g, 0.262 mol) was added and heated at 60° C. for 3 h. After completion of the reaction, reaction mixture was quenched with water obtained solid filtered and dried in vacuo to obtain white solid of Ie (22 g, 87%).

LC_MS Calculated for $C_{11}H_{10}N_6O_4$, 290.24; Observed 290.9.

$^1$H NMR (400 MHz, DMSO-d$_6$): δ 11.26 (s, 1H), 7.61 (d, J=8.40 Hz, 1H), 7.45 (d, J=8.80 Hz, 1H), 4.88 (bs, 1H), 4.63 (s, 2H), 4.16 (t, J=9.60 Hz, 1H), 3.70-3.84 (m, 3H).

Step 6: (S)-6-(5-(aminomethyl)-2-oxooxazolidin-3-yl)-2H-pyrido[3,2-b][1,4]oxazin-3(4H)-one (II)

To a stirred solution of Ie (22 g, 0.075 mol) in THF:MeOH (1:1) (400 ml), 10% palladium on carbon (7 g) was added and stirred at 25° C. under H$_2$ for 4 h. After completion of the reaction, reaction mixture was filtered through celite bed using THF and MeOH and concentrated under reduced pressure to obtain II (15 g, 75%).

LC_MS Calculated for $C_{11}H_{12}N_4O_4$, 264.24; Observed 265.1.

Purification of Intermediate II: Boc Protection: To a stirred solution of crude II (15 g, 0.056 mol) in 1,4 dioxane: water (1:1, 200 mL) was added Na$_2$CO$_3$ (12 g, 0.113 mol) followed by the addition of (Boc)$_2$O (25 g, 0.113 mol) at 0° C. and allowed to stir at room temperature for 12 h. The reaction mixture was diluted with EtOAc (250 mL) and washed with water (2×250 mL). The combined organic layers were washed with brine (50 mL), dried over sodium sulphate and evaporated under reduced pressure to get the crude. Crude was purified by column chromatography (230/400 mesh, 4% DCM in MeOH) to get desire Boc protected II as white solid (12 g, 58%).

Analytical data for Boc protected II; LC_MS Calc. for $C_{16}H_{20}N_4O_6$: 364.36; Obs. 265.1;

$^1$H NMR (400 MHz, DMSO-D6): δ 11.23 (s, 1H), 7.61 (d, 1H, J=8.8 Hz), 7.45 (d, 1H, J=8.8 Hz), 7.24 (m, 1H), 4.71 (m, 1H), 4.60 (s, 2H), 4.16-4.11 (m, 1H), 3.84-3.80 (m, 1H), 3.25 (m, 2H), 1.36 (s, 9H).

The Boc protected II (12 g, 0.033 mmol) was taken in 1,4 dioxane (60 mL) and 4M HCl in dioxane (120 mL) was added at 0° C. to it. The resulting mixture was stirred at room temperature for 3 h. The reaction mixture was concentrated to obtain crude amine HCl salt. The crude was dissolved in dry MeOH/DCM (200 mL) and neutralized with resin, filtered and concentrated to afford pure amine II as off white solid (8 g, 92%).

LC_MS Calc. for $C_{11}H_{12}N_4O_4$, 264.24; Obs. 265.1 [M+H];

$^1$H NMR (400 MHz, DMSO-D6): δ 11.05 (brs, 1H), 7.62 (d, 1H, J=8.8 Hz), 7.45 (d, 1H, J=8.8 Hz), 7.05 (brs, 2H), 4.83 (m, 1H), 4.62 (s, 2H), 4.23-4.20 (m, 1H), 3.87-3.82 (m, 1H), 3.19-3.10 (m, 2H).

Synthesis of (R)-6-(5-(aminomethyl)-2-oxooxazolidin-3-yl)-2H-pyrido[3,2-b][1,4]oxazin-3(4H)-one, III

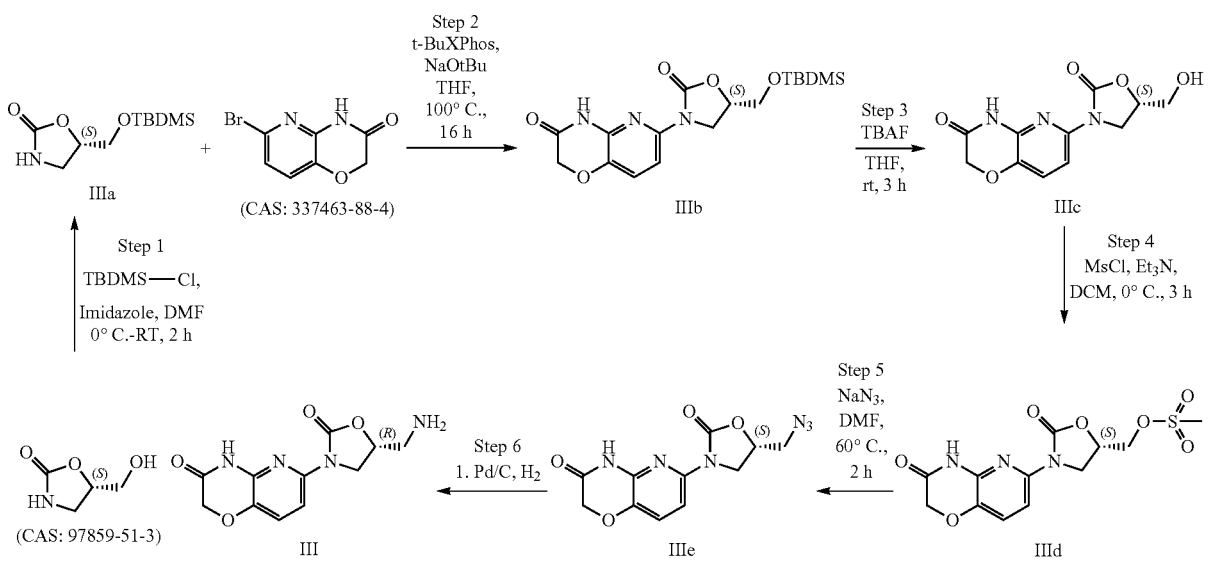

Step 1: (S)-5-(((tert-butyldimethylsilyl)oxy)methyl)oxazolidin-2-one (Ia)

To a stirred solution of TBDMS-Cl (5.74 g, 0.0384 mol), imidazole (3.4 g, 0.0512 mol), DMAP (0.31 g, 0.0025 mol) in DMF (15 mL), cooled to 0° C., (S)-5-(hydroxymethyl)oxazolidin-2-one (3 g, 0.0256 mmol) in DMF (15 mL) was added and stirred at 25° C. for 2 h. After completion of the reaction, reaction mixture was quenched with water and extracted with ethyl acetate. The separated organic layer was washed with water, brine (50.mL), dried over Na$_2$SO$_4$, filtered and concentrated under reduced pressure. It was purified by column chromatography on silica gel (230-400 mesh, 20-25% ethyl acetate in pet ether) to obtain IIa (3.6 g, 61%).

$^1$H NMR (400 MHz, CDCl$_3$): δ 5.11 (s, 1H), 4.72-4.66 (m, 1H), 3.86-3.82 (m, 1H), 3.79-3.76 (m, 1H), 3.66-3.62 (m, 1H), 3.58-3.55 (m, 1H), 0.91 (s, 9H), 0.11 (s, 6H).

LC_MS Calculated for C$_{10}$H$_{21}$NO$_3$Si, 231.37, Observed 232.1.

Step 2: (S)-6-(5-(((tert-butyldimethylsilyl)oxy) methyl)-2-oxooxazolidin-3-yl)-2H-pyrido[3,2-b][1,4]oxazin-3(4H)-one (IIb)

To a stirred solution of IIa (3.92 g, 0.0171 mol) and 6-bromo-2H-pyrido[3,2-b][1,4]oxazin-3(4H)-one (WO2017199265, 3.6 g, 0.0155 mol) in dry 1,4-Dioxane (50 mL), were added t-butyl-X-Phos mesyl chloride complex (0.618 g, 0.0077 mol) and sodium tert-butoxide (2.24 g, 0.0234 mol) and degassed for 20 mins. Then, it was heated in sealed tube at 100° C. for 16 h. After completion of the reaction, reaction mixture was concentrated under reduced pressure. It was purified by column chromatography on silica gel (230-400 mesh, 25-30% ethyl acetate in pet ether) to afford IIb (3.5 g, 59%). 1H NMR (400 MHz, DMSO-d$_6$): 7.60 (d, J=8.68 Hz, 1H), 7.43 (d, J=8.68 Hz, 1H), 4.77-4.73 (m, 1H), 4.67 (s, 2H), 4.15-4.10 (m, 1H), 3.93-3.89 (m, 3H), 0.79 (s, 9H), 0.04 (s, 6H);

LC_MS Calculated for C$_{17}$H$_{25}$N$_3$O$_5$Si, 379.49, Observed 380.0.

Step 3: (S)-6-(5-(Hydroxymethyl)-2-oxooxazolidin-3-yl)-2H-pyrido[3,2-b][1,4]oxazin-3(4H)-one (IIc)

To a stirred solution of IIb (5 g, 0.0132 mol) in THF (25 mL), cooled to 0° C., tert-butyl ammonium fluoride (1 M in THF) (29.38 mL, 0.0293 mol) was added dropwise and stirred at 25° C. for 3 hours. After completion of the reaction, reaction mixture was quenched with water obtained solid filtered and dried in vacuum to obtain white solid of IIc (3.0 g, 85%). 1H NMR (400 MHz, DMSO-d$_6$): δ 11.22 (s, 1H), 7.60 (d, J=8.80 Hz, 1H), 7.42 (d, J=8.40 Hz, 1H), 5.21 (bs, 1H), 4.70-4.66 (m, 1H), 4.60 (s, 2H), 4.12-4.07 (m, 1H), 3.92-3.88 (m, 1H), 3.69-3.65 (m, 1H), 3.54-3.34 (m, 1H); LC_MS Calculated for C$_{11}$H$_{11}$N$_3$O$_5$, 265.23, Observed=265.9.

Step 4: (S)-(2-oxo-3-(3-oxo-3,4-dihydro-2H-pyrido[3,2-b][1,4]oxazin-6-yl)oxazolidin-5-yl)methyl methanesulfonate (IIId)

To a stirred solution of IIIc (3 g, 0.0113 mol) in dry DMF (30 mL), cooled to 0° C., triethylamine (3.15 mL, 0.0226 mol) and mesyl chloride (1.05 mL, 0.0135 mol) were added and stirred at 25° C. for 2 h. After completion of the reaction, reaction mixture was quenched with water and filtered. Obtained solid was dried in vacuum to obtain white solid of IIId (2.8 g, 73%).

1H NMR (400 MHz, DMSO-d$_6$): δ 11.27 (s, 1H), 7.61 (d, J=8.40 Hz, 1H), 7.46 (d, J=8.80 Hz, 1H), 5.00 (bs, 1H), 4.63 (s, 2H), 4.63-4.51 (m, 2H), 4.25-4.20 (m, 1H), 3.90-3.85 (m, 1H), 3.35 (s, 3H);

LC_MS Calculated for C$_{12}$H$_{13}$N$_3$O$_7$S, 343.31; Observed 344.0.

Step 5: (S)-6-(5-(azidomethyl)-2-oxooxazolidin-3-yl)-2H-pyrido[3,2-b][1,4]oxazin-3(4H)-one (IIIe)

To a stirred solution of IIId (2.8 g, 0.00816 mol) in DMF (28 mL), cooled to 0° C., sodium azide (1.3 g, 0.0204 mol) was added and heated at 60° C. for 3 h. After completion of the reaction, reaction mixture was quenched with water and filtered. Obtained solid was dried in vacuum to obtain white solid of IIIe (1.9 g, 80%).

$^1$H NMR (400 MHz, DMSO-d$_6$): δ11.26 (s, 1H), 7.61 (d, J=8.40 Hz, 1H), 7.45 (d, J=8.80 Hz, 1H), 4.88 (bs, 1H), 4.63 (s, 2H), 4.16 (t, J=9.60 Hz, 1H), 3.84-3.70-3.84 (m, 3H);

LC_MS Calculated for C$_{11}$H$_{10}$N$_6$O$_4$, 290.24; Observed 290.9.

Step 6: (R)-6-(5-(aminomethyl)-2-oxooxazolidin-3-yl)-2H-pyrido[3,2-b][1,4]oxazin-3(4H)-one (III)

To a stirred solution of IIe (1.9 g, 0.00653 mol) in THF:MeOH (1:1) (40 ml), 10% palladium on carbon (0.6 g) was added and stirred at 25° C. under H$_2$ for 4 h. After completion of the reaction, reaction mixture was filtered through celite bed using THF and MeOH and concentrated under reduced pressure to obtain III (1.22 g, 70%). The crude material was taken for next step without any purification.

$^1$H NMR (400 MHz, DMSO-d$_6$): δ7.61 (d, J=8.80 Hz, 1H), 7.43 (d, J=8.80 Hz, 1H), 4.61 (s, 2H), 4.10 (t, J=8.80 Hz, 1H), 3.91-3.86 (m, 1H), 2.88-2.79 (m, 2H);

LC_MS Calculated for C$_{11}$H$_{12}$N$_4$O$_4$, 264.24; Observed 265.1.

Synthesis of 6-chloro-2H-pyrazino[2,3-b][1,4]oxazin-3(4H)-one, IV

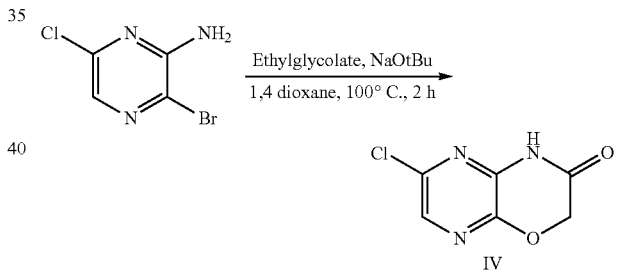

To a stirred solution of 3-bromo-6-chloropyrazin-2-amine (75 g, 0.3598 mol) in 1,4-dioxane (1500 mL) at room temperature under nitrogen atmosphere was added sodium tert-butoxide (110.65 g, 1.1514 mol) and stirred for 30 minutes. Then ethyl glycolate (112.37 g, 1.0794 mol) was added dropwise over a period of 30 minutes at room temperature. The resulting mixture was heated to 100° C. and stirred for 2 hours. The progress of the reaction was monitored by TLC.

After that the reaction mixture was cooled to room temperature and concentrated under reduced pressure to remove the dioxane. The residue obtained was diluted with water (750 mL) and neutralized using HCl (1.5 N). The precipitated solid was filtered out and dried under vacuum to get the compound IV as an off white solid. Yield: 60 g, 89.9%

LC_MS Calc. for C$_6$H$_4$ClN$_3$O$_2$, 185.57, Observed 184.0 (M−1H);

$^1$H NMR (400 MHz, DMSO-d6): δ 11.86 (s, 1H), 7.87 (s, 1H), 4.90 (s, 2H).

Synthesis of (S)-6-(5-(aminomethyl)-2-oxooxazolidin-3-yl)-2H-pyrazino[2,3-b][1,4]oxazin-3(4H)-one, V

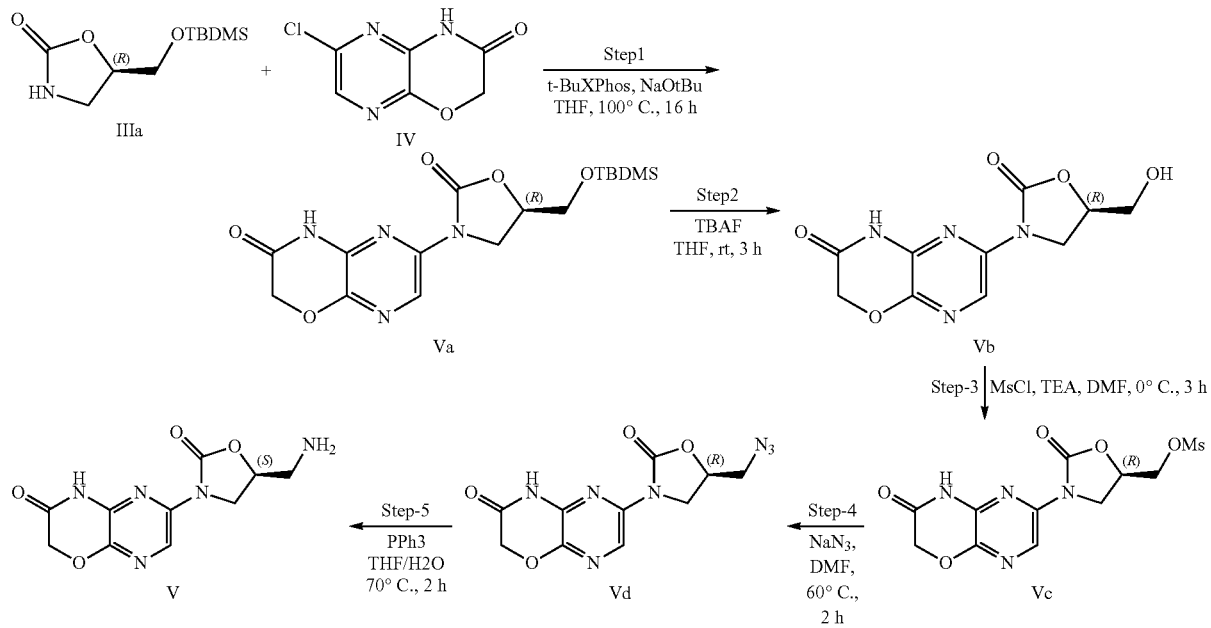

Step 1: (R)-6-(5-(((tert-butyldimethylsilyl)oxy)methyl)-2-oxooxazolidin-3-yl)-2H-pyrazino[2,3-b][1,4]oxazin-3(4H)-one (Va)

To a stirred solution of IV (2.5 g, 13.51 mmol) and IIa (3.43 g, 14.86 mmol) in dry 1,4-Dioxane (40 mL), were added t-butyl-X-Phos mesyl chloride complex (0.53 g, 0.67 mmol) and sodium tert-butoxide (1.94 g, 20.27 mmol) and degassed for 20 mins. Then, it was heated in sealed tube at 100° C. for 16 h. After completion of the reaction, reaction mixture was concentrated under reduced pressure. It was purified by column chromatography on silica gel (230-400 mesh, 25-30% ethyl acetate in pet ether) to afford Va (3 g, 59%).

LC_MS Calc. for $C_{16}H_{24}N4O_5Si$, 380.48, Observed 381.1 (M+1H);

1H NMR (400 MHz, DMSO-d$_6$): δ 11.61 (s, 1H), 8.37-8.35 (m, 1H), 4.85-4.79 (m, 3H), 4.12-4.06 (m, 1H), 3.89-3.74 (m, 3H), 0.84-0.71 (m, 9H), 0.03-0.00 (m, 6H).

Step 2: (R)-6-(5-(hydroxymethyl)-2-oxooxazolidin-3-yl)-2H-pyrazino[2,3-b][1,4]oxazin-3(4H)-one (Vb)

To a stirred solution of Va (3 g, 7.89 mmol) in TH (30 mL), cooled to 0° C., tert-butyl ammonium fluoride (1 M in THF) (15.8 mL, 15.78 mmol) was added dropwise and stirred at room temperature for 3 hours. After completion of the reaction, reaction mixture was quenched with water, extracted with ethyl acetate, dried over sodium sulphate and evaporated. The crude was purified by column chromatography on silica gel (230-400 mesh, 50-50% ethyl acetate in pet ether) to afford Vb (1.5 g, 71%).

LC_MS Calc. for $C_{10}H_{10}N_4O_5$, 266.21, Observed 267.1 (M+1H);

1H NMR (400 MHz, DMSO-d$_6$): δ 11.62 (s, 1H), 8.38 (s, 1H), 5.23-5.07 (m, 2H), 5.03 (s, 1H), 4.86-4.73 (m, 1H), 4.10-3.86 (m, 2H), 3.70-3.48 (m, 2H).

Step 3: (R)-(2-oxo-3-(3-oxo-3,4-dihydro-2H-pyrazino[2,3-b][1,4]oxazin-6-yl)oxazolidin-5-yl)methyl methanesulfonate (Vc)

To a stirred solution of Vb (1.5 g, 5.63 mmol) in dry DMF (15 mL), cooled to 0° C., Triethylamine (2.3 mL, 16.91 mmol) and mesyl chloride (0.69 mL, 8.45 mmol) were added and stirred at 25° C. for 2 h. After completion of the reaction, reaction mixture was quenched with water, the resultant solid was filtered, washed with pet ether and dried by vacuum to afford brown solid of Vc (1.2 g, 63%). LC_MS Calc. for $C_{11}H_{12}N_4O_7S$, 344.30, Observed 345.0 (M+1H);

$^1$H NMR (400 MHz, DMSO-d$_6$): δ 11.67 (s, 1H), 8.38 (s, 1H), 5.06-5.04 (m, 1H), 4.87 (s, 2H), 4.57-4.54 (m, 2H), 4.23-4.20 (m, 1H), 3.86-3.82 (m, 1H), 3.28 (s, 3H), 3.25-3.23 (m, 1H).

Step 4: (R)-6-(5-(azidomethyl)-2-oxooxazolidin-3-yl)-2H-pyrazino[2,3-b][1,4]oxazin-3(4H)-one (Vd)

To a stirred solution of Vc (1.2 g, 3.48 mmol) in DMF (12 mL), cooled to 0° C., sodium azide (0.56 g, 8.72 mmol) was added and heated at 65° C. for 3 h. After completion of the reaction, reaction mixture was quenched with water, the obtained solid was filtered, washed with pet ether and dried to afford the brown solid Vd (0.7 g, 70%).

LC_MS Calc. for $C_{10}H_9N_7O_4$, 291.23, Observed 290.1 (M−1H);

$^1$H NMR (400 MHz, DMSO-d$_6$): δ 11.66 (s, 1H), 4.94-4.86 (m, 3H), 4.18-4.13 (m, 1H), 3.81-3.75 (m, 3H).

Step 5 (S)-6-(5-(aminomethyl)-2-oxooxazolidin-3-yl)-2H-pyrazino[2,3-b][1,4]oxazin-3(4H)-one (V)

To a stirred solution of Vd (0.7 g, 2.40 mmol) in THF: MeOH (1:1) (40 ml) was added PPh3 (1.9 g, 7.21 mmol) at room temperature. The reaction mixture was heated at 70° C. for 3 h. After completion of the reaction by TLC, reaction mixture was cooled to room temperature, and was extracted with ethyl acetate (2×100 ml) for 2 times. Further theaqueous layer was concentrated and dried to afford V (0.3 g, 47%).

LC_MS Calc. for $C_{10}H_{11}N_5O_4$, 265.23, Observed 264.1 (M−1H);

$^1$H NMR (400 MHz, DMSO-$d_6$): δ 8.38 (s, 1H), 4.85 (s, 2H), 4.69-4.67 (m, 1H), 4.11-4.06 (m, 1H), 3.88-3.84 (m, 1H), 3.17 (s, 1H), 2.91-2.83 (m, 2H).

Synthesis of 2-((4-methyl-3-oxo-3,4-dihydropyrido[2,3-b]pyrazin-6-yl)oxy)acetaldehyde, Intermediate, VI Yield: 18 g, 72.5%

$^1$H NMR (400 MHz, DMSO-$d_6$): δ 6.69 (d, 1H, J=8 Hz), 6.65 (d, 1H, J=8 Hz), 5.78 (2H, s), 4.76 (2H, s).

LC_MS Calc. for $C_5H_6ClN_3$ 143.57; Obs. 144.2 [M$^+$+H]

Step-2: Synthesis of Ethyl (2-amino-6-chloropyridin-3-yl) Glycinate (VIb)

To a stirred solution of Va (18 g, 125.3 mmol) in dry DMF (180 mL) was added $K_2CO_3$ (24.22 g, 175.55 mmol) followed by the addition of ethylbromoacetate (16.7 mL, 150.4 mmol). The reaction mixture was heated to 100° C. for 6 h and cooled to rt, diluted with EtOAc (250 mL) and washed with water (2×200 mL). The organic layers were dried over sodium sulphate and concentrated to get the crude product Vb. The crude was taken to the next step without further purification. Yield: 12 g, 62%

$^1$H NMR (400 MHz, DMSO-$d_6$): δ 6.5-6.4 (m, 2H), 5.9 (m, 2H), 5.39-5.35 (m, 1H), 4.16-4.08 (m, 2H), 3.94-3.91 (m, 2H), 1.2-1.17 (m, 4H).

LC_MS: Calc. for $C_9H_{12}ClN_3O_2$ 229.66; Obs. 230.2 [M$^+$+H]

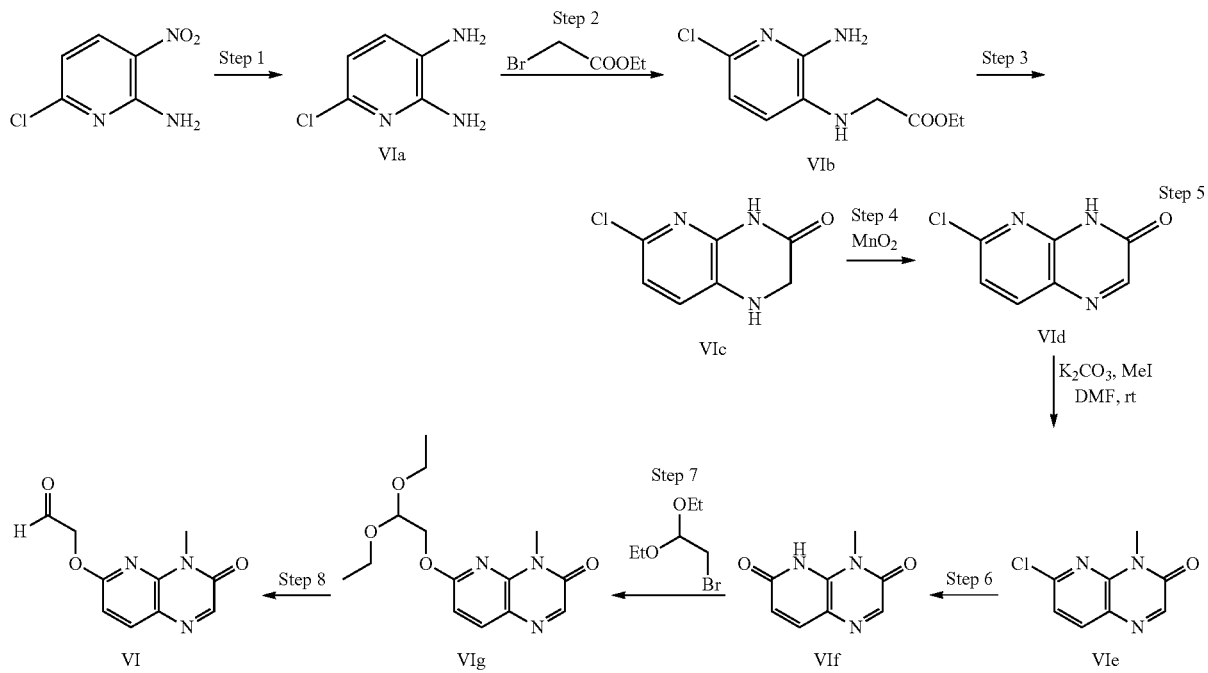

Step-1: Synthesis of 6-chloropyridine-2,3-diamine (VIa)

To a stirred solution of 2-amino-3-nitro-6-chloropyridine (30 g, 172.8 mmol) in EtOH (300 mL) and $H_2O$ (300 mL) was added $CaCl_2$) (23 g, 207.4 mmol) followed by the addition of Fe powder (22.8 g, 414.8 mmol). The resulting mixture was heated to 100° C. for 6 h. The reaction mixture was filtered through a celite bed. The filtrate was diluted with EtOAc (500 mL) and washed with water (2×250 mL). The organic layer was dried over sodium sulphate and concentrated to get the crude product. The crude was purified by column chromatography using silica gel (60-120 mesh) by eluting with 30% EtOAc in petroleum ether to afford pure product VIa as a brown solid.

Step-3: Synthesis of 6-chloro-1,4-dihydropyrido[2,3-b]pyrazin-3(2H)-one (VIc)

To a stirred solution of VIb (12 g, 52.2 mmol) in dry 1,4 dioxane (120 mL) was added NaH (0.62 g, 15.6 mmol). The resulting mixture was heated to 100° C. for 1 h. The reaction mixture was cooled to rt diluted with EtOAc (300 mL) and washed with water (2×150 mL). The organic layer was dried over sodium sulphate and concentrated to get the crude product. The crude was purified by column chromatography using silica gel (60-120 mesh) by eluting with 25% EtOAc in petroleum ether to afford pure product VIc as brown solid.

Yield: 7 g, 73.22%

UPLC-MS: Calc. for $C_7H_6ClN_3O$ 183.60; Obs. 184.0 [M$^+$+H].

Step-4: Synthesis of 6-chloropyrido [2,3-b] pyrazin-3(4H)-one (VId)

To a solution of VIc (7 g, 38.25 mmol) in 1,4-dioxane (70 mL) was added $MnO_2$ (36.5 g, 42.07 mmol) and heated to 100° C. for 6 h. The reaction mixture was filtered through a celite bed and washed with EtOAc (150 mL). The filtrate was concentrated to get the crude product VId. The crude was used for the next step without further purification. Yield: 6 g, 86%

$^1$H NMR (400 MHz, DMSO-$d_6$): δ 13.10 (brs, 1H), 8.26-8.23 (m, 2H), 7.45-7.42 (m, 1H).

LC_MS Calc. for $C_7H_4ClN_3O$ 181.58; Obs. 182.0 [M$^+$+H].

Step-5: Synthesis of 6-chloro-4-methylpyrido[2,3-b]pyrazin-3(4H)-one (VIe)

To a stirred solution of VId (1 g, 5.5 mmol) in dry DMF (20 mL) was added $K_2CO_3$ (0.91 g, 6.6 mmol) followed by the addition methyliodide (1.09 g, 7.7 mmol). The resulting mixture allowed to stir at room temperature for 2 h. The reaction mixture was diluted with EtOAc (30 mL) and washed with water (2×20 mL). The organic layer was dried over sodium sulphate and concentrated to get the crude product. The crude was purified by column chromatography using silica gel (60-120 mesh) by eluting with 20% EtOAc in petroleum ether to afford pure product VI e as yellow viscous liquid. Yield: 0.7 g, 65.4%

LC_MS Calc. for $C_8H_6ClN_3O$ 195.61; Obs. 196.0 [M$^+$+H].

$^1$H NMR (400 MHz, DMSO-$d_6$) δ 8.33 (s, 1H), 8.30 (d, 1H, J=8 Hz), 7.52 (d, 1H, J=8 Hz), 3.58 (s, 3H).

Step-6: Synthesis of 4-methylpyrido[2,3-b]pyrazine-3,6(4H,5H)-dione (VIf)

A stirred solution of VIe (0.7 g, 3.5 mmol) in dioxane (60 mL) and water (60 mL) was purged with $N_2$ for 10 min and to this was added t-BuXPhos Palladacycle (0.12 g, 0.17 mmol), Pd2(dba)$_3$ (0.065 g, 0.07 mmol) and KOH (0.39 g, 7.17 mmol). The reaction mixture was heated to 100° C. for 2 h and cooled to rt, diluted with EtOAc (50 mL) and washed with water (2×30 mL). The organic layer was dried over sodium sulphate and concentrated to afford the crude product VIf. The crude was used for the next step without further purification.

LC_MS Calc. for $C_8H_7N_3O_2$ 177.16; Obs. 176.0 [M-+H].

$^1$H NMR (400 MHz, DMSO-$d_6$) δ 11.92 (brs, 1H), 8.05 (d, 1H, J=8 Hz), 8.04 (s, 1H), 6.66 (d, 1H, J=8 Hz), 3.57 (s, 3H).

Step-7: Synthesis of 5-(2,2-diethoxyethyl)-4-methylpyrido[2,3-b]pyrazine-3,6(4H,5H)-dione (VIg)

To a stirred solution of VIf (0.5 g, 2.82 mmol) in dry DMSO (10 mL) was added $Cs_2CO_3$ (1.1 g, 3.33 mmol) followed by the addition of bromoacetaldehyde dimethylacetal (0.77 g, 3.95 mmol). The resulting mixture was heated to 80° C. for 12 h. The reaction mixture was cooled to room temperature, diluted with EtOAc (50 mL) and washed with water (2×25 mL). The organic layer was dried over sodium sulphate and concentrated to get the crude product. The crude was purified by column chromatography using silica gel (60-120 mesh) by eluting with 25% EtOAc in petroleum ether to afford pure product VIg as yellow viscous liquid. Yield: 0.42 g, 51%

LC_MS Calc. for $C_{14}H_{19}N_3O_4$ 293.32; Obs. 294.2 [M$^+$+H].

$^1$H NMR (400 MHz, DMSO-$d_6$) δ 8.13 (d, 1H, J=8 Hz), 8.12 (s, 1H), 6.85 (d, 1H, J=8 Hz), 4.90 (t, 1H, J=4 Hz), 4.38-4.36 (m, 2H), 3.71-3.62 (m, 2H), 3.6-3.51 (m, 5H), 1.15-1.0 (m, 6H).

Step-8: Synthesis of 2-(4-methyl-3,6-dioxo-4,6-dihydropyrido[2,3-b]pyrazin-5(3H)-yl)acetaldehyde (VI)

A solution of VIg (0.4 g, 1.3 mmol) in 1.5 N HCl (4 mL) was heated to 80° C. for 2 h. The reaction mixture was cooled to rt and diluted with EtOAc (20 mL) and washed with water (2×20 mL). The organic layer was dried over sodium sulphate and concentrated to get the crude product VI. The crude was used for the next step without further purification. Yield: 0.2 g, 64.5%.

LC_MS Calc. for $C_{10}H_9N_3O_3$ 219.20; Obs. 220.0 [M$^+$+H].

Synthesis of 2-((5-methyl-6-oxo-5,6-dihydropyrido[2,3-b]pyrazin-3-yl)oxy)acetaldehyde, Intermediate VII

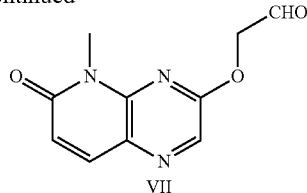

Step-1: Synthesis of 6-chloro-3-(2,2-diethoxyethoxy)pyrido[2,3-b]pyrazine (VIIa)

To a stirred solution of VId (25 g, 138.12 mmol) in dry DMF (400 mL) was added $K_2CO_3$ (57.18 g, 414.36 mmol) followed by the addition of bromoacetaldehyde diethylacetal (40.81 g, 207.18 mmol). The resulting mixture was heated to 90° C. for 24 h. The reaction mixture was diluted with EtOAc (500 mL) and washed with water (2×300 mL). The organic layer was dried over $Na_2SO_4$ and concentrated to get the crude product. The crude was purified by column chromatography on silica gel (60-120 mesh, 30% EtOAc in Pet. ether) to afford VIIa as yellow viscous liquid (18 gm, 44%).

LC_MS Calc. for $C_{13}H_{16}ClN_3O_3$ 297.74; Obs. 252.0 [$M^+$-OEt].

1H NMR (400 MHz, DMSO-$d_6$): δ 8.4-8.3 (m, 2H), 7.6-7.5 (m, 1H), 5.0-4.9 (m, 1H), 4.4-4.3 (m, 2H), 3.7-3.5 (m, 3H), 3.5-3.4 (m, 2H), 1.0-0.9 (m, 6H).

Step-2: Synthesis of 3-(2,2-diethoxyethoxy)pyrido[2,3-b]pyrazin-6(5H)-one (VIIb)

A stirred solution of VIIa 10.5 g, 35.353 mmol) in dioxane (105 mL) and water (105 mL) was purged with N2 gas for 10 min followed by addition t-BuXPhos-palladacycle (0.36 g, 0.50 mmol), $Pd_2(dba)_3$ (0.64 g, 0.707 mmol) and KOH (3.95 g, 70.707 mmol). The reaction mixture was heated to 100° C. for 2 h and cooled to rt, diluted with EtOAc (75 mL) and washed with water (2×50 mL). The organic layer was dried over sodium sulphate and concentrated to afford the crude product VIIb. The crude was used for the next step without further purification. Yield: 88.9%

LC_MS Calc. for $C_{13}H_{17}N_3O_4$ 279.3; Obs.234.1&235.1 (-OEt) [$M^+$+H].

1H NMR (400 MHz, DMSO-$d_6$): δ 12.0-11.9 (brs, 1H), 8.1-8.0 (m, 2H), 6.75-6.6 (m, 1H), 5.07-5.02 (m, 1H), 4.45-4.3 (m, 2H), 3.7-3.5 (m, 3H), 3.5-3.4 (m, 2H), 1.0-0.9 (m, 6H).

Step-3: Synthesis of 3-(2,2-diethoxyethoxy)-5-methylpyrido[2,3-b]pyrazin-6(5H)-one (VIIc)

To a stirred solution of VIIb (15 g, 53.76 mmol) in dry THF (150 mL), was added 1M solution of LHMDS in Hexane (161 mL, 161.3 mmol) under nitrogen atmosphere and stirred for 30 min at 0° C. Then methyl iodide (6.7 mL, 107.52 mmol) was added. The resulting mixture was allowed to stir at room temperature for 16 h. The reaction mixture was cooled to 0° C., and was quenched with $NH_4Cl$ solution. Further, dilution was done with EtOAc (300 mL), further to dilution two layers were separated, aqueous layer was extracted with Ethyl acetate (2×250 mL). The organic layer was washed with brine (200 mL), dried over sodium sulphate and concentrated to get the crude product. The crude was purified by column chromatography using Biotage Isolera (230-400 mesh) by eluting with 40-50% EtOAc in petroleum ether to afford pure product VIIc as brown colour viscous liquid.

Yield: 3 g, 19%

LC_MS Calc. for $C_{14}H_{19}N_3O_4$ 293.32; Obs. 294.2 [$M^+$+H].

$^1$H NMR (400 MHz, DMSO-$d_6$): δ 8.28 (s, 1H), 7.96 (d, J=9.60 Hz, 1H), 6.76 (d, J=9.60 Hz, 1H), 4.93-4.95 (m, 1H), 4.43-4.44 (m, 2H), 3.65-3.70 (m, 2H), 3.63 (s, 3H), 3.58-3.62 (m, 2H), 1.13-1.17 (m, 6H).

Step-4: Synthesis of 2-((5-methyl-6-oxo-5,6-dihydropyrido[2,3-b]pyrazin-3-yl)oxy)acetaldehydee (VII)

A solution of VIIc (3 g, 10.23 mmol) in dichloromethane (50 mL), was cooled to 0° C. and added Trifluoroacetic acid (15 mL). The reaction mixture was allowed to stir at rt for 2 h. The reaction mixture was diluted with Dichloromethane (100 mL) and washed with saturated sodium bicarbonate (100 mL) solution followed by brine (100 mL). The organic layer was dried over sodium sulphate and concentrated to get the crude product VII. The crude was used for the next step without further purification.

Yield: 1.7 g, 75%;

LC_MS Calc. for $C_{10}H_9N_3O_3$ 219.20; Obs. 220.0 [$M^+$+H].

Synthesis of (R)-6-(5-(aminomethyl)-2-oxooxazolidin-3-yl)-2H-pyrazino[2,3-b][1,4]oxazin-3(4H)-one (VIII)

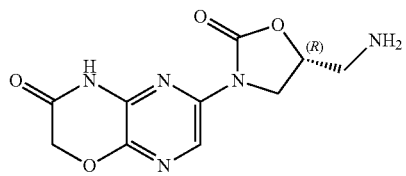

Synthesis of (R)-6-(5-(aminomethyl)-2-oxooxazolidin-3-yl)-2H-pyrazino[2,3-b][1,4]oxazin-3(4H)-one (WO2018225097), Intermediate VIII was synthesized using scheme and procedures analogues to Intermediate V involving (S)-5-(hydroxymethyl)oxazolidin-2-one (CAS: 97859-49-9) and 6-chloro-2H-pyrazino[2,3-b][1,4]oxazin-3(4H)-one (IV) as starting materials.

$^1$H NMR (400 MHz, DMSO-$d_6$): δ 8.37 (s, 1H), 4.84 (s, 2H), 4.70-4.66 (m, 2H), 4.11-4.07 (m, 1H), 3.87-3.82 (m, 1H), 2.91-2.85 (m, 3H), 2.83-2.79 (m, 1H). LC-MS Calc. for $C_{10}H_{11}N_5O_4$, 265.23, Observed 266.1 ($M^+$+H).

Synthesis of 6-chloro-2H-pyrazino[2,3-b][1,4]thiazin-3(4H)-one, 1Xa

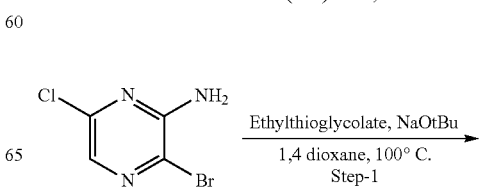

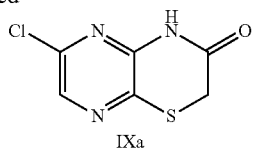

IXa

To a stirred solution of 3-bromo-6-chloropyrazin-2-amine I (10 g, 0.0479 mol) in 1,4-dioxane (1.5 L) at room temperature under nitrogen atmosphere was added sodium tert-butoxide (14.75 g, 0.1535 mol) and stirred for 30 minutes. Then ethyl thioglycolate (11.53 g, 0.0959 mol) was added in dropwise over a period of 30 minutes at room temperature. The resulting mixture was heated to 100° C. and stirred for 2 hours. The progress of the reaction was monitored by TLC.

After that, the reaction mixture was cooled to room temperature and concentrated under reduced pressure to remove the dioxane. The residue obtained was diluted with water (750 mL) and neutralized using HCl (1.5 N). The precipitated solid was filtered out and dried to get the compound VIa as an off white solid. Yield: 6 g, 62.5%;

LC_MS: Calc. for $C_6H_4ClN_3Os$: 201.63; Obs.: 199.9 [M−1H]. $^1$H-NMR (400 MHz, DMSO-$d_6$): δ 11.54 (s, 1H), 8.25 (s, 1H), 3.83 (s, 2H).

Synthesis of (S)-5-(aminomethyl)-3-(3-oxo-3,4-dihydro-2H-pyrazino[2,3-b][1,4]thiazin-6-yl)oxazolidin-2-one (Intermediate IX)

Step 1: (R)-5-(hydroxymethyl)-3-(3-oxo-3,4-dihydro-2H-pyrazino[2,3-b][1,4]thiazin-6-yl)oxazolidin-2-one (IXb)

To a stirred solution of compound IXa (6 g, 0.0297 mol) and (R)-5-(hydroxymethyl)oxazolidin-2-one (CAS: 97859-

49-9, 3.83 g, 0.0327 mol) in 1,4-dioxane (100 mL) was added sodium tert-butoxide (4.29 g, 0.0446 mol) at room temperature. The resulting mixture was degassed with a stream of nitrogen for 10 minutes. Then t-butyl-X-Phos Palladacycle (1.18 g, 0.0014 mol) was added at room temperature and again degassed with nitrogen for 5 minutes. The resulting mixture was then heated to 100° C. and stirred for 5 hours. After that, the reaction mixture was cooled to room temperature and concentrated in vacuo. The residue obtained was diluted with water (50 mL), neutralized with aqueous HCl (1.5 N, pH-7). The solid precipitated out was filtered and washed with diethyl ether, dried under vacuo to get compound IXb as brown solid. Yield: 4 g (crude), which was taken for the next step without any further purification. LC_MS: Calc. for $C_{10}H_{10}N_4O_4S$: 282.27; Obs.: 283.2 [M+H]$^+$. $^1$H NMR (300 MHz, DMSO-$d_6$): δ 11.24 (s, 1H), 8.24 (s, 1H), 5.27-5.24 (m, 1H), 4.80-4.76 (m, 1H), 4.09 (t, J=9.36 Hz, 1H), 3.91-3.87 (m, 1H), 3.78-3.68 (m, 3H), 3.60-3.57 (m, 1H).

Step 2: (R)-(2-oxo-3-(3-oxo-3,4-dihydro-2H-pyrazino[2,3-b][1,4]thiazin-6-yl)oxazolidin-5-yl)methyl Methanesulfonate (IXc)

To a stirred solution of IXb (4 g, 0.0141 mol) in dry DMF (40 mL) at 0° C. under nitrogen atmosphere were added triethylamine (5.5 mL, 0.0425 mol) and mesyl chloride (2.43, 0.0215 mol) successively. The reaction mixture was then warmed to room temperature and stirred for 2 h. After

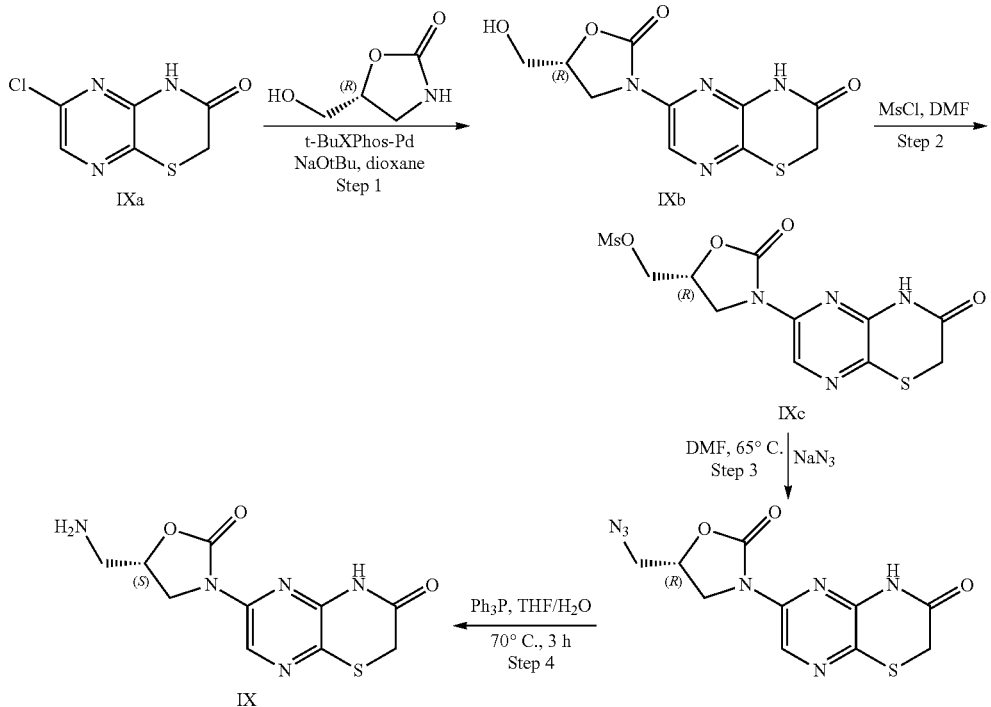

that the reaction mixture was quenched with water, the solid formed was filtered, washed with petroleum ether and dried to get compound IXc as a brown solid (3 g, crude), which was taken for the next step without any further purification. LC_MS: Calc. for $C_{11}H_{12}N_4O_6S_2$: 360.36; Obs.: 361.00 [M+H]+.

Step 3: (R)-5-(azidomethyl)-3-(3-oxo-3,4-dihydro-2H-pyrazino[2,3-b][1,4]thiazin-6-yl)oxazolidin-2-one (IXd)

To a stirred solution of IXc (3.0 g, 0.0083 mol) in DMF (30 mL) at 0° C. under nitrogen atmosphere was added sodium azide (2.16 g, 0.033 mol). The reaction mixture was then heated to 65° C. and stirred for 3 h. After that, reaction mixture was quenched with water, the solid obtained was filtered, washed with petroleum ether and dried to get compound IXd as a brown solid (1.7 g, 66.66%). LC_MS: Calc. for $C_{10}H_9N_7O_3S$: 307.29; Obs.: 307.9 [M+H]$^+$.

Step 4: (S)-5-(aminomethyl)-3-(3-oxo-3,4-dihydro-2H-pyrazino[2,3-b][1,4]thiazin-6-yl)oxazolidin-2-one (IX)

To a stirred solution of compound IXd (1.7 g, 0.0055 mol) in a mixture of THF: $H_2O$ (1:1) (80 mL) under nitrogen atmosphere was added PPh3 (4.34 g, 0.0165 mol) at room temperature. The reaction mixture was heated to 70° C. and stirred for 3 hours. After completion of the reaction by TLC, the reaction mixture was cooled to room temperature and extracted with ethyl acetate (2×100 mL). The aqueous layer was separated and concentrated in vacuo to get compound IX (0.9 g, 58.06%). LC_MS: Calc. for $C_{10}H_{11}N_5O_3S$: 281.29; Obs.: 282.1 [M+H]$^+$.

Synthesis of 2-((7-Fluoro-4-methyl-3-oxo-3,4-dihydropyrido[2,3-b]pyrazin-6-yl)oxy)acetaldehyde (Intermediate X)

with water, extracted with EtOAc (2×50 mL) and washed with brine solution (25 mL). The organic layer was dried over sodium sulphate and concentrated to get the crude product. The crude was then purified by column chromatography using silica gel (60-120 mesh) by eluting with 20% EtOAc in petroleum ether to afford Xaas a brown solid. Yield: 0.15 g, 28.32%.
LC_MS: Calc. for $C_{14}H_{18}FN_3O_4$ 311.31; Obs. 312.1 [M$^+$+H].

Step-2: Synthesis of 2-((7-fluoro-4-methyl-3-oxo-3,4-dihydropyrido[2,3-b]pyrazin-6-yl)oxy)acetaldehyde (X)

To a stirred solution of Xa (0.15 g, 0.48 mmol) in dichloromethane (2 mL), cooled to 0° C., was added TFA (0.5 mL) at 0° C. under nitrogen atmosphere. The reaction mixture was then warmed to room temperature and stirred for 2 h. After completion of reaction, reaction mixture was cooled and quenched with 10% sodium bicarbonate solution extracted with dichloromethane. The organic layer was washed with brine (20 mL), dried over $Na_2SO_4$ and concentrated under reduced pressure. The crude product obtained was triturated with petroleum ether to afford X (0.1 g). The crude product was as such used for next step without further purification.
LC_MS Calc. for $C_{10}H_8FN_3O_3$ 237.19; Obs. 238.1 [M$^+$+H].

Synthesis of 2-((7-Chloro-4-methyl-3-oxo-3,4-dihydropyrido[2,3-b]pyrazin-6-yl)oxy)acetaldehyde (Intermediate XI)

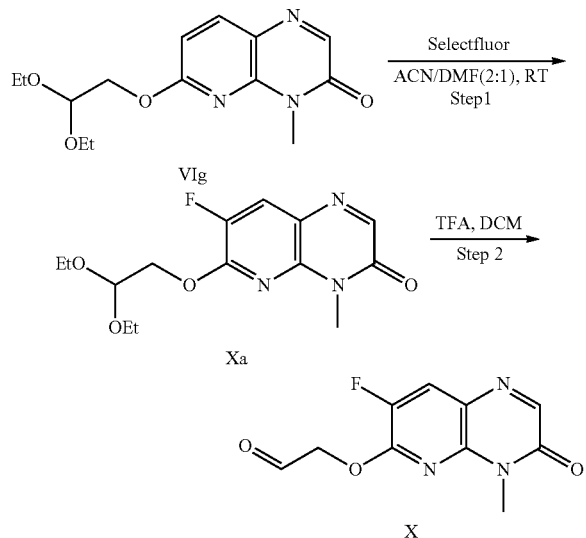

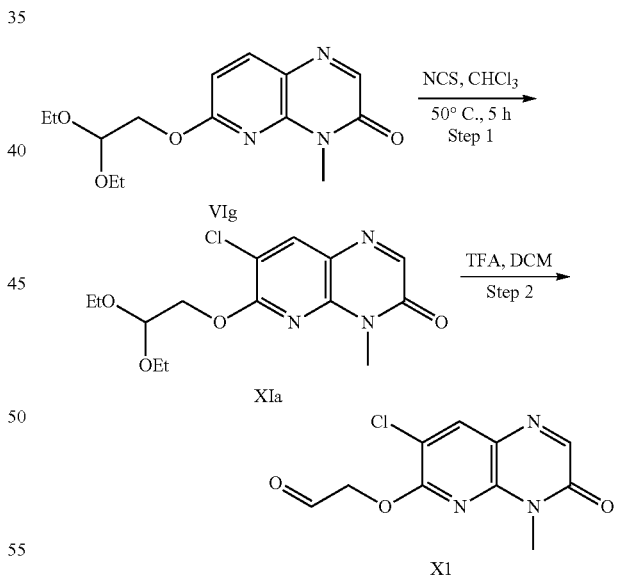

Step-1: Synthesis of 6-(2,2-diethoxyethoxy)-7-fluoro-4-methylpyrido[2,3-b]pyrazin-3(4H)-one (Xa)

To a stirred solution of VIg (0.5 g, 1.70 mmol) in a mixture of dry acetonitrile and DMF (2:1) (10 mL) was added selectfluor (1.6 g, 5.11 mmol) at room temperature under nitrogen atmosphere. The resulting mixture was continued to stir at room temperature for 24 hours. After completion of the reaction, reaction mixture was diluted Step-1: Synthesis of 7-chloro-6-(2,2-diethoxyethoxy)-4-methylpyrido[2,3-b]pyrazin-3(4H)-one (XIa)

To a stirred solution of VIg (1.0 g, 3.41 mmol) in dry CHC13 (20 mL) was added NCS (0.5 g, 3.75 mmol) at 0° C. The resulting mixture was stirred at RT for 5 h. The reaction mixture was diluted with water, extracted with DCM (2×50 mL) and washed with brine solution (25 mL).

The organic layer was dried over sodium sulphate and concentrated to get the crude product. The crude was purified by column chromatography using silica gel (60-120 mesh) by eluting with 15% EtOAc in petroleum ether to afford the product XIa as a pale brown solid. Yield: 0.3 g, 27%.

$^1$H NMR (400 MHz, DMSO-$d_6$): δ 8.41 (s, 1H), 8.17 (s, 1H), 4.95-4.93 (m, 1H), 4.46-4.44 (d, 2H), 3.74-3.68 (m, 2H), 3.64-3.58 (m, 5H), 1.16-1.2 (m, 6H). LC_MS: Calc. for $C_{14}H_{15}ClN_3O_4$ 327.77; Obs. 328.1 [M$^+$+H].

Step-2: Synthesis of 2-((7-chloro-4-methyl-3-oxo-3,4-dihydropyrido[2,3-b]pyrazin-6-yl)oxy)acetaldehyde (XI)

To a mixture of XIa (0.3 g, 0.9174 mmol) in (DCM, 20 mL) was cooled to 0° C. was added TFA (1.5 mL). The reaction mixture was stirred at room temperature for 2 h. Reaction mixture cooled and quenched with 10% sodium bicarbonate solution extracted with DCM The organic layer was washed with brine (10 mL), dried over $Na_2SO_4$ and concentrated under reduced pressure. The crude was triturated with petroleum ether to afford crude XI (0.15 g) and as such used for next step without further purification. LC_MS Calc. for $C_{10}H_8ClN_3O_3$ 253.64; Obs. 254.1 [M$^+$+H].

Synthesis of 2-((4-Ethyl-3-oxo-3,4-dihydropyrido[2,3-b]pyrazin-6-yl)oxy)acetaldehyde (Intermediate XII)

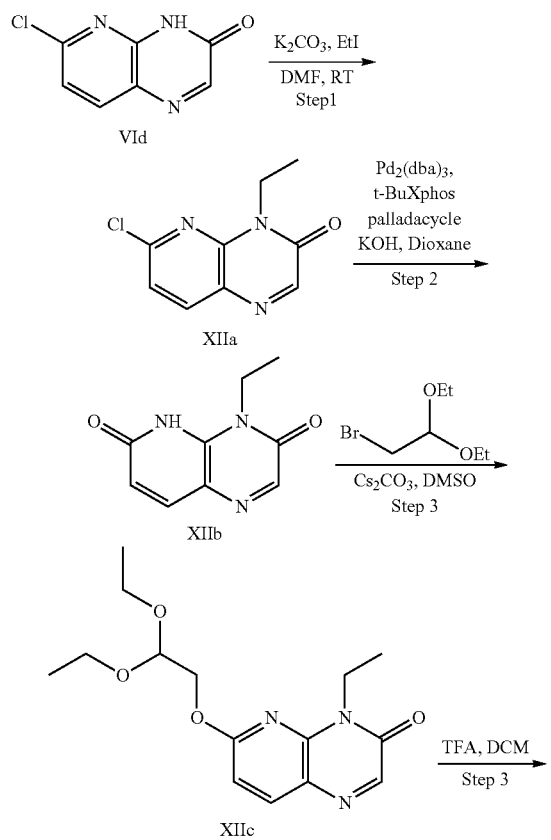

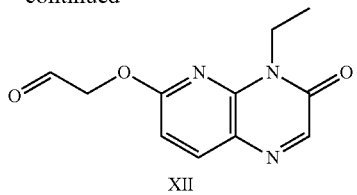

Step-1: Synthesis of 6-chloro-4-ethylpyrido[2,3-b]pyrazin-3(4H)-one (XV)

To a stirred solution of VId (5 g, 27.54 mmol) in dry DMF (100 mL) at 0° C. under nitrogen atmosphere were added $K_2CO_3$ (5.34 g, 38.56 mmol) and ethyl iodide (6.44 g, 41.31 mmol) successively. The resulting mixture warmed to room temperature and stirred for 2 hours. After completion of the reaction, the reaction mixture was diluted with EtOAc (80 mL) and washed with water (2×50 mL). The organic layer was dried over sodium sulphate and concentrated to get the crude product. It was purified by column chromatography using silica gel (60-120 mesh) by eluting with 20% EtOAc in petroleum ether to afford pure product XIIa as a yellow viscous liquid. Yield: 3.7 g, 64.9%.

$^1$H NMR (400 MHz, DMSO-$d_6$): δ 8.32 (s, 1H), 8.32 (d, 1H, J=10.8 Hz), 7.53 (d, 1H, J=10.8 Hz), 4.28 (m, 2H), 1.24 (t, J=7.2 Hz, 3H).

Step-2: Synthesis of 4-ethylpyrido[2,3-b]pyrazine-3,6(4H,5H)-dione (XIIb)

To a stirred solution of XIIa (3.7 g, 17.70 mmol) in a mixture of dioxane (80 mL)/water (40 mL) was purged with $N_2$ gas for 10 minutes and to this was added t-BuXPhos Palladacycle (0.48 g, 0.531 mmol), Pd$_2$(dba)$_3$ (0.32 g, 0.354 mmol) and KOH (1.98 g, 35.4 mmol) at room temperature. The reaction mixture was heated at 100° C. for 2 h. After completetion of reaction, the reaction mixture was cooled to room temperature, diluted with EtOAc (100 mL) and washed with water (2×50 mL). The organic layer was dried over sodium sulphate and concentrated to afford the XIIb (crude product, 2.7 g). The crude product was used for the next step without further purification.

$^1$H NMR (400 MHz, DMSO-$d_6$): δ 11.90 (brs, 1H), 8.05 (m, 2H), 6.69 (d, 1H, J=11.2 Hz), 4.31 (m, 2H), 1.23 (m, 3H). LC_MS Calc. for $C_9H_9N_3O_2$, 191.19; Obs. 192.0 [M$^+$+H].

Step-3: Synthesis of 6-(2,2-diethoxyethoxy)-4-ethylpyrido[2,3-b]pyrazin-3(4H)-one (XIIc)

To a stirred solution of XIIb (2.7 g, 14.13 mmol) in dry DMSO (30 mL) were added at room temperature under nitrogen atmosphere $Cs_2CO_3$ (5.98 g, 18.37 mmol) and bromoacetaldehyde dimethylacetal (4.15 g, 21.19 mmol) at room temperature. The resulting mixture was heated at 90° C. for 16 hours. After completion of the reaction, reaction mixture was cooled to room temperature, diluted with EtOAc (150 mL) and washed with water (2×50 mL). The organic layer was dried over sodium sulphate and concentrated to get the crude product. The crude was purified by column chromatography using silica gel (60-120 mesh) by eluting with 25% EtOAc in petroleum ether to afford pure product XIIc as pale brown solid. Yield: 2.0 g, 46.51%.

¹H NMR (400 MHz, DMSO-d₆): δ 8.16 (d, 1H, J=8.8 Hz), 8.12 (s, 1H), 6.88 (d, 1H, J=8.8 Hz), 4.92 (t, 1H), 4.38-4.36 (m, 2H), 4.31-4.29 (m, 2H), 3.72-3.66 (m, 2H), 3.61-3.53 (m, 2H), 1.28-1.25 (m, 3H), 1.16-1.11 (m, 6H). LC_MS Calc. for C$_{15}$H$_{21}$N$_3$O$_4$, 307.35; Obs. 308.1 [M$^+$+H].

Step-4: Synthesis of 2-((4-ethyl-3-oxo-3,4-dihydro-pyrido[2,3-b]pyrazin-6-yl)oxy)acetaldehyde (XII)

To a mixture of XIIc (0.5 g, 1.62 mmol) in dichloromethane (5 mL), cooled to 0° C., was added TFA (0.25 mL) in dropwise. The reaction mixture was warmed to room temperature and stirred for 2 h. After completion of the reaction, reaction mixture was cooled and quenched with 10% sodium bicarbonate solution and extracted with dichloromethane. The organic layer was washed with brine (50 mL), dried over Na$_2$SO$_4$ and concentrated under reduced pressure. The crude obtained was triturated with petroleum ether to afford XII (crude, 0.25 g) and as such used for the next step without further purification.

LC_MS Calc. for C$_{11}$H$_{11}$N$_3$O$_3$, 233.23; Obs. 234.1 [M$^+$+H].

Compound 1: 6-(5-(2-((2-((4-methyl-3-oxo-3,4-dihydropyrido[2,3-b]pyrazin-6-yl)oxy)ethyl)amino)ethyl)-2-oxooxazolidin-3-yl)-2H-pyrido[3,2-b][1,4]oxazin-3(4H)-one

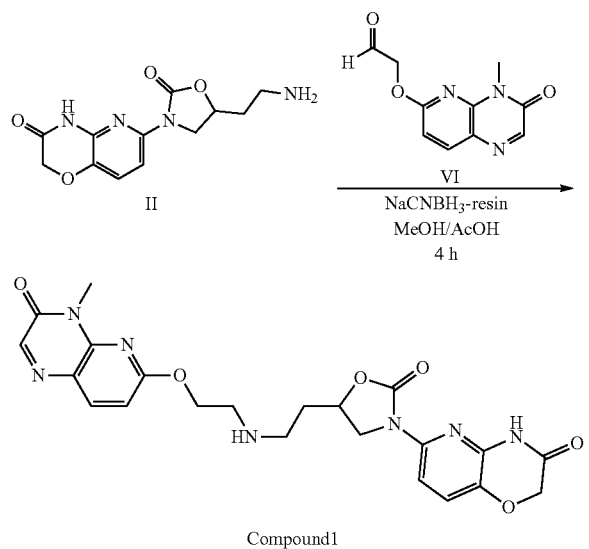

Compound1

To a mixture of VI (0.2 g, 0.91 mmol) and amine, II (0.3 g, 1.09 mmol) in dry MeOH (6 mL) and DCM (6 mL) was added AcOH (0.1 mL) and allowed to stir for 5 h. To this was added sodium cyanoborohydride resin (0.73 g, 1.82 mmol) and stirred for 15 min. Then the reaction mixture was filtered and the filtrate was concentrated to remove MeOH. The residue diluted with DCM (20 mL) and washed with water (2×20 mL). The organic layers were dried over sodium sulphate and concentrated to get the crude product. The crude was purified by column chromatography using silica gel (60-120 mesh) by eluting with 3% MeOH in DCM to afford pure product as Compound 1 (60 mg) as orange solid. Yield: 60 mg, 14%.

LC_MS calculated for C$_{22}$H$_{23}$N$_7$O$_6$ 481.47; Observed=482.2 [M$^+$+H]. ¹H NMR (400 MHz, DMSO-D$_6$) δ 8.13 (d, 1H, J=8 Hz), 8.12 (s, 1H), 7.58 (d, 1H, J=8 Hz), 7.42 (d, 1H, J=8 Hz), 6.83 (d, 1H, J=8 Hz), 4.79-4.76 (m, 1H), 4.61 (s, 2H), 4.49-4.46 (m, 2H), 4.23-4.18 (m, 1H), 3.79-3.74 (m, 1H), 3.62 (s, 3H), 2.99-2.95 (m, 2H), 2.74-2.71 (m, 2H), 1.9 (m, 3H), 1.2 (m, 1H).

HPLC: RT 6.46 min. Phenomenex Gemini Column (NX-C18 150×4.6)mm 3µ, Mobile Phase A:10 mM NH$_4$OAc/H$_2$O, Mobile Phase B: Acetonitrile.

Compound 2: 6-(5-(2-((2-((5-methyl-6-oxo-5,6-dihydropyrido[2,3-b]pyrazin-3-yl)oxy)ethyl)amino)ethyl)-2-oxooxazolidin-3-yl)-2H-pyrido[3,2-b][1,4]oxazin-3(4H)-one

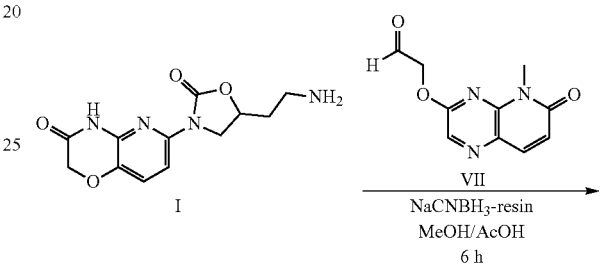

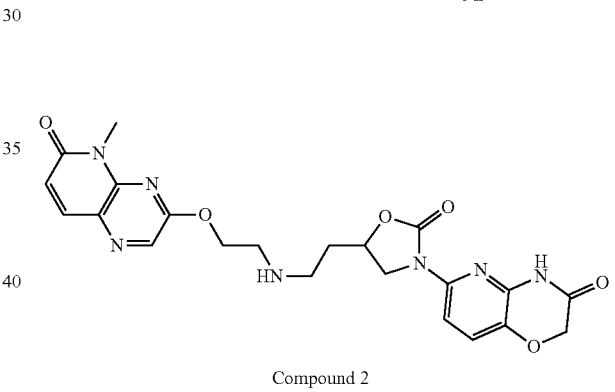

Compound 2

To a mixture of VII (0.8 g, 3.6 mmol) and amine I (1.22 g, 4.3 mmol) in dry MeOH (13 mL) and DCM (13 mL) was added AcOH (0.5 mL) and allowed to stir for 5 h. To this was added sodiumcyanoborohydride resin (2.92 g, 7.3 mmol) and stirred for 15 min. The reaction mixture was filtered and the filtrate was concentrated. The residue diluted with DCM (50 mL) and washed with water (2×30 mL). The organic layer was dried over sodium sulphate and concentrated to get the crude product. The crude was purified by column chromatography using silica gel (60-120 mesh) by eluting with 5% MeOH in DCM to afford the title compound as an orange solid. Yield: 0.5 g, 28%.

¹H NMR (400 MHz, DMSO-D$_6$): δ 11.23 (s, 1H, exchangeable), 8.79 (m, 1H, exchangeable), 8.22-8.15 (m, 2H), 7.58 (d, 1H, J=8 Hz), 7.44 (d, 1H, J=8 Hz), 6.85 (d, 1H, J=8 Hz), 4.8-4.75 (m, 1H), 4.65-4.6 (m, 4H), 4.25 (m, 1H), 3.8-3.74 (m, 1H), 3.63 (s, 3H), 3.5-3.4 (m, 2H), 3.2-3.1 (m, 2H), 2.2-2.0 (m, 2H). LC_MS: Calc. for C$_{22}$H$_{23}$N$_7$O$_6$ 481.47; Obs. 482.0 [M$^+$+H].

Compound 3: (S)-6-(5-(((2-((4-methyl-3-oxo-3,4-dihydropyrido[2,3-b]pyrazin-6-yl)oxy)ethyl)amino)methyl)-2-oxooxazolidin-3-yl)-2H₁-pyrido[3,2-b][1,4]oxazin-3(4H)-one Compound 4: (R)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrido[3,2-b][1,4]oxazin-3(4H)-one

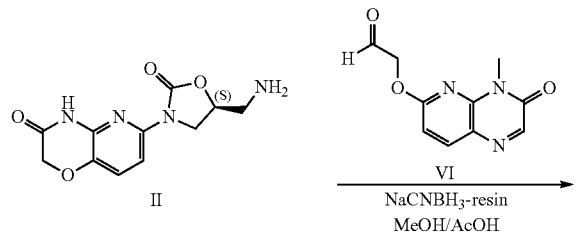

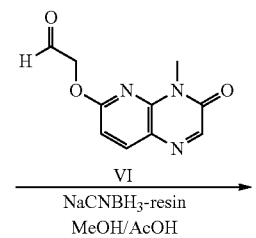

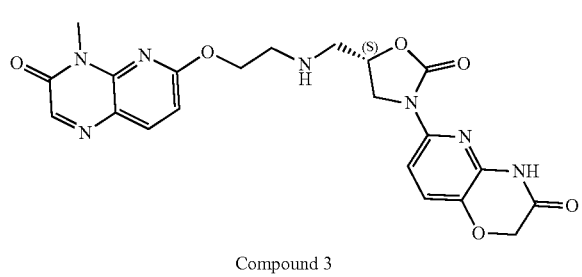

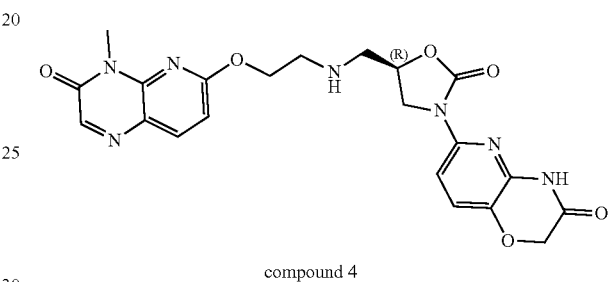

Compound 3 compound 4

To a mixture of aldehyde, VI (0.3 g, 1.37 mmol) and amine, II (0.45 g, 1.64 mmol) in dry methanol (20 mL) and dichloromethane (20 mL) was added AcOH (0.10 mL) and allowed to stir for 16 hours at room temperature. To this was added MP-cyanoborohydride resin (1.09 g, 2.73 mmol) and stirred for another 15 minutes at room temperature. The reaction mixture was filtered and the filtrate was concentrated under reduced pressure. The residue was diluted with dichloromethane (50 mL) and washed with saturated aqueous 10% NaHCO₃ solution and brine (2×15 mL). The organic layer was dried over Na₂SO₄ and concentrated under reduced pressure to get the crude product, which was purified by column chromatography using silica gel (230-400 mesh) eluting with 4% methanol in dichloromethane to afford the title compound (Compound 3) as an off-white solid (0.180 g, 30%).

$^1$H NMR (400 MHz, DMSO-d$_6$): δ 11.18 (brs, 1H), 8.11-8.09 (m, 2H), 7.57 (d, J=8.8 Hz, 1H), 7.40 (d, J=8.8 Hz, 1H), 6.81 (d, J=8.4 Hz, 1H), 4.75-4.72 (m, 1H), 4.61 (s, 2H), 4.49-4.46 (m, 2H), 4.14-4.09 (m, 1H), 3.88-3.84 (m, 1H), 3.60 (s, 3H), 3.03-2.91 (m, 4H);

LC_MS: Calc. for C$_{21}$H$_{21}$N$_7$O$_6$ 467.44; Obs. 468.2 [M+H]$^+$.

HPLC: 96.21%; 8.03 min; HPLC Column: Atlantis dC18 (250*4.6) mm 5 μm, Mobile Phase A: 0.1% TFA in water, Mobile Phase B: Acetonitrile.

Chiral SFC: Retention time: 2.44 min; Column: YMC Amylose-SA, co-solvent: 0.5% DEA in IPA, Flow rate: 5 mL/min, Injected Volume: 15 L, Outlet Pressure: 100 bar, Temperature: 35° C.

Compound 4 was synthesized from intermediate III and Intermediate VI using procedure similar to Compound 3.

$^1$H NMR (400 MHz, DMSO-d6): δ 11.18 (brs, 1H), 8.11-8.09 (m, 2H), 7.57 (d, J=8.8 Hz, 1H), 7.40 (d, J=8.8 Hz, 1H), 6.81 (d, J=8.4 Hz, 1H), 4.75-4.72 (m, 1H), 4.61 (s, 2H), 4.49-4.46 (m, 2H), 4.14-4.09 (m, 1H), 3.88-3.84 (m, 1H), 3.60 (s, 3H), 3.03-2.91 (m, 4H);

LC_MS: Calc. for C$_{21}$H$_{21}$N$_7$O$_6$ 467.44; Obs. 468.0 [M+H]$^+$.

HPLC: 96.32%; 8.04 min; HPLC Column: Atlantis dC18 (250*4.6) mm 5 μm, Mobile Phase A: 0.1% TFA in water, Mobile Phase B: Acetonitrile Chiral SFC: Retention time (RT): 3.99 min (isomer-I); Column: YMC Amylose-SA, co-solvent: 0.5% DEA in IPA, Flow rate: 5 mL/min, Injected Volume: 15 L, Outlet Pressure: 100 bar, Temperature: 35° C.

Compound 5: (S)-6-(5-(((2-((5-methyl-6-oxo-5,6-dihydropyrido[2,3-b]pyrazin-3-yl)oxy)ethyl)amino)methyl)-2-oxooxazolidin-3-yl)-2H₁-pyrido[3,2-b][1,4]oxazin-3(4H)-one

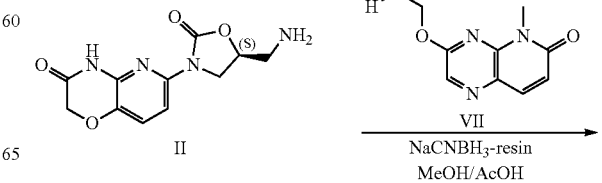

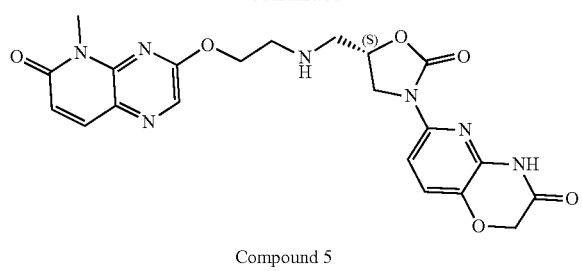

Compound 5

Compound 5 was synthesized from intermediate II and Intermediate VII using procedure similar to Compound 3. Yield (0.03 gm, 16%): $^1$H NMR (400 MHz, DMSO-d$_6$): δ11.17 (s, 1H), 8.17-8.14 (d, J=9.64 Hz, 2H), 7.92-7.90 (d, J=9.64 Hz, 1H), 7.58-7.55 (d, J=8.60 Hz, 1H), 7.41-7.39 (d, J=8.64 Hz, 1H), 6.72-6.69 (d, J=9.68 Hz, 1H), 4.76-4.72 (m, 1H), 4.60 (s, 2H), 4.53-4.51 (m, 2H), 4.14-4.10 (m, 1H), 3.88-3.84 (m, 1H), 3.61 (s, 3H), 3.0 (m, 2H), 2.95 (m, 2H);

LC_MS Calc. for $C_{21}H_{21}N_7O_6$ 467.16; Obs. 468.2 & 469.2 [M$^+$+H].

Compound 6: (R)-6-(5-(((2-((5-methyl-6-oxo-5,6-dihydropyrido[2,3-b]pyrazin-3-yl)oxy)ethyl)amino)methyl)-2-oxooxazolidin-3-yl)-2H-pyrido[3,2-b][1,4]oxazin-3(4H)-one

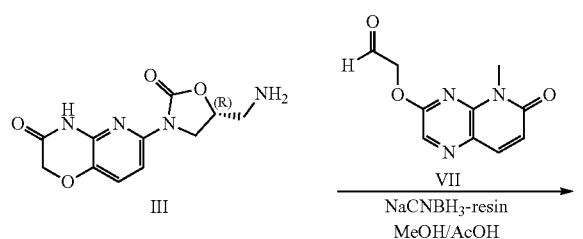

Compound 6

Compound 6 was synthesized from intermediate III and Intermediate VII using procedure similar to Compound 3.

Yield: 0.9 g, 24%; $^1$H NMR (400 MHz, DMSO-d$_6$): δ 11.15 (s, 1H), 8.17-8.14 (d, J=9.64 Hz, 2H), 7.92-7.90 (d, J=9.64 Hz, 1H), 7.57-7.55 (d, J=8.60 Hz, 1H), 7.40-7.38 (d, J=8.64 Hz, 1H), 6.72-6.69 (d, J=9.68 Hz, 1H), 4.76-4.72 (m, 1H), 4.60 (s, 2H), 4.53-4.51 (m, 2H), 4.14-4.10 (m, 1H), 3.88-3.84 (m, 1H), 3.61 (s, 3H), 3.0 (m, 2H), 2.95 (m, 2H); LC_MS Calc. for $C_{21}H_{21}N_7O_6$ 467.16; Obs. 468.2 & 469.2 [M$^+$+H].

Compound 7: (S)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrazino[3,2-b][1,4]oxazin-3(4H)-one

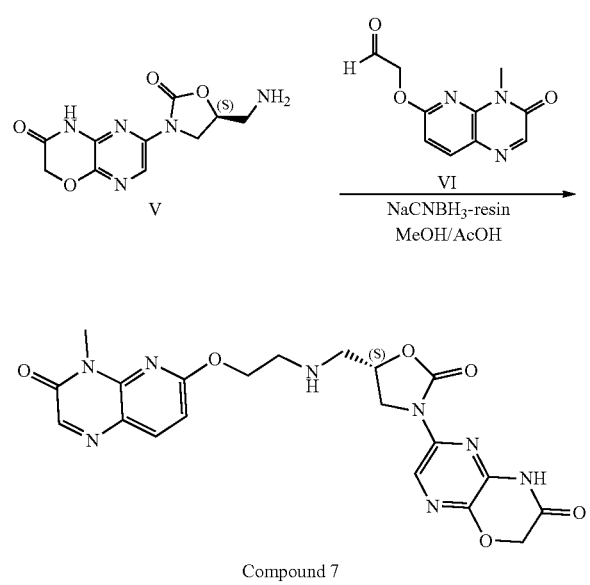

Compound 7

To a stirred suspension of VI (0.2 g, 0.9 mmol), amine V (0.24 g, 0.9 mmol) in MeOH: DCM (1:1, 50 ml), glacial acetic acid (0.2 mL) was added and stirred at RT for 16 h. Then, cyano borohydride resin (0.68 g, 1.36 mmol) was added and stirred at RT for 15 min. After completion of the reaction, filtered to remove the resin and the filtrate was concentrated in reduced pressure to get the crude. The crude was purified by peparative HPLC chromatography to afford the title compound as formate salt (pale yellow amorphous powder, 0.06 g, 15%).

$^1$H NMR (400 MHz, DMSO-d$_6$) δ 11.59 (s, br, 1H), 8.35 (s, 1H), 8.15-8.09 (m, 3H), 6.81 (d, 1H, J=8.8 Hz), 4.86 (s, 3H), 4.49-4.48 (m, 2H), 4.11-4.09 (m, 1H), 3.85-3.78 (m, 1H), 3.69 (s, 3H), 3.04-2.96 (m, 4H).

LC_MS Calc. for $C_{20}H_{20}N_8O_6$ is 468.43; Obs. 469.1 [M$^+$+H].

Compound 8: (R)-6-(5-(((2-((4-methyl-3-oxo-3,4-dihydropyrido[2,3-b]pyrazin-6-yl)oxy)ethyl)amino)methyl)-2-oxooxazolidin-3-yl)-2H$_1$-pyrazino[2,3-b][1,4]oxazin-3(4H)-one

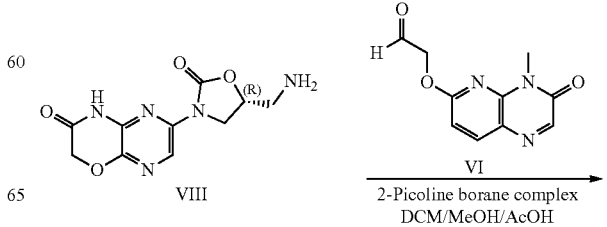

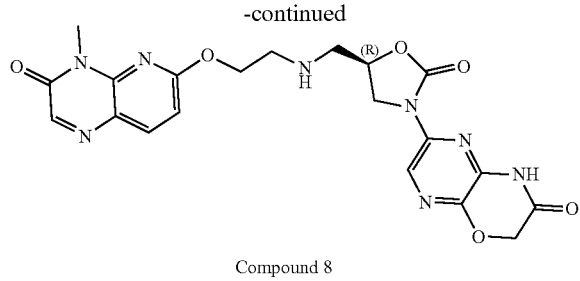

Compound 8

To a mixture of compound VI (0.2 g, 0.916 mmol) and amine VIII (0.243 g, 0.916 mmol) in a mixture of dry methanol (20 mL) and dichloromethane (20 mL) was added AcOH (0.40 mL) and allowed to stir for 16 hours at room temperature. To this was added 2-picoline borane complex (0.058 g, 0.549 mmol) and stirred for another 10 minutes at room temperature. The reaction mixture was quenched with 1% HCOOH in water and concentrated under reduced pressure to get the crude product. The obtained crude product was further purified by column chromatography using silica gel (230-400 mesh) eluting with 6% methanol in dichloromethane to afforded the title compound (Compound 8) as formate salt (white amorphous powder, 0.120 g, 28.80%).

$^1$H NMR (400 MHz, DMSO-D$_6$): δ 11.68 (brs, 1H), 8.35 (s, 1H), 8.14-8.09 (m, 3H), 6.80 (d, J=8.4 Hz, 1H), 4.85-4.80 (m, 3H), 4.48 (s, 2H), 4.09 (s, 1H), 3.82 (s, 1H), 3.60 (s, 3H), 3.05-2.97 (m, 4H). LC_MS: Calc. for C$_{20}$H$_{20}$N$_8$O$_6$ 468.43; Obs. 469.1 [M$^+$+H].

Compound 9: (S)-6-(5-(((2-((4-methyl-3-oxo-3,4-dihydropyrido[2,3-b]pyrazin-6-yl)oxy)ethyl)amino) methyl)-2-oxooxazolidin-3-yl)-2H-pyrazino[2,3-b][1,4]oxazin-3(4H)-one

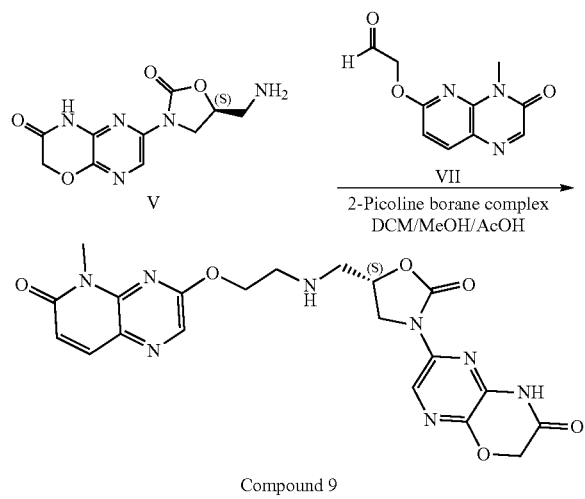

Compound 9

Compound 9 as formate salt was synthesized from intermediate V and Intermediate VII using procedure similar to Example 7.

$^1$H NMR (400 MHz, DMSO-D$_6$) δ 11.58 (s, br, 1H), 8.34 (s, 1H), 8.15-8.09 (m, 3H), 6.81 (d, 1H, J=8.8 Hz), 4.86 (s, 3H), 4.49-4.48 (m, 2H), 4.10-4.07 (m, 1H), 3.85-3.78 (m, 1H), 3.69 (s, 3H), 3.04-2.96 (m, 4H). LC_MS Calc. for C$_{20}$H$_{20}$N$_8$O$_6$ is 468.43; Obs. 469.1 [M$^+$+H].

Compound 10: (S)-6-(5-(((2-((7-fluoro-4-methyl-3-oxo-3,4-dihydropyrido[2,3-b]pyrazin-6-yl)oxy)ethyl) amino)methyl)-2-oxooxazolidin-3-yl)-2H-pyrazino[2,3-b][1,4]oxazin-3(4H)-one

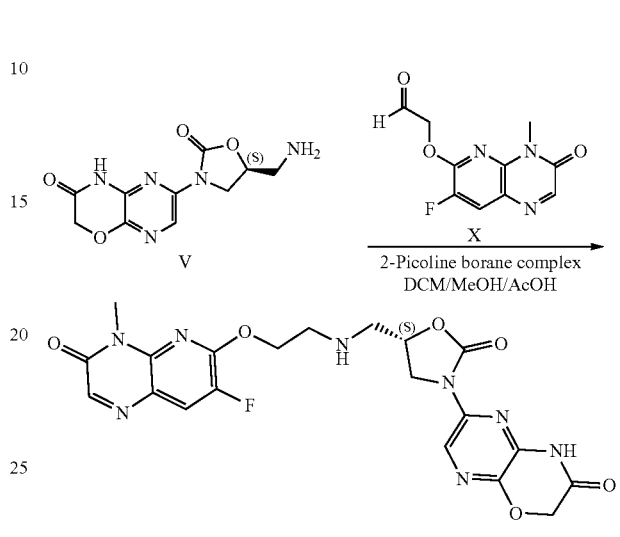

Compound 10

To a mixture of X (0.1 g, 0.4219 mmol) and V (0.13 g, 0.5063 mmol) in a mixture of dry MeOH (15 mL) and dichloromethane (15 mL) were added AcOH (0.3 mL) and 2-picoline borane complex (0.027 g, 0.25 mmol) successively at room temperature under nitrogen atmosphere. The resulting mixture was warmed to room temperature and stirred for 1 hour. After completion of the reaction, the reaction mixture was quenched with 1% HCOOH in water and concentrated in vacuo to get the crude. The crude obtained was further purified by preparative HPLC, the pooled fractions were concentrated and the resulting solid was triturated with diethyl ether to afford the title compound as formate salt (Compound 10, pale yellow solid).

$^1$H NMR (400 MHz, DMSO-d$_6$): δ 11.59 (s, br, 1H), 8.34 (s, 1H), 8.20-8.13 (m, 3H), 4.86-4.81 (m, 3H), 4.61-4.60 (m, 2H), 4.08-4.06 (m, 1H), 3.83-3.79 (m, 1H), 3.61 (s, 3H), 3.10-3.01 (m, 4H). LC_MS Calc. for C$_{20}$H$_{19}$FN$_8$O$_6$ is 486.42; Obs. 485.2 [M$^+$- H]; HPLC Purity=97.59%, Column: XBridge C8 (50×4.6) mm, 3.5 m, Mobile Phase A: 0.1% TFA in water, Mobile Phase B: Acetonitrile.

Compound 11: (S)-6-(5-(((2-((4-ethyl-3-oxo-3,4-dihydropyrido[2,3-b]pyrazin-6-yl)oxy)ethyl)amino) methyl)-2-oxooxazolidin-3-yl)-2H-pyrazino[2,3-b][1,4]oxazin-3(4H)-one

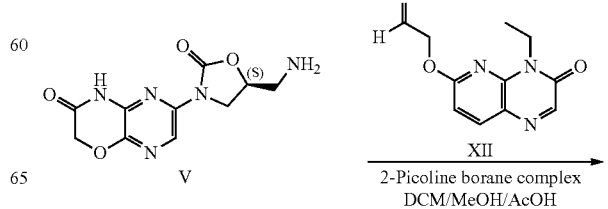

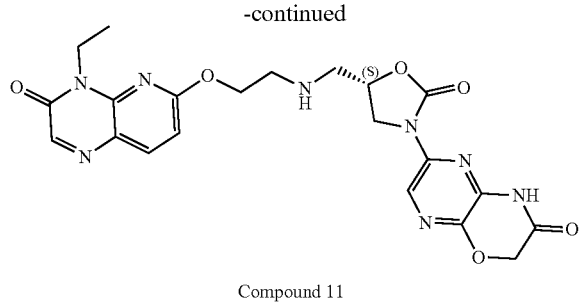

Compound 11

To a mixture of XII (0.15 g, 0.6437 mmol) and V (0.18 g, 0.7081 mmol) in a mixture of dry MeOH (20 mL)/dichloromethane (20 mL) were added AcOH (0.5 mL) followed by addition of 2-picoline borane complex (0.045 g, 0.4248 mmol) at room temperature. The resulting mixture was continued to stir for 1 hour. After completion of the reaction mixture, reaction mixture was quenched with 1% HCOOH in water and concentrated in vacuo. The crude obtained was further purified by preparative HPLC, the pooled fractions were concentrated and the resulting solid was triturated with diethyl ether to afford the title compound as formate salt (Compound 11, off white solid).

1H NMR (400 MHz, DMSO-$d_6$): δ 8.33 (s, 1H), 8.14-8.10 (m, 2H), 8.08 (m, 2H), 6.82-6.80 (d, J=8.6 Hz, 1H), 4.85-4.79 (m, 3H), 4.49-4.46 (m, 2H), 4.31-4.28 (m, 2H), 4.12-4.07 (m, 1H), 3.82 (m, 1H), 3.05-3.02 (m, 2H), 2.98-2.96 (m, 2H), 1.26-1.24 (t, 3H). LC_MS Calc. for $C_{21}H_{22}N_8O_6$, 482.46; Obs. 483.1 [M$^+$+H]. HPLC Purity=96.04%, Column: Atlantis dC18 (250×4.6) mm, 5 m, Mobile Phase A: 0.1% TFA in water, Mobile Phase B: Acetonitrile.

Compound 12: (S)-6-(5-(((2-((7-Chloro-4-methyl-3-oxo-3,4-dihydropyrido[2,3-b]pyrazin-6-yl)oxy)ethyl)amino)methyl)-2-oxooxazolidin-3-yl)-2H-pyrazino[2,3-b][1,4]oxazin-3(4H)-one

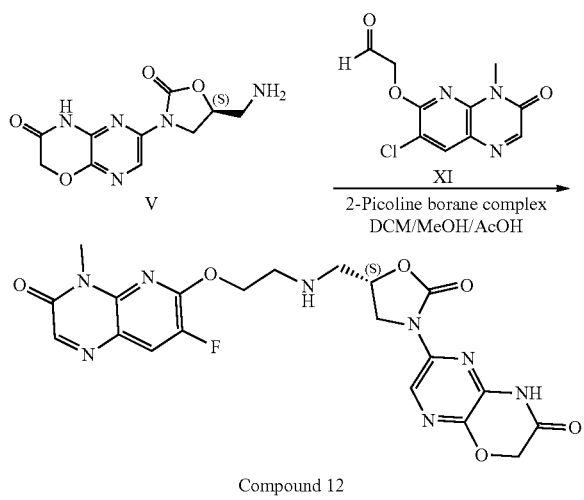

Compound 12

To a mixture of XI (0.15 g, 0.5928 mmol) and V (0.17 g, 0.6521 mmol) in a mixture of dry MeOH (20 mL)/DCM (20 mL) at room temperature under nitrogen atmosphere were added AcOH (0.5 mL) and 2-picoline borane complex (0.038 g, 0.3557 mmol) and stirred for 1 hour. After completion of the reaction, reaction mixture was quenched with 1% HCOOH in water and concentrated in vacuo to get the crude. The crude obtained was further purified by preparative HPLC, the pooled fractions were concentrated and the resulting solid was triturated with diethyl ether to afford the title compound as formate salt (Compound 12, 0.045 g, off white solid).

$^1$H NMR (400 MHz, DMSO-$d_6$): δ 8.33-8.31 (m, 2H), 8.13 (s, 1H), 4.85-4.78 (m, 3H), 4.56 (m, 2H), 4.07 (m, 1H), 3.82 (m, 2H), 3.59 (s, 3H), 3.17 (m, 2H), 3.05-2.97 (m, 4H).

LC_MS Calc. for $C_{20}H_{19}ClN_8O_6$ is 502.87; Obs: 503.1 [M$^+$+H]; HPLC Purity=95.08%, Column: Atlantis dC18 (250×4.6) mm, 5 m, Mobile Phase A: 0.1% Formic acid in water, Mobile Phase B: Acetonitrile.

Compound 13: (S)-5-(((2-((4-Methyl-3-oxo-3,4-dihydropyrido[2,3-b]pyrazin-6-yl)oxy)ethyl)amino)methyl)-3-(3-oxo-3,4-dihydro-2H-pyrazino[2,3-b][1,4]thiazin-6-yl)oxazolidin-2-one

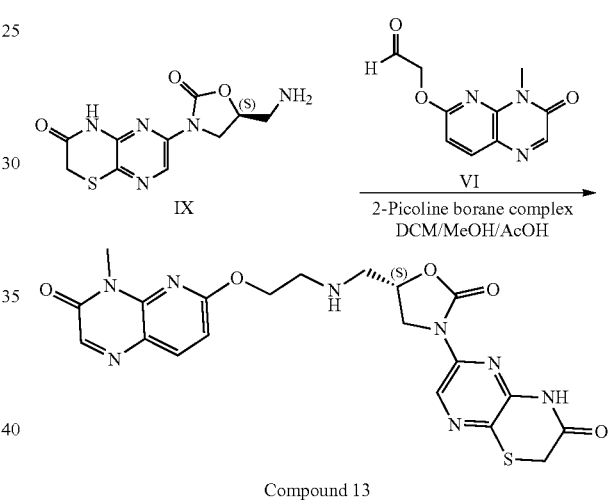

Compound 13

To a mixture of compound VI (0.2 g, 0.916 mmol) and compound IX (0.257 g, 0.916 mmol) in a mixture of dry methanol (20 mL)/dichloromethane (20 mL) was added AcOH (0.40 mL) under nitrogen atmosphere at room temperature and allowed to stir for 16 hours. To this was added 2-picoline borane complex (0.058 g, 0.549 mmol) and stirred for another 15 minutes at room temperature. The reaction mixture was quenched with 1% HCOOH in water and concentrated under reduced pressure to get crude product. The crude product was purified by column chromatography using silica gel (230-400 mesh) eluting with 6% methanol in dichloromethane to afford the title compound as formate salt (Compound 13, pale yellow solid (0.100 g, 22.43%).

$^1$H NMR (400 MHz, DMSO-$D_6$): 311.68 (brs, 1H), 8.75 (s, 1H), 8.19 (brs, 1H), 8.09-8.07 (m, 2H), 6.79 (d, J=8.8 Hz, 1H), 4.83-4.79 (m, 1H), 4.48-4.44 (m, 2H), 4.10-4.05 (m, 1H), 3.84-3.80 (m, 1H), 3.75 (s, 3H), 3.59 (s, 3H), 3.01-2.94 (m, 4H). LC_MS: Calc. for $C_{20}H_{20}N_8O_5S$ 484.49; Obs. 482.8 [M$^+$-H]. HPLC: 98.55%; 2.18 min; HPLC Column: X-Bridge $C_{18}$ (50*4.6) mm 3.5 μm, Mobile Phase A: 0.1% TFA in water, Mobile Phase B: Acetonitrile.

Compound 14: (S)-5-(((2-((5-Methyl-6-oxo-5,6-dihydropyrido[2,3-b]pyrazin-3-yl)oxy)ethyl)amino)methyl)-3-(3-oxo-3,4-dihydro-2H-pyrazino[2,3-b][1,4]thiazin-6-yl)oxazolidin-2-one

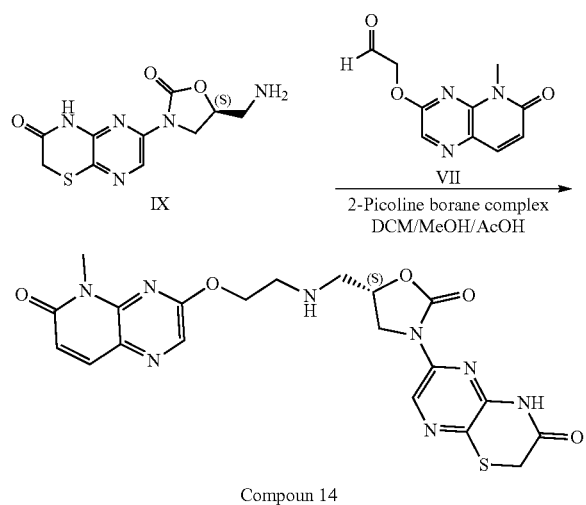

Compoun 14

To a mixture of VII (0.17 g, 0.77 mmol) and IX (0.24 g, 0.853 mmol) in a dry MeOH (20 mL)/DCM (20 mL) were added AcOH (0.2 mL) and 2-picoline borane complex (0.058 g, 0.54 mmol) at room temperature under nitrogen atmosphere. The resulting mixture was continued to stir at room temperature for 1 hour. After completion of the reaction mixture, reaction mixture was quenched with 1% HCOOH in water and concentrated in vacuo to get the crude. The crude was purified by column chromatography by eluting with 7% methanol in dichloromethane. The pure product obtained was further triturated with diethyl ether to afford pure product as formate salt (Compound 14, pale yellow solid, 25 mg, and 8.68%) 1H NMR (400 MHz, DMSO-$d_6$): δ 11.23 (brs, 1H), 8.77 (s, 1H), 8.18-8.15 (m, 2H), 7.93 (d, J 12.00 Hz, 1H), 6.72 (d, J 12.00, Hz, 1H), 4.83 (s, 1H), 4.53-4.52 (m, 2H), 4.11-4.07 (m, 1H), 3.86-3.82 (m, 3H), 3.62 (s, 3H), 3.06-2.98 (m, 4H). LC_MS Calc. for $C_{20}H_{20}N_8O_5S$ is 484.49; Obs.484.9 [M$^+$+H]; HPLC Purity=98.00%, X-Bridge $C_8$ (50×4.6) mm, mm,5 m, Mobile Phase A: 0.1% TFA in water, Mobile Phase B: Acetonitrile Example 4

Biological Activity (Antibacterial activity): The compounds of Formula (I) are of interest due to their potent antibacterial effects. The ability of the disclosure compounds disclosed herein to achieve an antibacterial effect may be evaluated with regard to their ability to inhibit the growth of bacterial species like *Escherichia coli* ATCC 25922, *Staphylococcus aureus* ATCC 29213, *Klebsiella pneumoniae* ATCC 13883, *Acinetobacter baumannii* ATCC 19606, *Pseudomonas aeruginosa* ATCC 27853 and *Enterococcus faecalis* ATCC 29212 using an assay based on the following Minimum Inhibitory Concentration (MIC) protocol:

The test bacteria are grown in Luria Bertani Broth (HIMEDIA M1245), 25 grams of the powder is dissolved in 1000 ml distilled water and sterilized by autoclaving at 15 lbs pressure (121° C.) for 20 minutes. The medium sterility is checked by incubating at 37° C. for a period of 48 h.

Bacterial cultures that are stored as glycerol stocks at −80° C. are sub cultured on LB agar plates to obtain isolated colonies. A single colony of each strain is cultured in LB broth. The cultures are incubated at 37° C., 200 rpm till they reach an optical density (OD at 600 nm) of 0.8 to 1. This log phase culture is diluted in LB broth to a cell number of 5-8*10^5 CFU/mL to be used as inoculum for MIC experiments. Test compounds are dissolved in dimethyl sulfoxide (DMSO) to a stock concentration of 4 mg/ml. A twofold dilution series of this DMSO stock is prepared in a 96 well V bottom microtitre plate from rows A to H. A 3 μL volume of these dilutions are transferred to a 96-well flat bottom microtitre assay plate. Controls to monitor the effects of DMSO and media sterility are included. Each well is inoculated with 150 μL of the above diluted culture. The plates are incubated at 37° C. overnight in a humidified incubator. The following morning, the plates are read using a Spectrophotometer at 600 nM wavelength. Minimum Inhibitory Concentration (MIC) is defined as the lowest drug concentration containing well which shows no turbidity. The antibacterial activity (MIC) determined against representative Gram positive (*S. aureus, E. aecalis*) and Gram negative (*E. coli P. aaurigenosa and A. baumanni*) pathogen were reported Table 1. The exemplified compounds belonging to Formula I demonstrated potent antibacterial activity both Gram positive and Gram negative pathogens.

TABLE 1

| | Table 1 | | | | | |
|---|---|---|---|---|---|---|
| | Minimum Inhibitory Concentration (μg/mL) in LB Media | | | | | |
| Compound | S. aureus ATCC 29213 | E. faecalis ATCC 29212 | E. coli ATCC 25922 | P. aurigenosa ATCC 27853 | K. pneumoniae ATCC 13883 | A. baumannii ATCC 19606 |
| 1 | 0.13 | 0.5 | 0.06 | 1 | 0.25 | 0.06 |
| 2 | 0.06 | 1 | 0.13 | 0.5 | 0.25 | 0.06 |
| 3 | 0.06 | 0.25 | 0.06 | 2 | 0.25 | 0.06 |
| 4 | 0.06 | 0.25 | 0.06 | 2 | 0.25 | 0.06 |
| 5 | 0.25 | 0.5 | 0.25 | 4 | 0.25 | 0.25 |
| 6 | 0.13 | 0.25 | 0.13 | 2 | 0.25 | 0.13 |
| 7 | 0.06 | 0.25 | 0.06 | 1 | 0.13 | 0.25 |
| 8 | 0.125 | 0.5 | 0.06 | 1 | 0.25 | 0.5 |
| 9 | 0.125 | 0.5 | 0.06 | 1 | 0.25 | 0.5 |
| 10 | 0.06 | 0.25 | 0.06 | 1 | 0.25 | 0.5 |
| 11 | 0.03 | 1 | 0.125 | 2 | 0.5 | 0.5 |
| 12 | 0.125 | 0.25 | 0.125 | 4 | 0.25 | 0.5 |

TABLE 1-continued

| | Minimum Inhibitory Concentration (µg/mL) in LB Media | | | | | |
|---|---|---|---|---|---|---|
| Compound | S. aureus ATCC 29213 | E. faecalis ATCC 29212 | E. coli ATCC 25922 | P. aurigenosa ATCC 27853 | K. pneumoniae ATCC 13883 | A. baumannii ATCC 19606 |
| 13 | ≤0.03 | 0.1 | 0.03 | 0.5 | 0.03 | 0.03 |
| 14 | ≤0.03 | 0.03 | 0.03 | 0.5 | 0.03 | 0.03 |
| Ciprofloxacin | 0.4 | 0.4 | 0.012 | 0.1 | 0.05 | 0.4 |

Example 5

Enzyme Inhibition Assay: Determination $IC_{50}$ Against E. coli Gyrase Supercoiling and E. coli Topo IV Decatenation The compounds belonging to Formula I or its stereoisomers, pharmaceutically acceptable salts, complexes, hydrates, solvates, tautomers, polymorphs, racemic mixtures, optically active forms and pharmaceutically active derivative thereof, for use in killing or inhibiting the growth of Gram-positive and Gram-negative bacteria through inhibition of bacterial Type II topoisomerases namely, DNA gyrase and Topo IV The present disclosure also provides evidence for treating infection caused both Gram positive and Gram negative bacteria through the inhibition of bacterial topoisomerases using E. coli DNA gyrase and Topo IV enzymes Procedure for E. coli DNA gyrase supercoiling Assay E. coli gyrase supercoiling and its inhibition was assayed using a kit procured from Inpiralis (K0001) and the protocol (PMID: 2172086) was adapted with necessary modifications. The compounds to be tested weree incubated for 10 minutes with 2.5 nM of E. coli DNA gyrase in a 30 µl reaction volume and 3.2% DMSO. The reactions were then started with the addition of 60 ng relaxed pBR322 plasmid DNA and continued for 45 min at 37° C. The reaction mixture contained 35 mM Tris.HCl (pH 7.5), 24 mM KCl, 1.8 mM spermidine, 4 mM $MgCl_2$, 2 mM DTT, 6.5% (w/v) glycerol, 0.1 mg/mL BSA, and 1 mM ATP. The reaction was then stopped by addition of 0.75 L of Proteinase K (20 mg/mL) and 3 µL of 2% SDS and further incubated at 37° C. for 30 min. This was followed by the addition of 4 µL of STEB (40% (w/v) sucrose, 100 mM Tris-HCl pH8, 1 mM EDTA, 0.5 mg/ml Bromophenol Blue), and the supercoiled/relaxed forms of plasmid DNA were separated by agarose gel electrophoresis. The 1% agarose gels were run for 3 h at 4V/cm in 1×TAE (40 mM Tris, 20 mM Acetic acid, 1 mM EDTA). To visualize the DNA the gels were stained for 10 min with 0.7 g/mL ethidium bromide and excess dye was removed by several washes with water. $IC_{50}$ were determined by quantifying the supercoiled and relaxed DNA in each of the reactions from a gel image by a densitometric method using the Quantity One Software (Bio-rad).

Procedure for E. coli Topoisomerase IV Decatenation Assay

E. coli topoisomerase IV decatenation activity and its inhibition was assayed using a kit procured from Inpiralis (D4002) and the kit protocol was adapted with necessary modifications similar to the gyrase supercoiling assays. The compounds to be tested were incubated for 10 minutes with 5 nM of E. coli topoisomerase IV in a 30 µl reaction volume and 3.2% DMSO. The reactions were started with the addition of 60 ng of kDNA and continued for 40 min at 37° C. The final reaction mixture contains 40 mM Tris.HCl (pH 7.6), 100 mM potassium glutamate, 10 mM magnesium acetate, 10 mM DTT, 1 mM ATP, and 50 µg/ml albumin. The reactions were stopped by addition of 0.75 L of Proteinase K (20 mg/mL) and 3 L of 2% SDS and further incubated at 37° C. for 30 min. This was followed by the addition of 4 L of STEB (40% (w/v) sucrose, 100 mM Tris-HCl pH8, 1 mM EDTA, 0.5 mg/ml Bromophenol Blue) and the kDNA/minicircles forms were separated by agarose gel electrophoresis. The 1% agarose gels were run for 3 h at 4V/cm in 1×TAE (40 mM Tris, 20 mM Acetic acid, 1 mM EDTA). To visualize the DNA, the gels were stained for 10 min with 0.7 µg/mL ethidium bromide and excess dye was removed by several washes with water. $IC_{50}$ were determined by quantifying the Kinetoplast DNA band inside the gel well and decatenated minicircles that migrate into the gel in each of the reactions from a gel image by a densitometric method using the Quantity One Software (Bio-rad).

Representing examples belonging to Formula I were evaluated against of E. coli DNA gyrase and Topo IV enzyme using gel based supercoiling assay for gyrase inhibition and decatenation assay for Topo IV inhibition. The results of bacterial Type II Topo isomerases (Gyrase and Topo IV) are presented in the Table 2. The results presented in the Table 2 indicates that compounds belonging to Formula I exerts its' antibacterial activity through inhibition bacterial type II topoisomerase activity and signifies the dual mode of inhibition for observed antibacterial activity of the compounds.

TABLE 2

| Compound | E. coli DNA Gyrase $IC_{50}$ (µM) | E. coli Topo IV $IC_{50}$ (µM) |
|---|---|---|
| 1 | 0.067 | 0.041 |
| 2 | 0.027 | 0.020 |
| 3 | 0.047 | 0.125 |
| 4 | 0.051 | 0.241 |
| 5 | 0.032 | 0.176 |
| 7 | 0.018 | 0.048 |
| Ciprofloxacin | 0.233 | 14.4 |

To test if the compounds from the series were able to retain the antibacterial activity against clinical strains of bacteria, antibacterial susceptibility studies ($MIC_{50}$ and $MIC_{90}$ determination) were carried for a representative compound (Compound 7) from the series using clinical strains of five gram negative bacterial species (E. coli, P. aurigenosa, K. pneumoniae, A. baumannii, E. cloacae) according the standard CLSI guidelines and the results obtained are presented Table 3. The standard drugs ciprofloxacin and meropenem were as positive control in the study.

TABLE 3

Results of MIC$_{50}$ and MIC$_{90}$ studies

| | Ciprofloxacin | Meropenem | Compound 7 | Compound 14 |
|---|---|---|---|---|
| *E. coli* | | | | |
| Number of strain | 201 | 201 | 176 | 176 |
| ATCC25922 | 0.015 | 0.06 | 0.06 | 0.03 |
| Minimum | 0.015 | 0.03 | 0.03 | 0.03 |
| MIC$_{50}$ (µg/ml) | 16 | 0.06 | 0.25 | 0.06 |
| MIC$_{90}$ (µg/ml) | 16 | 4 | 0.5 | 0.25 |
| *A. baumannii* | | | | |
| Number of strain | 169 | 169 | 132 | 176 |
| ATCC19606 | 0.5 | 0.5 | 0.25 | 0.03 |
| Minimum | 0.06 | 0.03125 | 0.06 | 0.03 |
| MIC$_{50}$ (µg/ml) | 16 | 8 | 0.5 | 0.25 |
| MIC$_{90}$ (µg/ml) | 16 | 32 | 0.5 | 0.5 |
| *K. pneumoniae* | | | | |
| Number of strain | 211 | 211 | 176 | 176 |
| ATCC13883 | 0.03 | 0.06 | 0.13 | 0.03 |
| Minimum | 0.015 | 0.03 | 0.125 | 0.03 |
| MIC$_{50}$ (µg/ml) | 4 | 1 | 1 | 0.25 |
| MIC$_{90}$ (µg/ml) | 16 | 16 | 4 | 0.5 |
| *P. aurigenosa* | | | | |
| Number of strain | 215 | 215 | 176 | 176 |
| ATCC27853 | 0.25 | 0.5 | 1 | 0.5 |
| Minimum | 0.015 | 0.03 | 0.06 | 0.06 |
| MIC$_{50}$ (µg/ml) | 0.125 | 2 | 0.5 | 0.5 |
| MIC$_{90}$ (µg/ml) | 16 | 8 | 2 | 1 |
| *E. cloacae* | | | | |
| Number of strain | 88 | 88 | 88 | 88 |
| Minimum | 0.06 | 0.06 | 0.06 | 0.03 |
| MIC$_{50}$ (µg/ml) | 0.06 | 0.25 | 0.5 | 0.25 |
| MIC$_{90}$ (µg/ml) | 16 | 16 | 2 | 0.5 | hERG Inhibition Assay

To test if the compounds from the series has any safety risk by inhibiting cardiac ion channel, particularly the potassium channel (IKr, hERG), compoundS were tested using electrophysiological assays to evaluate its potential activity on hERG ion channel. The compounds were tested for inhibition of the human ether a go-go related gene (hERG) K+ channel using QPatch HTX automated electrophysiology. 6-Point concentration-response curves were generated using three-fold serial dilutions from a maximum final test concentration of 300 µM and the results are presented in table 4.

Compounds were solubilised to 100 mM in DMSO before dilution in HBPS to 300 µM. 6-Point concentration-response curves were generated using 3.16-fold serial dilutions from the top test concentration.

Procedure:

Electrophysiological recordings were made from a Chinese Hamster Ovary cell line stably expressing the full-length hERG potassium channel. Single cell ionic currents were measured in whole-cell patch clamp configuration at room temperature (21-23° C.) using the QPatch HTX platform (Sophion). Intracellular solution contained (mM): 120 KF, 20 KCl, 10 EGTA, 10 HEPES and was buffered to pH 7.3. The extracellular solution (HEPES-buffered physiological saline, HBPS) contained (mM): 145 NaCl, 4 KCl, 2 CaCl$_2$, 1 MgCl$_2$, 10 HEPES, 10 glucose, buffered to pH7.4. Cells were clamped at a holding potential of −80 mV. Cells were stepped to +20 mV for 2 s then −40 mV for 3s before returning to the holding potential. This sweep was repeated 10 times at 10 s intervals. hERG currents were measured from the tail step and referenced to the holding current. Compounds were then incubated for 2 minutes prior to a second measurement of ion channel current using an identical pulse train.

TABLE 4 hERG IC$_{50}$ values

| Compound | hERG IC$_{50}$ (µM) |
|---|---|
| 3 | 40 |
| 4 | 38 |
| 5 | 82 |
| 6 | 60 |
| 7 | >300 |
| 8 | >300 |
| 9 | >100 |
| 10 | >300 |
| 12 | 98 |
| 13 | 58 |
| 14 | >150 |
| Cisapride | 0.15 |

Advantage

The above mentioned implementation examples as described on this subject matter and its equivalent thereof have many advantages, including those which are described.

The compounds of the present disclosure show high antibacterial activity against various pathogens including Gram-positive and Gram-negative bacteria through the inhibition of bacterial topoisomerase via a novel mechanism.

Although the subject matter has been described in considerable detail with reference to certain embodiments thereof, other embodiments are possible. As such, the spirit and scope of the disclosure should not be limited to the description of the embodiments contained herein.

We claim:

1. A compound of Formula I

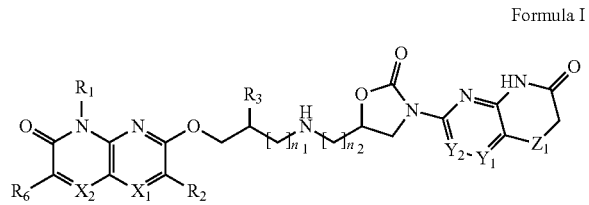

Formula I or its stereoisomers, pharmaceutically acceptable salts, complexes, hydrates, solvates, tautomers, polymorphs, racemic mixtures, optically active forms and pharmaceutically active derivatives thereof, wherein R$_1$ is selected from C$_{1-6}$ alkyl, C$_{2-6}$ alkenyl, C$_{3-6}$ cycloalkyl, C$_{1-6}$ alkylamino, C$_{1-6}$ aminoalkylene, or 4-7 membered saturated or unsaturated carbocyclyl or heterocyclyl ring, wherein the heterocyclyl ring is optionally substituted with up to three heteroatoms independently selected from O, N, or S, wherein C$_{1-6}$ alkyl, C$_{2-6}$ alkenyl, C$_{3-6}$ cycloalkyl, C$_{1-6}$ alkylamino, C$_{1-6}$ aminoalkylene, and 4-7 membered saturated or unsaturated carbocyclyl or heterocyclyl ring are optionally substituted with 1 to 3 groups independently selected from halogen, amino, hydroxy, SO$_3$H, O—PO$_3$H$_2$, COOR$_8$, CONHR$_8$, SO$_2$NHR$_8$, methylsulfone, C$_{1-6}$ alkyl, C$_{1-6}$ alkoxy, C$_{1-6}$ haloalkoxy, C$_{3-6}$ cycloalkyl, C$_{3-6}$ cycloalkylamino, C$_{3-6}$ aminocycloalkyl, C$_{3-6}$ cycloalkylhydroxy, C$_{1-6}$ alkylamino, or 3-7 membered saturated or unsaturated heterocyclyl ring optionally substituted with up to three heteroatoms independently selected from O, N, or S;

$R_8$ is selected from hydrogen, or $C_{1-6}$ alkyl;

$R_2$ is selected from hydrogen, halogen, hydroxyl, cyano, $C_{1-6}$ alkoxy, $C_{1-6}$ haloalkyl, $C_{1-6}$ haloalkoxy, or $C_{1-6}$ alkyl;

$R_3$ is selected from hydrogen, fluoro, $C_{1-4}$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$n_1$ is 0 or 1; $n_2$ is 1 or 2;

$R_6$ is selected from hydrogen, $C_{1-6}$ alkoxy, or $C_{1-6}$ alkyl;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

2. The compound as claimed in claim 1, or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with up to three heteroatoms independently selected from O, N, or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_8$, $CONHR_8$, $SO_2NHR_8$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ cycloalkylhydroxy, $C_{3-6}$ aminocycloalkyl, $C_{1-6}$ alkylamino, or 3-7 membered saturated or unsaturated heterocyclyl ring optionally substituted with up to three heteroatoms independently selected from O, N, or S;

$R_8$ is selected from hydrogen, or $C_{1-6}$ alkyl;

$R_2$ is selected from hydrogen, fluoro, chloro, $C_{1-4}$ alkoxy, cyano, hydroxyl, or $C_1$-alkyl;

$R_3$ is selected from hydrogen, fluoro, $C_{1-4}$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, or $C_1$ alkyl;

$n_1$ is 0 or 1; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

3. The compound as claimed in claim 1, or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $C_{1-4}$ alkyl, $C_{2-6}$ alkenyl, $C_{3-4}$ cycloalkyl, $C_{1-4}$ alkylamino, or 4-7 membered saturated carbocyclyl or heterocyclyl ring, wherein the heterocyclyl ring is optionally substituted with up to three heteroatoms independently selected from O, N, or S, wherein $C_{1-4}$ alkyl, $C_{1-4}$ haloalkyl, $C_{3-5}$ cycloalkyl, $C_{1-4}$ alkylamino, and 4-7 membered saturated carbocyclyl or heterocyclyl ring are optionally substituted with 1 to 3 groups independently selected from halogen, amino, hydroxyl, O—$PO_3H_2$, $C_{1-4}$ alkyl, $C_{1-4}$ alkoxy, $C_{1-4}$ haloalkoxy, $C_{3-5}$ cycloalkyl, $C_{3-5}$ cycloalkylamino, $C_{3-5}$ cycloalkylhydroxy, $C_{3-5}$ aminocycloalkyl, $C_{1-4}$ alkylamino, or 3-7 membered saturated or unsaturated heterocyclyl ring optionally substituted with up to three heteroatoms independently selected from O, N, or S;

$R_2$ is selected from hydrogen, fluoro, chloro, $C_1$ alkoxy, cyano, hydroxyl, or $C_1$-alkyl;

$R_3$ is selected from hydrogen, fluoro, $C_1$ alkoxy, hydroxyl, or amino;

$X_1$ is N or $CR_4$;

$R_4$ is selected from hydrogen, $C_{1-6}$ alkoxy, $C_{1-6}$ haloalkyl, $C_{1-6}$ haloalkoxy, or $C_{1-6}$ alkyl;

$X_2$ is N or $CR_5$;

$R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl;

$R_6$ is selected from hydrogen, or $C_1$ alkyl;

$n_1$ is 0 or 1; $n_2$ is 1 or 2;

$Y_1$, and $Y_2$ are independently selected from N or $CR_7$;

$R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; and $Z_1$ is selected from O, S, NH, or $CH_2$.

4. The compound as claimed in claim 1, or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2OCH_3CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$,

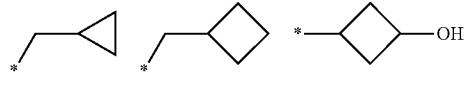

-continued

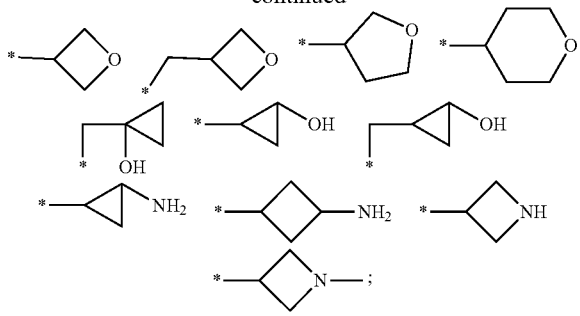

R$_2$ is selected from hydrogen, fluoro, chloro, methoxy, methyl, cyano, or hydroxyl;

R$_3$ is selected from hydrogen, fluoro, methoxy, hydroxyl, or amino;

X$_1$ is N or CR$_4$;

R$_4$ is selected from hydrogen, C$_{1-6}$ alkoxy, C$_{1-6}$ haloalkyl, C$_{1-6}$ haloalkoxy, or C$_{1-6}$ alkyl;

X$_2$ is N or CR$_5$;

R$_5$ is selected from hydrogen, cyano, COOH, CH$_2$COOH, CH$_2$OH, CH$_2$NH$_2$, CH(CH$_3$)NH$_2$, CH$_2$NHCH$_3$, CH$_2$NHCH$_2$CH$_2$OH, C$_{1-6}$ alkoxy, C$_{1-6}$ haloalkoxy, or C$_{1-6}$ alkyl;

R$_6$ is selected from hydrogen, or C$_1$ alkyl;

n$_1$ is 0 or 1; n$_2$ is 1 or 2;

Y$_1$, and Y$_2$ are independently selected from N or CR$_7$;

R$_7$ is selected from hydrogen, halogen, cyano, C$_{1-6}$ alkoxy, C$_{1-6}$ haloalkyl, C$_{1-6}$ haloalkoxy, or C$_{1-6}$ alkyl; and Z$_1$ is selected from O, S, NH, or CH$_2$.

5. The compound as claimed in claim 1, or its stereoisomers, pharmaceutically acceptable salts, complexes, hydrates, solvates, tautomers, polymorphs, racemic mixtures, optically active forms and pharmaceutically active derivatives thereof, which is selected from a group consisting of:

(Compound 1)

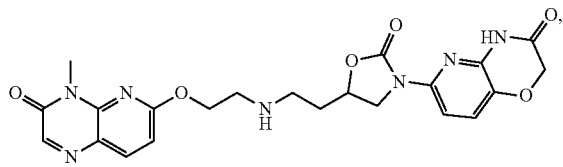

6-(5-(2-((2-((4-methyl-3-oxo-3,5-dihydropyrido[2,3-b]pyrazin-6-yl)oxy)ethyl)amino)ethyl)-2-oxooxazolidin-3-yl)-2H-pyrido[3,2-b][1,4]oxazin-3(4H)-one (Compound 2)

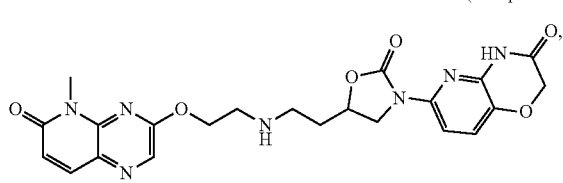

6-(5-(2-((2-((5-methyl-6-oxo-5,6-dihydropyrido[2,3-b]pyrazin-3-yl)oxy)ethyl)amino)ethyl)-2-oxooxazolidin-3-yl)-2H-pyrido[3,2-b][1,4]oxazin-3(4H)-one (Compound 3)

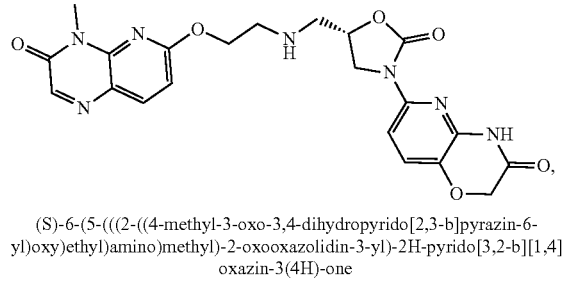

(S)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrido[3,2-b][1,4]oxazin-3(4H)-one (Compound 4)

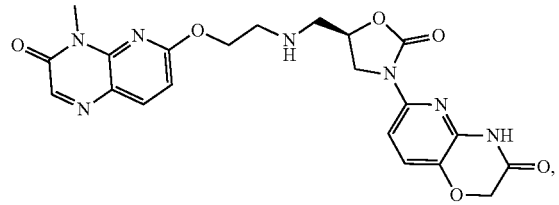

(R)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrido[3,2-b][1,4]oxazin-3(4H)-one (Compound 5)

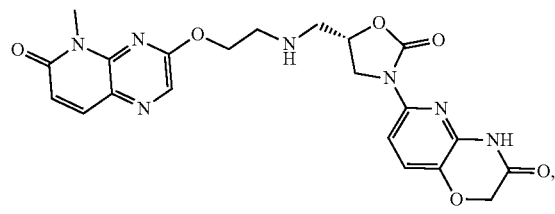

(S)-6-(5-(((2-((5-methyl-6-oxo-5,6-dihydropyrido[2,3-b]pyrazin-3-yl)oxy)ethyl)amino)methyl)-2-oxooxazolidin-3-yl)-2H-pyrido[3,2-b][1,4]oxazin-3(4H)-one (Compound 6)

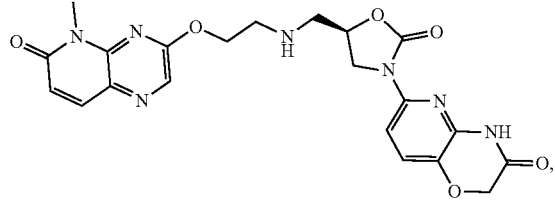

(R)-6-(5-(((2-((5-methyl-6-oxo-5,6-dihydropyrido[2,3-b]pyrazin-3-yl)oxy)ethyl)amino)methyl)-2-oxooxazolidin-3-yl)-2H-pyrido[3,2-b][1,4]oxazin-3(4H)-one (Compound 7)

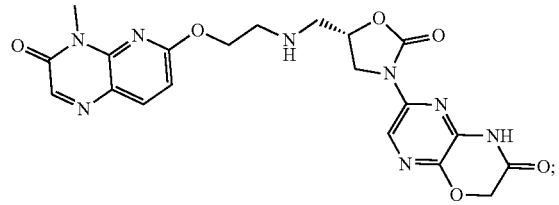

(S)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrido[3,2-b][1,4]oxazin-3(4H)-one

79

-continued (Compound 8)

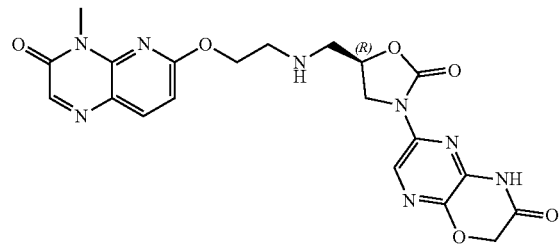

(R)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrazino[2,3-b][1,4]oxazin-3(4H)-one (Compound 9)

(S)-6-(5-(((2-((4-methyl-3-oxo-3,4-dihydropyrido[2,3-b]pyrazin-6-yl)oxy)ethyl)amino)methyl)-2-oxooxazolidin-3-yl)-2H-pyrazino[2,3-b][1,4]oxazin-3(4H)-one (Compound 10)

(S)-6-(5-(((2-((7-fluoro-4-methyl-3-oxo-3,4-dihydropyrido[2,3-b]pyrazin-6-yl)oxy)ethyl)amino)methyl)-2-oxooxazolidin-3-yl)-2H-pyrazino[2,3-b][1,4]oxazin-3(4H)-one (Compound 11)

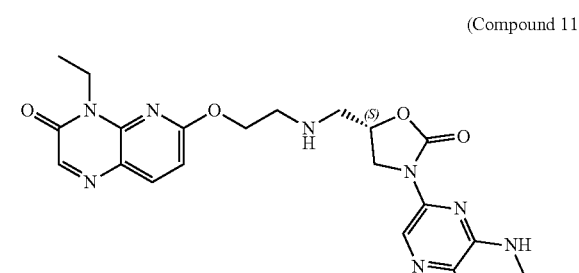

(S)-6-(5-(((2-((4-ethyl-3-oxo-3,4-dihydropyrido[2,3-b]pyrazin-6-yl)oxy)ethyl)amino)methyl)-2-oxooxazolidin-3-yl)-2H-pyrazino[2,3-b][1,4]oxazin-3(4H)-one

80

-continued (Compound 12)

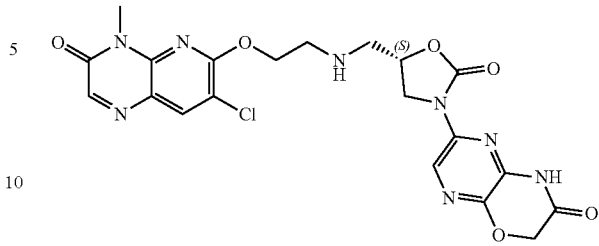

(S)-6-(5-(((2-((7-Chloro-4-methyl-3-oxo-3,4-dihydropyrido[2,3-b]pyrazin-6-yl)oxy)ethyl)amino)methyl)-2-oxooxazolidin-3-yl)-2H-pyrazino[2,3-b][1,4]oxazin-3(4H)-one (Compound 13)

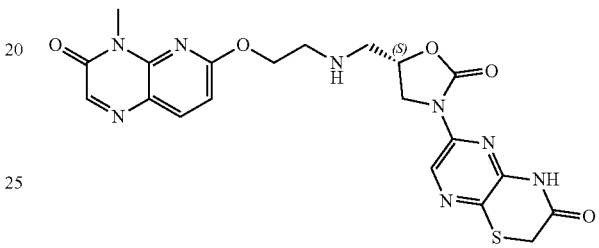

(S)-5-(((2-((4-Methyl-3-oxo-3,4-dihydropyrido[2,3-b]pyrazin-6-yl)oxy)ethyl)amino)methyl)-3-(3-oxo-3,4-dihydro-2H-pyrazino[2,3-b][1,4]thiazin-6-yl)oxazolidin-2-one (Compound 14)

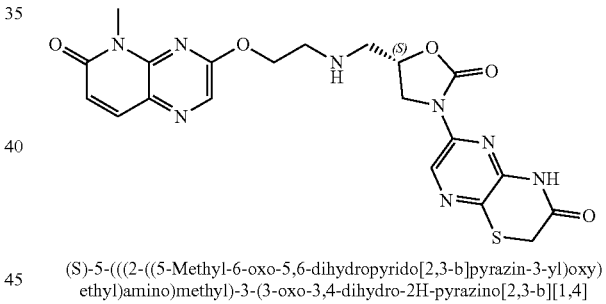

(S)-5-(((2-((5-Methyl-6-oxo-5,6-dihydropyrido[2,3-b]pyrazin-3-yl)oxy)ethyl)amino)methyl)-3-(3-oxo-3,4-dihydro-2H-pyrazino[2,3-b][1,4]thiazin-6-yl)oxazolidin-2-one.

6. A process of preparation of compounds of Formula I as claimed in claim 1, or its stereoisomers, pharmaceutically acceptable salts, complexes, hydrates, solvates, tautomers, polymorphs, racemic mixtures, optically active forms and pharmaceutically active derivative thereof, said process comprising reacting Formula (A), and Formula (B)

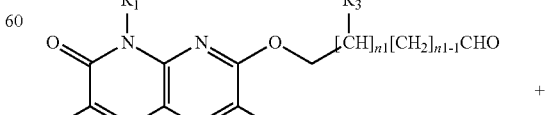

Formula (A)

-continued

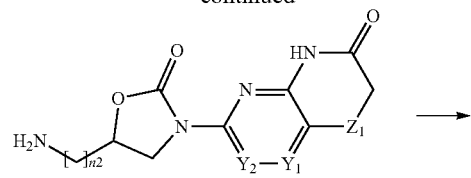

Formula (B)

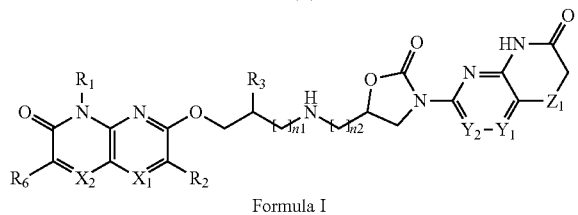

Formula I in presence of at least one reducing agent and an adsorbent to obtain the compounds of Formula I.

7. The process as claimed in claim 6, wherein $R_1$ of Formula (A) is selected from $C_{1-6}$ alkyl, $C_{2-6}$ alkenyl, $C_{3-6}$ cycloalkyl, $C_{1-6}$ alkylamino, $C_{1-6}$ aminoalkylene, or 4-7 membered saturated or unsaturated carbocyclyl or heterocyclyl ring, wherein the heterocyclyl ring is optionally substituted with up to three heteroatoms independently selected from O, N, or S, wherein $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered saturated or unsaturated carbocyclyl or heterocyclyl ring are optionally substituted with 1 to 3 groups independently selected from halogen, amino, hydroxyl, $SO_3H$, O—$PO_3H_2$, $COOR_9$, $CONHR_8$, $SO_2NHR_8$, methylsulfone, $C_{1-6}$ alkyl, $C_{1-6}$ alkoxy, $C_{1-6}$ haloalkoxy, $C_{3-6}$ cycloalkyl, $C_{3-6}$ cycloalkylamino, $C_{3-6}$ cycloalkylhydroxy, $C_{3-6}$ aminocycloalkyl, $C_{1-6}$ alkylamino, or 3-7 membered saturated or unsaturated heterocyclyl ring optionally substituted with up to three heteroatoms independently selected from O, N, or S; $R_8$ is selected from hydrogen, or $C_{1-6}$ alkyl; $R_2$ is selected from hydrogen, fluoro, cyano, $C_{1-6}$ alkoxy, or hydroxyl; $X_1$ is N or $CR_4$; $R_3$ is selected from hydrogen, $C_{1-6}$ alkyl, fluoro, $C_{1-6}$ alkoxy, hydroxyl, or amino; $R_4$ is selected from hydrogen, $C_{1-6}$ alkoxy, $C_{1-6}$ haloalkyl, $C_{1-6}$ haloalkoxy, or $C_{1-6}$ alkyl; $X_2$ is N or $CR_5$; $R_5$ is selected from hydrogen, cyano, $C_{1-6}$ alkyl, $C_{1-6}$ alkylamino, $C_{1-6}$ alkoxy, $C_{1-6}$ haloalkoxy, or COOH, wherein $C_{1-6}$ alkyl, and $C_{1-6}$ alkylamino are optionally substituted with one or more groups selected from COOH, hydroxyl, amino, or $C_{1-6}$ alkyl; and $n_1$ is 0 or 1; $R_6$ selected from hydrogen, or $C_{1-6}$ alkyl; $Y_1$, and $Y_2$ of Formula (B) are independently selected from N or $CR_7$; $R_7$ is selected from hydrogen, halogen, cyano, $C_{1-6}$ alkoxy, $C_{1-6}$ haloalkyl, $C_{1-6}$ haloalkoxy, or $C_{1-6}$ alkyl; $Z_1$ is selected from O, S, NH, or $CH_2$; $n_2$ is 1 or 2.

8. The process as claimed in claim 6, wherein the at least one reducing agent is selected from the group consisting of sodium borohydride, sodium cyano borohydride, sodium triacetoxy borohydride, and combinations thereof.

9. The process as claimed in claim 6, wherein the adsorbent is selected from the group consisting of molecular sieves, silicagel, zeolites, anhydrous sodium sulphate, anhydrous magnesium sulphate, activated charcoal, and combinations thereof.

10. A method for killing or inhibiting the growth of a microorganism in a subject, the microorganism being selected from the group consisting of bacteria, virus, fungi, and protozoa, the method comprising administering to the subject an effective amount of the compound as claimed in claim 1.

11. A pharmaceutical composition comprising a compound of Formula I as claimed in claim 1 or its stereoisomers, pharmaceutically acceptable salts, complexes, hydrates, solvates, tautomers, polymorphs, racemic mixtures, optically active forms and pharmaceutically active derivative thereof together with a pharmaceutically acceptable carrier.

12. A pharmaceutical composition comprising a compound of Formula I as claimed in claim 1 or its stereoisomers, pharmaceutically acceptable salts, complexes, hydrates, solvates, tautomers, polymorphs, racemic mixtures, optically active forms and pharmaceutically active derivative thereof together with a pharmaceutically acceptable carrier, and in combination with at least one antibiotic.

13. A method for treatment of bacterial infection in a subject comprising: administering to the subject an effective amount of the compound as claimed in claim 1.

14. The method as claimed in claim 13, wherein the bacterial infection is caused by a Gram-positive or a Gram-negative pathogen.

15. The method as claimed in claim 14, wherein the bacterial infection is caused by *E. coli, Pusedomonas aurigenosa, Klebsiella pneumoniae, Acinetobacter baumannii, Enterobacter cloacae, Staphylococcus aureus, Enterococcus faecalis Enterococcus faecium, Legionella pneumophila, Mycoplasma pneumonia, Acinetobacter haemolyticus Acinetobacter junii, Acinetobacter lwoffi, Burkholderia cepacia, Chlamydophila pneumoniae, Clostridium difficili, Enterobacter aerogenes, Enterobacter cloacae, Moraxella catarrhalis, Neisseria gonorrhoeae, Neisseria meningitides, Proteus mirabilis, Proteus houseri, Citrobacter freundii, Citrobacter kosari, Citrobacter barakii, Seratia marcescens, Klebsiella oxytoca, Morganella morganii, Helicobacter pyroli,* or *Mycobacterium tuberculosis.*

* * * * *